(12) United States Patent
Caponigro et al.

(10) Patent No.: US 10,011,874 B2
(45) Date of Patent: Jul. 3, 2018

(54) ANDROGEN RECEPTOR MUTATION

(71) Applicant: NOVARTIS AG, Basel (CH)

(72) Inventors: Giordano Caponigro, Cambridge, MA (US); Vesselina Cooke, Cambridge, MA (US); Scott Delach, Cambridge, MA (US); Joshua Korn, Cambridge, MA (US); Manav Korpal, Cambridge, MA (US); Wenlai Zhou, Newton, MA (US); Ping Zhu, Cambridge, MA (US)

(73) Assignee: Novartis AG, Basel (CH)

( * ) Notice: Subject to any disclaimer, the term of this patent is extended or adjusted under 35 U.S.C. 154(b) by 167 days.

(21) Appl. No.: 14/769,820

(22) PCT Filed: Feb. 24, 2014

(86) PCT No.: PCT/US2014/017977
§ 371 (c)(1),
(2) Date: Aug. 23, 2015

(87) PCT Pub. No.: WO2014/130932
PCT Pub. Date: Aug. 28, 2014

(65) Prior Publication Data
US 2016/0002727 A1 Jan. 7, 2016

Related U.S. Application Data

(60) Provisional application No. 61/768,860, filed on Feb. 25, 2013, provisional application No. 61/878,669, filed on Sep. 17, 2013.

(51) Int. Cl.
| | | |
|---|---|---|
| *C12Q 1/68* | (2018.01) |
| *A61K 31/519* | (2006.01) |
| *A61K 31/275* | (2006.01) |
| *A61K 31/4166* | (2006.01) |
| *G01N 33/74* | (2006.01) |
| *C12Q 1/6883* | (2018.01) |

(52) U.S. Cl.
CPC .......... *C12Q 1/6883* (2013.01); *A61K 31/275* (2013.01); *A61K 31/4166* (2013.01); *A61K 31/519* (2013.01); *G01N 33/743* (2013.01); *C12Q 2600/106* (2013.01); *C12Q 2600/156* (2013.01); *G01N 2333/723* (2013.01); *G01N 2800/52* (2013.01)

(58) Field of Classification Search
CPC .......... C12Q 1/6883; C12Q 2600/106; C12Q 2600/156; A61K 31/519; A61K 31/275; A61K 31/4166; G01N 33/743; G01N 2800/52; G01N 2333/723
See application file for complete search history.

(56) References Cited

U.S. PATENT DOCUMENTS

| | | |
|---|---|---|
| 4,097,578 A | 6/1978 | Perronnet et al. |
| 5,441,981 A | 8/1995 | Oppong et al. |
| 5,705,654 A | 1/1998 | Claussner et al. |
| 6,733,776 B1 | 5/2004 | Li |
| 7,067,256 B2 | 6/2006 | Roy et al. |
| 7,709,517 B2 | 5/2010 | Sawyers et al. |
| 8,183,274 B2 | 5/2012 | Sawyers et al. |
| 8,338,422 B2 | 12/2012 | Diels et al. |
| 8,338,454 B2 | 12/2012 | Menon |
| 8,338,624 B2 | 12/2012 | Kohen et al. |
| 9,700,557 B2 * | 7/2017 | Caponigro ........... A61K 31/519 |
| 2004/0009969 A1 | 1/2004 | Cleve et al. |
| 2010/0022632 A1 | 1/2010 | Hsiao et al. |
| 2012/0321639 A1 | 12/2012 | Nevalainen et al. |
| 2012/0322820 A1 | 12/2012 | Damaj et al. |
| 2012/0322834 A1 | 12/2012 | Flynn et al. |
| 2012/0329761 A1 | 12/2012 | Schimmer et al. |
| 2012/0329771 A1 | 12/2012 | Treu et al. |
| 2012/0329774 A1 | 12/2012 | Hutchings et al. |
| 2012/0329841 A1 | 12/2012 | Potter et al. |
| 2014/0199236 A1* | 7/2014 | Chen .................... A61K 9/0053 |
| | | 424/1.49 |

FOREIGN PATENT DOCUMENTS

| | | |
|---|---|---|
| EP | 0 692 972 B1 | 12/2001 |
| WO | WO 1997/000071 | 1/1997 |
| WO | WO 1997/011170 | 3/1997 |
| WO | WO 2000/017163 | 3/2000 |
| WO | WO2002/000617 | 6/2001 |
| WO | WO 2002/092129 | 11/2002 |
| WO | WO2005/072462 | 8/2005 |
| WO | WO 2007/140222 | 12/2007 |
| WO | WO 2010/020675 | 2/2010 |
| WO | WO2010/075074 | 7/2010 |
| WO | WO 2011/130232 | 10/2011 |
| WO | WO 2012/065051 | 5/2012 |
| WO | WO 2012/174095 | 12/2012 |
| WO | WO2014/018926 | 1/2014 |
| WO | WO2014/0666864 | 5/2014 |

OTHER PUBLICATIONS

Roberts et al., Multiple roles of cyclin-dependent kinase 4/6 inhibitors in cancer therapy. J. Natl. Cancer Inst. Mar. 21, 2012; 104(6):476-487.*
Murphy et al., The role of CDK4/6 inhibition in breast cancer. The Oncologist. May 2015; 20(5):483-490.*

(Continued)

*Primary Examiner* — Ruixiang Li
(74) *Attorney, Agent, or Firm* — David A. Carpenter

(57) ABSTRACT

Compositions and methods are provided for diagnosis, prognosis and treatment of AR-related diseases, such as prostate diseases, such as prostate cancer, breast cancer, and many other diseases. In particular, a novel and clinically relevant mutation at position 877 of the androgen receptor (AR) has been identified. Drug sensitivity can be predicted and therapeutic regimens can be planned on the basis of the presence or absence of this mutation. Polypeptides comprising, antibodies to, and polynucleotides encoding the mutant AR can be used to identify novel treatments. A double mutation in AR at positions 742 and 878 is also shown to be useful for patient stratification.

2 Claims, 43 Drawing Sheets

(56) References Cited

OTHER PUBLICATIONS

Joly-Pharaboz et al., "Inhibition of Growth and Induction of Apoptosis by Androgens of a Variant of LNCaP Cell Line" The Journal of Steroid Biochemistry and Molecular Biology 73(5):237-249, 2000.
Wang et al., "Isolation and Characterization of the Androgen Receptor Mutants with Divergent Transcriptional Activity in Response to Hydroxyflutamide" Endocrine 12(1):69-76, 2000.
Amato et al., "Kennedy's Disease: A Clinicopathologic Correlation with Mutations in the Androgen Receptor Gene" Neurology 43:791-794, 1993.
Andersen et al., "Regression of Castrate-Recurrent Prostate Cancer by a Small-Molecule Inhibitor of the Amino-Terminus Domain of the Androgen Receptor" Cancer Cell 17(6):535-546, 2010.
Balbas et al., "Overcoming Mutation-Based Resistance to Antiandrogens with Rational Drug Design" eLife 2:e00499, 2013.
Bardin et al., "Progestins can Nimic, Inhibit and Potentiate the Actions of Androgens" Pharmacol Ther 23:443-459, 1983.
Birrell et al., "Androgens Induce Divergent Proliferative Responses in Human Breast Cancer Cell Lines" J. Steroid Biochem Mol. Biol 52:459-467, 1995.
Buchanan et al., "Decreased Androgen Receptor Levels and Receptor Function in Breast Cancer Contribute to the Failure of Response to Medroxyprogesterone Acetate"Cancer Res. 65:8487-8496, 2005.
Carver et al., "Reciprocal Feedback Regulation of PI3K and Androgen Receptor Signaling in PTEN-Deficient Prostate Cancer" Cancer Cell 19:575-586, 2011.
Chen et al., "Defects of DNA Mismatch Repair in Human Prostate Cancer" Cancer Research 61:4112-4121, 2001.
Chen et al., "Molecular Determinants of Resistance to Antiandrogen Therapy" Nature Medicine 10:33-39, 2004.
Chen et al., "Discovery and Therapeutic Promise of Selective Androgen Receptor Modulators" Mol. Interv. 5(3):173-188, 2005.
Clegg et al., "ARN-509: A Novel Antiandrogen for Prostate Cancer Treatment" Cancer Research 72:1494-1503, 2012.
Collins et al., "Androgen Receptor Expression in Breast Cancer in Relation to Molecular Phenotype: Results from the Nurses' Health Study" Mod. Patol 24:924-931, 2011.
Culig et al., "Mutant Androgen Receptor Detected in an Advanced-Stage Prostatic Carcinoma is Activated by Adrenal Androgens and Progesterone" Molecular Endocrinology 7(12):1541-1550, 1993.
Culig et al., "Switch from Antagonist to Agonist of the Androgen Receptor Blocker Bicalutamide is Associated with Prostate Tumour Progression in a New Model System" British Journal of Cancer 81:242-251, 1999.
Dai et al., "Compensatory Upregulation of Tyrosine Kinase Etk/BMX in Response to Androgen Deprivation Promotes Castration-Resistant Growth of Prostate Cancer Cells" Cancer Research 70:5587-5596, 2010.
Dean et al., "Therapeutic CDK4/6 Inhibition in Breast Cancer: Key Mechanisms of Response and Failure" Oncogene 29:4018-4032, 2010.
Dean et al., "Therapeutic Response to CDK4/6 Inhibition in Breast Cancer Defined by ex vivo Analyses of Human Tumors" Cell Cycle 112756-2761, 2012.
Doane et al., "An estrogen Receptor-Negative Breast Cancer Subset Characterized by a Hormonally Regulated Transcriptional Program and Response to Androgen" Oncogene 25:3994-4008, 2006.
Fenton et al., "Functional Characterization of Mutant Androgen Receptors from Androgen-Independent Prostate Cancer" Clin Cancer Res 3:1383-1388, 1997.
Ferlini et al., "Androgen Receptor Gene (CAG)n Repeat Analsyis in Differential Diagnosis Between Kennedy Disease and Other Motoneuron Disorders" American Journal of Medical Genetics 55:105-111, 1995.
Finn et al., "PD 0332991, a Selective Cyclin D Kinase 4/6 Inhibitor, Preferentially Inhibits Proliferation of Luminal Estrogen Receptor-Positive Human Breast Cancer Cell Lines in vitro" Breast Cancer Res. 11(5):R77, 2009.

Fradet et al., "Bicalutamide (Casodex®) in the Treatment of Prostate Cancer" Expert Rev Anticancer Ther 4(1):37-48, 2004.
Furr "The Development of Casodex (Bicaulutamide): Preclinical Studies" European Urology 29(Supp 2):83-95, 1996.
Furr "The Preclinical Development of Bicalutamide: Pharmacodynamics and Mechanism of Action" Urology 471(Suppl 1A):13-25, Jan. 1996.
Gao, "Peptide Antagonist of the Androgen Receptor" Current Pharmaceutical Design 16:1106-1113, 2010.
Giovannucci et al., "CAG Repeat within the Androgen Receptor Gene and Incidence of Surgery for Benign Prostatic Hyperplasia in U.S. Physicians" Prostrate 39:130-134, 1999.
Gonzalez-Angulo et al., "Androgen Receptor Levels and Association with PIK3CA Mutations and Prognosis in Breast Cancer" Clin. Cancer Res 15:2472-2478, 2009.
Gorre et al., "Clinical Resistance to STI-571 Cancer Therapy Caused by BCR-ABL Gene Mutation or Amplification" Science 293:876-880, 2001.
Gregory et al., The Putative Androgen Receptor—A form Results from in vitro Proteolysis J. Mol. Endocrinol 27:309-319, 2001.
Haapala et al.,"Androgen Receptor Alterations in Prostate Cancer Relapsed During a Combined Androgen Blockade by Orchiectomy and Bicalutamide" Labor Invest 81:1647-1651, 2001.
Hara et al., "Novel Mutations of Androgen Receptor: A Possible Mechanism of Bicalutamide Withdrawal Syndrome" Cancer Research 63:149-153, 2003.
Heinlein et al., "The Roles of Androgen Receptors and Androgen-Binding Proteins in Nongenomic Androgen Actions" Molecular Endocrinology 16(10):2181-2187, Jul. 2, 2013.
Hillmer et al., "Genetic Variation in the Human Androgen Receptor Gene Is the Major Determinant of Common Early-Onset Androgenetic Alopecia" Am J. Human Genet 77(1):140-148, 2005.
Iacopetta et al., "The Role of Androgen Receptor in Breast Cancer" Drug Discovery Today: Disease Mechanisms 9(1-2):e19-e27, 2012.
Jemal et al., "Cancer Statistics, 2008" CA Cancer Journal for Clinicians 58:71-96, 2008.
Jemal et al., "Cancer Statistics, 2010" CA Cancer Journal for Clinicians 60:277-300, 2010.
Kawata et al., "Prolonged Treatment with Bicalutamide Induces Androgen Receptor Overexpression and Androgen Hypersensitivity" Prostate 70:745-754, 2010.
Kim et al., "Androgen Receptor Directed Therapies in Castration-Resistant Metastatic Prostate" Current Treatment Options in Oncology 13(2):189-200, 2012.
Klotz et al., "Combined Androgen Blockade : An Update" Urol. Clin. North Am. 33(2):161-166, 2006.
Levine et al., "A Phase II Evaluation of Goserelin and Bicalutamide in Patients with Ovarian Cancer in Second or Higher Complete Clinical Disease Remission" Cancer 110(11):2448-2456, Dec. 2007.
Li et al., "Androgen Receptor Splice Variants Mediate Enzalutamide Resistance in Castration-Resistant Prostate Cancer Cell Lines" Cancer Research 73:483-489, 2013.
Lu et al., "International Union of Pharmacology. LXV. The Pharmacology and Classification of the Nuclear Receptor Superfamily: Glucocorticoid, Mineralocorticoid, Progesterone, and Androgen Receptors" Pharmacol Rev 58:782-797, 2006.
Marberger "Long-Term Effects of Finasteride in Patients with Benign Prostatic Hyperplasia: A Double-Blind, Placebo-Controlled, Multicenter Study" Urology 51(5):677-686, May, 1998.
Marcelli et al., "Androgen Receptor Mutations in Prostate Cancer" Cancer Research 60:944-949, 2000.
Mocellini et al., "Finasteride (MK-906) in the Treatment of Benign Prostatic Hyperplasia" Prostate 22:291-299, 1993.
Moinfar et al., "Androgen Receptors Frequently are Expressed in Breast Carcinomas" Cancer 98:703-711, 2003.
Monks et al., "Overexpression of Wild-Type Androgen Receptor in Muscle Recapitulates Polyglutamine Disease" Proc Natl Acad Sci USA 104(46):18259-18264, Nov. 13, 2007.
Mooradian et al., "Biological Actions of Androgens" Endocrine Reviews 8(1):1-28, 1987.

(56) References Cited

OTHER PUBLICATIONS

Muderris et al., "New Alternative Treatment in Hirsutism: Bicalutamide 25 mg/day" *Gynecological Endocrinology* 16(1):63-66, 2002.
Mulholland et al., "Cell Autonomous Role of PTEN in Regulating Castration-Resistant Prostate Cancer Growth" *Cancer Cell* 19:792-804, 2011.
Naderi et al., "Synergy Between Inhibitors of Androgen Receptor and MEK has Therapeutic Implications in Estrogen Receptor-Negative Breast Cancer" *Breast Cancer Research* 13:R36, 2011.
Radar et al., "Abstract 2744: CDK4/CDK6 Inhibition is Potently Active in a Definable Subset of Human Neuroblastomas" *Cancer Research* 73:2744, Apr. 13, 2015.
Rahman et al., "Non-Classical Actions of Testosterone: an Update" *Trends Endocrin Metab.* 18:371-378, 2007.
Raudrant et al., "Progestogens with Antiandrogenic Properties" *Drugs* 63(5):463-492, 2003.
Roy et al., "Regulation of Androgen Action" *Vitamins and Hormones* 55:309-352, 1998.
Sawaya et al., "Androgen Receptor Polymorphisms (CAG Repeat Lengths) in Androgenetic Alopecia, Hirsutism, and Acne" Journal Cutaneous Med Surg 3(1):9-15, Nov. 1, 1998.
Schellhammer et al., "Clinical benefits of bicalutamide compared with flutamide in combined androgen blockade for patients with advanced prostatic carcinoma: Final report of a double-blind, randomized, multicenter trial" *Urology* 50(3):330-336, 1997.
Schellhammer et al., "An Evaluation of Bicalutamide in the Treatment of Prostate Cancer" *Expert Opin Pharmacother* 3(9):1313-1328, 2002.
Scher and Sawyers "Biology of Progressive, Castration-Resistant Prostate Cancer: Directed Therapies Targeting the Androgen-Receptor Signaling Axis" *Journal of Clinical Oncology* 23:8253-8261, 2005.
Scher et al., "Increased Survival with Enzalutamide in Prostate Cancer after Chemotherapy" *New England Journal of Medicine* 367:1187-1197, 2012.
Schiewer et al., "mTOR is a Selective Effector of the Radiation Therapy Response in Androgen Receptor-Positive Prostate Cancer" *Endorcrine-Related Cancer* 19:1-12, 2012.
Schmidt et al., "Androgen Receptor in Hirsutism and Acne" *Gyn. Obstet. Invest.* 22:206-211, 1986.
See et al., "The Addition of Bicalutamide 150 mg to Radiotherapy Significantly Improves Overall Survival in Men with Locally Advanced Prostate Cancer" *Journal of Cancer Research and Clinical Oncology* 132(Suppl 1):S7-S16, Aug. 2006.
Suzuki et al., "Codon 877 Mutation in the Androgen Receptor Gene in Advanced Prostate Cancer: Relation to Antiandrogen Withdrawal Syndrome" *Prostate* 29:153-158, 1996.
Tan et al., "Dehydroepiandrosterone Activates Mutant Androgen Receptors Expressed in the Androgen-Dependent Human Prostate Cancer Xenograft CWR22 and LNCaP Cells" *Molecular Endocrinology* 11(4):450-459, 1997.
Thangavel et al., "Therapeutically Activating RB: Reestablishing Cell Cycle Control in Endocrine Therapy-Resistant Breast Cancer" *End. Relat. Cancer* 18:333-345, 2011.
Taplin et al., "Mutation of the Androgen-Receptor Gene in Metastatic Androgen-Independent Prostate Cancer" *The New England Journal of Medicine* 332:1393-1398, 1995.
Taplin et al., "Selection for Androgen Receptor Mutations in Prostate Cancers Treated with Androgen Antagonist" *Cancer Research* 59:2511-2515, 1999.
Taplin et al., "Androgen Receptor Mutations in Androgen-Independent Prostate Cancer: Cancer and Leukemia Group B Study 9663" *J. Clinical Oncology* 21:2673-2678, 2003.
Tran et al., "Development of a Second-Generation Antiandrogen for Treatment of Advanced Prostate Cancer" *Science* 324:787-790, 2009.
Veldscholte et al., "Anti-Androgens and the Mutated Androgen Receptor of LNCaP Cells: Differential Effects on Binding Affinity, Heat-Shock Protein Interaction, and Transcription Activation" *Biochemistry* 31(8):2393-2399, 1992.
Waller et al., "Androgen Receptor Localisation and Turnover in Human Prostate Epithelium Treated with the Antiandrogen, Casodex" *J. Mol. Endocrinol.* 24(3):339-351, 2000.
Watson et al., "Constitutively Active Androgen Receptor Splice Variants Expressed in Castration-Resistant Prostate Cancer Require Full-Length Androgen Receptor" *Proc. Natl. Acad. Sci.* 107:16759-16765, 2010.
Wilson et al., "A and B Forms of the Androgen Receptor are Present in Human Genital Skin Fibroblasts" *Proc. Natl. Acad. Sci. USA* 91:1234-1238, 1994.
Zhao et al., "Glucocorticoids can Promote Androgen-Independent Growth of Prostate Cancer Cells Through a Mutated Androgen Receptor" *Nature Medicine* 6:702-706, 2000.
Chen et al., "Expression of G1 Cyclins, Cyclin-Dependent Kinases, and Cyclin-Dependent Kinase Inhibitors in Androgen-Induced Prostate Proliferation in Castrated Rats" *Cell Growth & Differentiation* 7(11):1571-1578, Nov. 1996.
Liu et al., "Synthesis and in vitro Characterization of Ionone-Based Compounds as Dual Inhibitors of the Androgen Receptor and NF-κB" *Investigational New Drugs* 32(2):227-234 Oct. 2013.
Korpal et al., "An F876L Mutation in Androgen Receptor Confers Genetic and Phenotypic Resistance to MDV3100 (Enzalutamide)" *Cancer Discovery* 3(9):1030-1043, Jul. 2013.

\* cited by examiner

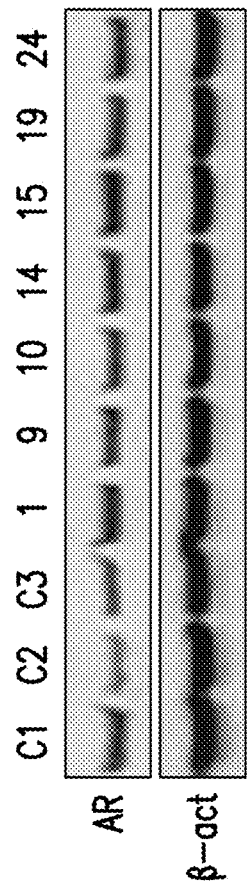
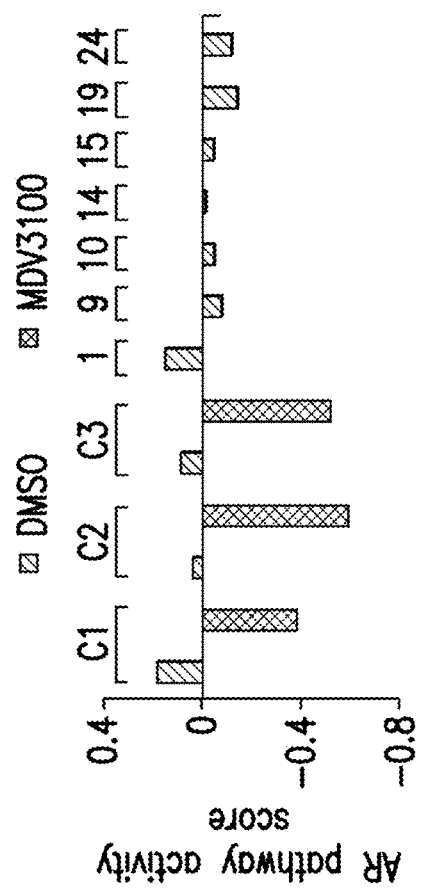
FIG.1D
FIG.1E

| Tumor | AA | Codon | Frequency of F877L |
|---|---|---|---|
| Control 1 (C1) | F | TTC | 0 |
| Control 2 (C2) | F | TTC | 0 |
| Resistant 1 (R1) | L | CTC | 52% |
| Resistant 1 (R2) | L | TTA | 50% |
| Resistant 1 (R3) | L | CTC | 46% |
| Resistant 4 (R4) | F | TTC | 0% |

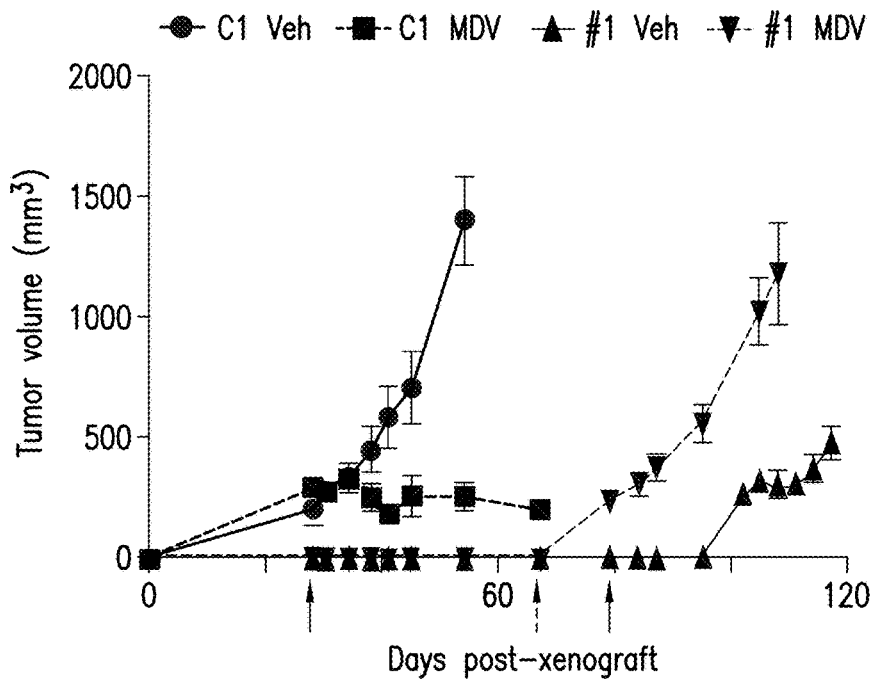
FIG.5E
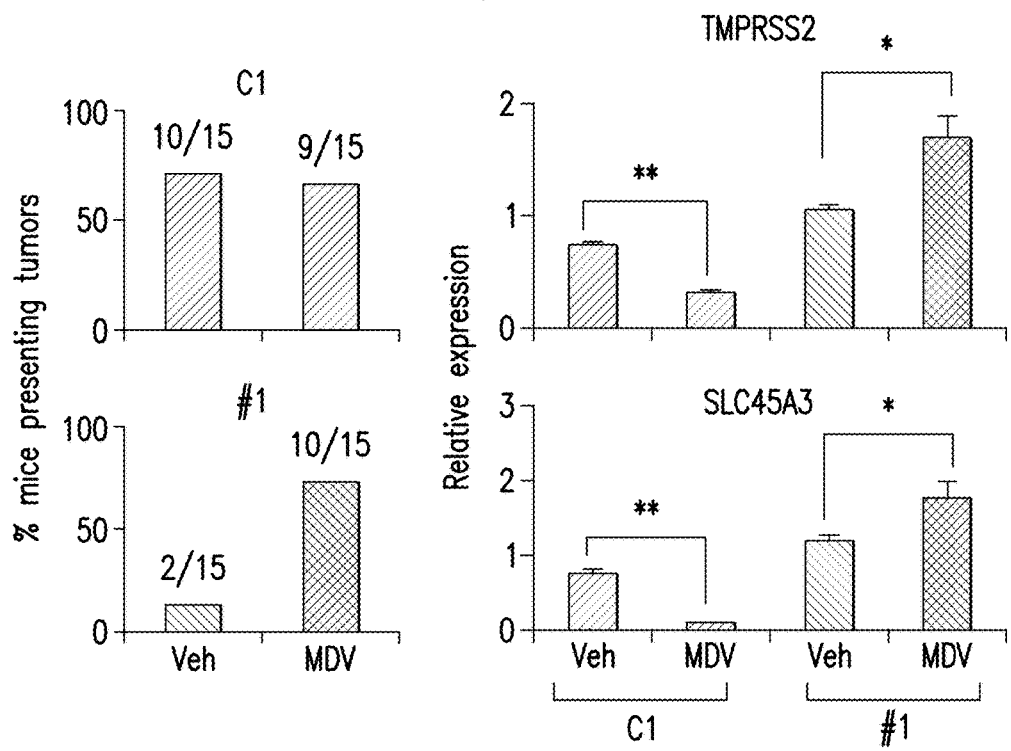
FIG.5F
FIG.5G

ANDROGEN RECEPTOR MUTATION

This application is a U.S. National Phase filing of International Application No. PCT/US2014/017977, filed Feb. 24, 2014, which claims priority to US Application No. 61/768,860 filed Feb. 25, 2013 and U.S. Application No. 61/878,669 filed on Sep. 17, 2013, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 24, 2014, is named PAT055531-WO-PCT.txt and is 40,101 bytes in size.

TECHNICAL FIELD

The present disclosure relates generally to compositions and methods useful for treating conditions associated with Androgen Receptor (AR), such as prostate diseases, such as prostate cancer (PCa), breast cancer, and various other diseases. The disclosure is more particularly related to compositions comprising an Androgen Receptor with a novel mutation at F877 or fragments or variants thereof [AR(F877)]. This mutation is useful for stratifying patients, predicting drug sensitivity and designing therapeutic regimens, as it renders the AR resistant to some therapeutics (such as MDV3100) and not others (such as anti-androgen bicalutamide, or CDK4/6 inhibitors LEE011 and PD0332991). This F877 mutation can even cause an antagonist-to-agonist switch for MDV3100. The present disclosure is also related to polypeptides comprising the mutant AR, antibodies to it and polynucleotides encoding it, all of which can be used to identity novel treatments for AR-related diseases. The disclosure also pertains to a double mutation in AR at positions W742 and T878, which also confers resistance to MDV3100. These AR mutations are thus useful for patient stratification and development of new therapeutics for AR-related diseases. The disclosure also pertains to methods of treatment of AR-related diseases, wherein the AR has a F877 or W742/T878 mutation. This disclosure also pertains to methods of treatment involving combinations of therapies.

BACKGROUND OF THE INVENTION

Androgen Receptor (AR) is a receptor which binds to ligands such as testosterone and dihydrotestosterone, and then translocates to the nucleus. There it acts as a DNA-binding transcription factor, regulating gene expression and many other functions.

Over-expression or mutation of AR has been implicated in various diseases, including cancer, including prostate cancer and many other diseases.

Prostate cancer is one of the most commonly diagnosed cancers in the world. Kawata et al. The Prostate 70, 745-754 (2010); and Jemal et al. CA 58, 71-96 (2008). Although localized tumors are often curative, distant metastases emerge in a significant fraction of patients. Scher et al. Journal of clinical oncology 23, 8253-8261 (2005); and Clegg et al. Cancer research 72, 1494-1503 (2012). Androgen-deprivation therapy, including surgical or chemical castration, is initially effective; however, resistance is almost always acquired that results in a much more aggressive form of tumor referred to as castration-resistant prostate cancer (CRPC). CRPC is the second most common cause of cancer-related deaths in American men [Jemal et al. CA: a cancer journal for clinicians 60, 277-300 (2010)] and is currently incurable. A conserved feature of CRPC is the sustained activity of AR-signaling [Chen et al. Nature medicine 10, 33-39 (2004)], by virtue of many mechanisms including AR gene overexpression/amplification and AR gene mutations. Scher et al. Journal of clinical oncology 23, 8253-8261 (2005). The continued reliance on AR signaling in CRPC led to the development of competitive inhibitors that compete with androgens for binding to the ligand-binding pocket of AR. Bicalutamide is such an anti-androgen that has been clinically used for many years as a monotherapy or in combination with castration to block androgen action. However, in the setting of CRPC, bicalutamide undergoes an antagonist-to-agonist switch, paradoxically enhancing AR signaling activity. Culig et al. British journal of cancer 81, 242-251 (1999).

Recently, a more potent anti-androgen, MDV3100 (enzalutamide, marketed as XTANDI® by Astellas Pharma US, Inc., Northbrook, Ill., and Medivation Inc., San Francisco, Calif.), has been discovered that lacks agonist activity. Tran et al. Science 324, 787-790 (2009). Based on convincing preclinical and clinical data, MDV3100 has been approved by the FDA for treatment of men with metastatic CRPC previously treated with docetaxel. On-going clinical trials are also testing MDV3100 as a monotherapy in patients with advanced prostate cancer who have not yet been castrated and as a neoadjuvant therapy in men diagnosed with prostate cancer but who have not yet undergone prostatectomy.

Although MDV3100 has shown tremendous efficacy in clinical trials, many who initially responded favorably have since developed resistance to this second generation anti-androgen. Kim et al. Current treatment options in oncology 13, 189-200 (2012).

There thus exists the need for novel compositions and methods for patient stratification and prediction of drug sensitivity for treatments for prostate cancer, breast cancer and other AR-related diseases. There also exists the need for novel therapies for AR-related diseases.

SUMMARY OF THE INVENTION

An object of this disclosure is to provide tools and methods for diagnosing, prognosing and treating Androgen Receptor (AR)-related diseases, such as prostate diseases, such as prostate cancer (PCa), including castration-resistant Pca (CRPC), and breast cancer, as well as other AR-related disorders such as polyglutamate disease, alopecia, benign prostatic hyperplasia, hirsutism, acne, spinal and muscular atrophy and Kennedy disease. This and other objections of the disclosure are provided by one or more of the embodiments described below.

In various aspects, the present disclosure pertains to a novel and clinically relevant mutation in AR, namely at position F877 (numbered in accordance with the sequence of SEQ ID NO: 1 or 54), which confers resistance to the therapeutic MDV3100, even causing an antagonist-to-agonist switch for this drug. The preset disclosure also pertains to patient stratification methods, involving the step of detecting the presence or absence of this mutation in a cell or tissue sample of a patient of an AR-related disease, and prescribing and designing a treatment plan in accordance. The present disclosure also pertains to a method of treating a patient with an Androgen Receptor (AR)-related disease, wherein the amino acid at position of 877 of AR is absent or is not phenylalanine, and wherein the method comprises the step of administering a therapeutic composition which comprises a CDK4/6 inhibitor. In various embodiments, the CDK4/6 inhibitor is LEE011 or PD0332991, which can be used as a therapeutic for AR-related diseases. This includes AR-related diseases wherein AR comprises a F877 mutation. In addition, PD0332991, LEE011 and other CDK4/6 inhibitors are useful as therapeutics against AR-related diseases wherein AR is wild-type. AR polypeptides with the F877 mutation, antibodies to them and polynucleotides encoding them are also useful for screening for novel therapeutics. In addition, in various aspects, the present disclosure pertains to a double mutation in AR at positions W742 and T878 (also numbered in accordance with the sequence of SEQ ID NO: 1), which this disclosure shows also confers resistance to MDV3100.

Mutant Androgen Receptor (AR) Polypeptide

In various aspects, the present disclosure pertains to AR(F877), which is a polypeptide or the like comprising Androgen Receptor or a fragment or variant thereof comprising or spanning position 877, wherein the amino acid at position 877 is substituted or deleted or is other than phenylalanine (F) (wherein the position of the amino acids is in accordance with the numbering of SEQ ID NO: 54). In some aspects, the amino acid at position 877 is substituted or deleted. In some aspects, the amino acid at position 877 is leucine (L). In various aspects, the AR(F877) polypeptide or fragment or variant thereof optionally comprises one or more mutations at other positions, such that the amino acid at position 878 is not threonine (T), the amino acid at position 875 is not histidine (H), the amino acid at position 716 is not valine (V), and/or the amino acid at position 742 is not tryptophan (W).

In various embodiments, the fragment is at least 5, at least 6, at least 7, at least 8, at least 9, at least 10, at least 15, at least 20, at least 25, at least 30, at least 35, at least 40, at least 50, at least 60, at least 75, at least 100, or at least 150, at least 200, at least 250, at least 300, at least 350, at least 400, at least 450, at least 500, at least 550, at least 600, at least 650, at least 700, at least 750, at least 800, at least 850, and/or at least 900 amino acids long. In various embodiments, the AR(F877) fragment or variant retains at least one activity of wild-type (or "WT") AR, which lacks a mutation at F877, or AR(F877).

In one aspect, the present disclosure provides isolated AR(F877) polypeptides having the sequence recited in SEQ ID NO: 54, or a variant thereof that differs in one or more amino acid deletions, additions, insertions or substitutions at no more than 50% of the residues in SEQ ID NO: 54, such that the polypeptide retains at least one activity of AR(F877).

In one aspect, the present disclosure provides isolated AR(F877) polypeptides having the sequence recited in SEQ ID NO: 54, or a variant thereof that differs in one or more amino acid deletions, additions, insertions or substitutions at no more than 1, 2, 3, 4, 5, 6, 7, 8, 9, 10, 15, 20, 25, 30, 35, 40, 45 or 50% of the residues in SEQ ID NO: 54, such that the polypeptide retains at least one activity of AR(F877).

Another embodiment of the disclosure provides an isolated polypeptide as described above, wherein the fragment comprises at least 10 contiguous amino acids of SEQ ID NO: 54.

Another embodiment of the disclosure provides an isolated polypeptide as described above, wherein the fragment comprises at least 15 contiguous amino acids of SEQ ID NO: 54.

Another embodiment of the disclosure provides an isolated polypeptide comprising a mutant Androgen Receptor or fragment thereof, wherein the amino acid sequence of the mutant Androgen receptor is shown in SEQ ID NO: 54, wherein said sequence contains a mutation at or spans amino acid position 877 of SEQ ID NO: 54 such that the amino acid at position 877 is substituted or deleted or is not phenylanine (F), wherein optionally the amino acid at position 878 is not threonine (T), the amino acid at position 875 is not histidine (H), the amino acid at position 716 is not valine (V), and/or the amino acid at position at 742 is not tryptophan (W), and wherein the sequence of the fragment comprises at least 5 contiguous amino acids of SEQ ID NO: 54 and comprises position 877.

Another embodiment of the disclosure provides an isolated polypeptide as described above, wherein the fragment comprises at least 10 contiguous amino acids of SEQ ID NO: 54.

Another embodiment of the disclosure provides an isolated polypeptide as described above, wherein the fragment comprises at least 15 contiguous amino acids of SEQ ID NO: 54.

In various aspects, the present disclosure pertains to AR(F877), which is a polypeptide or the like comprising Androgen Receptor or a fragment thereof comprising position 877, wherein the amino acid at position 877 is an amino acid other than phenylalaline (F).

Thus, in various aspects, the present disclosure pertains to various polypeptides comprising AR with mutation at position F877 (optionally with one or more mutations at other positions) or fragments or variants thereof comprising or spanning position F877, wherein the polypeptide, fragment or variant retains at least one activity of AR with a mutation at position.

Methods of Detecting AR(F877) and Stratifying Patients

Within further aspects, the present disclosure provides methods of detecting the presence or absence of a mutation at position F877 in AR in a sample in or from a patient. The mutation at F877 in AR is clinically relevant, as patients presenting such a mutant AR should not be treated with MDV3100, but rather should be treated with a treatment which does not comprise MDV3100 (e.g., bicalutamide or a CDK4/6 inhibitor such as LEE011 or PD0332991). It is also noted that CDK4/6 inhibitors (e.g., LEE011 and PD0332991) are also effective in methods of treatment of AR-related diseases wherein the AR is wild-type. Response to CDK4/6 inhibition was not only limited to F877L-bearing cells as androgen-independent 22Rv1 cells—a PCa line expressing WT AR and capable of maintaining AR signaling and expression of DHFR and TK1 under MDV3100 treatment conditions also showed strong sensitivity to CDK4/6 inhibition. These data cumulatively suggest that targeting CDK4/6 function may serve as an effective strategy for treatment of multiple mechanisms of resistance to MDV3100 and likely androgen-independence in general.

It is noted that the cells within a sample may be heterogeneous; some may express AR(F877), while others may express WT (wild-type) AR and/or other mutant AR. In various aspects described herein, the present disclosure pertains to methods of detecting a mutation at position F877 in AR of a sample which may comprise a mixture of AR(F877), WT AR and/or other mutant ARs.

In various aspects, the present disclosure provides a method of detecting a mutation at position F877 in an AR polynucleotide or polypeptide in a sample from a patient, the method comprising the steps of: (a) obtaining a sample comprising AR from the patient; and (b) determining the sequence of the AR polynucleotide or polypeptide or a portion thereof to determine if the AR comprises a mutation at position F877. The method optionally pertains to diagnosing, prognosing and/or treating a patient and optionally further comprises the additional step: (c) administering or recommending the administration of a therapeutic composition comprising MDV3100 if a AR does not comprise a mutation at F877; or administering or recommending the administration of a therapeutic composition not comprising MDV3100 if a AR does comprise a mutation at F877. In various aspects, the therapeutic composition not comprising MDV3100 is bicalutatmide or a CDK4/6 inhibitor such as LEE011 or PD0332991, or a therapeutic nucleic acid. In various aspects, if the sample is determined to comprise a mixture of cells expressing AR(F877), WT AR and/or other mutant ARs, several steps may be necessary to attack the different types of cells within the mixture. In addition, ratios of WT and various mutant AR-presenting cells may change as sub-populations of cells are killed off or possibly activated by therapies, and resistant clones arise. Thus, steps (a), (b) and (c) may be repeated.

In various aspects, the method of determining if the amino acid at position 877 in AR is phenylalanine (F) includes without limitation and inter alia, use of nucleic acid sequencing, or using an antibody or nucleic acid specific to AR(F877).

Within still other aspects, the present disclosure provides a method for detecting AR(F877) expression in a sample, comprising: (a) contacting a sample with a nucleic acid or fragment or variant thereof specific to AR(F877) under conditions and for a time sufficient to allow hybridization of the nucleic acid with a nucleic acid in the sample; and (b) detecting the level of hybridization Also provided are methods for modulating a proliferative response in a cell, comprising the step of contacting a cell with an agent that modulates AR(F877) activity.

Within further aspects, methods are provided for modulating differentiation of a cell, comprising the step of contacting a cell with an agent that modulates AR(F877) activity.

The present disclosure further provides methods for modulating cell survival, comprising the step of contacting a cell with an agent that modulates AR(F877) activity.

Thus, in various aspects, the present disclosure pertains to various methods of detecting or AR(F877) and stratifying patients who do or do not express this polypeptide.

In one aspect, the disclosure pertains to a method of determining the sensitivity of a cell to MDV3100, the method comprising: (a) determining the amino acid, if any, at position 877 in Androgen Receptor in the cell, wherein the position 877 is determined in accordance to the numbering of SEQ ID NO: 54; (b) comparing the amino acid, if any, at position 877 to a wild-type Androgen Receptor, wherein the absence of an amino acid or the presence of an amino acid other than phenylalanine indicates that the cell is not sensitive to MDV3100. In one aspect, the cell is a prostate cancer cell, breast cancer cell, or other AR-related disease cell. In one aspect, the AR-related disease is polyglutamate disease, alopecia, benign prostatic hyperplasia, hirsutism, acne, spinal and muscular atrophy or Kennedy disease.

In one aspect, the disclosure pertains to a method of predicting the sensitivity of a patient of an AR-related disease to treatment with MDV3100, the method comprising: (a) determining the amino acid, if any, at position 877 in Androgen Receptor in the sample in or obtained from the patient, wherein the position 877 is determined in accordance to the numbering of SEQ ID NO: 54; (b) comparing the amino acid, if any, at position 877 to a wild-type Androgen Receptor, wherein the absence of an amino acid or the presence of an amino acid other than phenylalanine indicates that the patient is not sensitive to MDV3100. In one aspect, the AR-related disease is prostate or breast cancer. In one aspect, the AR-related disease is polyglutamate disease, alopecia, benign prostatic hyperplasia, hirsutism, acne, spinal and muscular atrophy or Kennedy disease.

In one aspect, the disclosure pertains to a method of treating a patient with an AR-related disease, the method comprising: (a) determining the amino acid, if any, at position 877 in Androgen Receptor in the sample in or obtained from the patient, wherein the position 877 is determined in accordance to the numbering of SEQ ID NO: 54; (b) comparing the amino acid, if any, at position 877 to a wild-type Androgen Receptor, wherein the absence of an amino acid or the presence of an amino acid other than phenylalanine indicates that the patient is not sensitive to MDV3100; (c) if the amino acid at position of 877 is not phenylalanine, administering a treatment which does not comprise MDV3100; or if the amino acid at position 877 is phenylalanine, administering a treatment which comprises MDV3100; and (d) assaying for disease progression or palliation. In one aspect, the AR-related disease is prostate or breast cancer. In one aspect, the AR-related disease is polyglutamate disease, alopecia, benign prostatic hyperplasia, hirsutism, acne, spinal and muscular atrophy or Kennedy disease.

Methods of Detecting AR(W742/T878) and Stratifying Patients

Within further aspects, the present disclosure also pertains to the double mutation at positions W742 and T878; methods of detecting this double mutation in a sample from a patient; and methods of stratifying patients, as patients presenting this double mutation should not be treated with MDV3100 or bicalutamide, but rather should be treated with a treatment which does not comprise MDV3100 or bicalutamide.

In various aspects, the present disclosure provides a method for detecting AR(W742/T878) expression in a patient), the method comprising the step of: determining if the amino acids at positions 742 and 878 of an androgen receptor or fragment thereof in the patient are, respectively, tryptophan (W) and threonine (T). In various aspects, the method further comprises the steps of recommending the administration of and/or administering to the patient: (a) bicalutamide or MDV3100 if the amino acids at positions 742 and 878 are, respectively, tryptophan (W) and threonine (T); or (b) a prostate disease treatment other than bicalutamide or MDV3100 if the amino acids at positions 742 and 878 are not, respectively, tryptophan (W) and threonine (T). The treatment that does not comprise bicalutamide or MDV3100 can comprise, as non-limiting examples, another therapeutic, such as a CDK4/6 inhibitor such as LEE011 or PD0332991, or a therapeutic nucleic acid.

In various aspects, the present disclosure provides a method of diagnosing, prognosing and/or treating a patient having or suspected of having an AR-related disease, comprising the steps of: obtaining from the patient a biological sample compressing a cell expressing androgen receptor; determining if the androgen receptor comprises a double mutation at positions 742 and 878 such that the amino acid at position 742 is not tryptophan (W) and the amino acid at position 878 is not threonine (T), and either: treating the patient with a treatment comprising bicalutamide or MDV3100 if the androgen receptor comprises a tryptophan (W) at amino acid position 742 and a threonine (T) at position 878, or treating the patient with a treatment for prostate disease that does not comprise bicalutamide or MDV3100 if the androgen receptor comprises an amino acid other than tryptophan (W) at amino acid position 742 and an amino acid other than threonine (T) at amino acid position 878. The treatment that does not comprise bicalutamide or MDV3100 can comprise, as non-limiting examples, another therapeutic, such as a CDK4/6 inhibitor such as LEE011 or PD0332991, or a therapeutic nucleic acid. This disclosure also notes that a CDK4/6 inhibitor can also be used in a method of treatment of AR-related diseases wherein the AR is wild-type. It is also noted that a combination therapy comprising multiple agents and/or therapies can be used in treatment of AR-related diseases (e.g., bicalutamide and/or LEE011 and/or PD0332991 and/or other treatments known in the art).

In one aspect, the disclosure pertains to a method of determining the sensitivity of a cell to MDV3100, the method comprising: (a) determining the amino acid, if any, at positions 742 and 878 in Androgen Receptor in the cell, wherein the positions 742 and 878 is determined in accordance to the numbering of SEQ ID NO: 54; (b) comparing the amino acid, if any, at positions 742 and 878 to a wild-type Androgen Receptor, wherein the absence of an amino acid or the presence of an amino acid other than Tryptophan (W) at position 742 and the absence of an amino acid or the presence of an amino acid other than Threonine (T) at position 878 together indicate that the cell is not sensitive to MDV3100. In one aspect, the cell is a prostate cancer cell, breast cancer cell, or other AR-related disease cell. In one aspect, the AR-related disease is polyglutamate disease, alopecia, benign prostatic hyperplasia, hirsutism, acne, spinal and muscular atrophy or Kennedy disease.

In one aspect, the disclosure pertains to a method of predicting the sensitivity of a patient of an AR-related disease to treatment with MDV3100, the method comprising: (a) determining the amino acid, if any, at positions 742 and 878 in Androgen Receptor in the sample in or obtained from the patient, wherein the positions 742 and 878 is determined in accordance to the numbering of SEQ ID NO: 54; (b) comparing the amino acid, if any, at positions 742 and 878 to a wild-type Androgen Receptor, wherein the absence of an amino acid or the presence of an amino acid other than Tryptophan (W) at position 742 and the absence of an amino acid or the presence of an amino acid other than Threonine (T) at position 878 together indicate that the patient is not sensitive to MDV3100. In one aspect, the AR-related disease is prostate or breast cancer. In one aspect, the AR-related disease is polyglutamate disease, alopecia, benign prostatic hyperplasia, hirsutism, acne, spinal and muscular atrophy or Kennedy disease.

In one aspect, the disclosure pertains to a method of treating a patient with an AR-related disease, the method comprising: (a) determining the amino acid, if any, at positions 742 and 877 in Androgen Receptor in the sample in or obtained from the patient, wherein the positions 742 and 877 is determined in accordance to the numbering of SEQ ID NO: 54; (b) comparing the amino acid, if any, at positions 742 and 878 to a wild-type Androgen Receptor, wherein the absence of an amino acid or the presence of an amino acid other than Tryptophan (W) at position 742 and the absence of an amino acid or the presence of an amino acid other than Threonine (T) at position 878 together indicate that the patient is not sensitive to MDV3100; (c) if the amino acid at position of 878 is not phenylalanine, administering a treatment which does not comprise MDV3100; or if the amino acid at positions 742 and 878 is phenylalanine, administering a treatment which comprises MDV3100; and (d) assaying for disease progression or palliation. In one aspect, the AR-related disease is prostate or breast cancer. In one aspect, the AR-related disease is polyglutamate disease, alopecia, benign prostatic hyperplasia, hirsutism, acne, spinal and muscular atrophy or Kennedy disease.

Thus, in various aspects, the present disclosure pertains to various methods of detecting or AR(W742/T878) and stratifying patients who do or do not express this polypeptide.

Screening for Novel Therapeutics

The mutation at position F877 allows AR to be resistant to MDV3100, and even causes an antagonist-to-agonist switch for this drug. There thus exists the need for novel therapeutics which interact with AR(F877) and are useful for treating patients of AR-related diseases who have such a mutation in AR.

The present disclosure further provides, within other aspects, methods for screening a molecule (e.g., a potential therapeutic) for the ability to interact with AR(F877), comprising the steps of: (a) contacting a candidate molecule with a AR(F877) polypeptide under conditions and for a time sufficient to permit the candidate molecule and polypeptide to interact; and (b) detecting the presence or absence of binding of the candidate molecule to the polypeptide and/or ability to interfere with or decrease at least one activity of the polypeptide. The step of detecting may, for example, comprise the use of an AR(F877) and an AR reporter, e.g., a polynucleotide comprising an ARE [DNA sequence to which WT or AT(F877) bind], promoter, and a reporter gene (e.g., luciferase). The step of detecting may comprise, for example, determining if the candidate molecule interferes with or decreases the ability of the AR(F877) to drive expression from the AR reporter. The step of detecting may comprise, for example, an affinity purification step, a yeast two hybrid screen or a screen of a phage display library.

In some aspects, the methods of screening for novel therapeutics involve the use of an AR(F877) polypeptide or fragment or variant thereof comprising or spanning the amino acid at position 877. This polypeptide can be produced in any manner known in the art, including expression from a polynucleotide encoding the polypeptide.

The present disclosure encompasses methods of producing a AR(F877) polypeptide.

The present disclosure further provides, within other aspects, methods for producing a AR(F877) polypeptide, comprising the steps of: (a) culturing a host cell as described above under conditions that permit expression of the AR(F877) polypeptide; and (b) isolating AR(F877) polypeptide from the host cell culture.

The present disclosure thus pertains, in various aspects, to compositions and methods for screening and developing new therapeutics, including polypeptides comprising, antibodies to polypeptides comprising, and polynucleotides encoding AR(F877).

Methods of Treatment

In various embodiments, the present disclosure pertains to methods of treatment of AR-related diseases, wherein the AR has a mutation described herein.

In one embodiment, the present disclosure pertains to a method of treating a patient with an Androgen Receptor (AR)-related disease, wherein the amino acid at position of 877 of AR is absent or is not phenylalanine, and wherein the method comprises the step of administering a therapeutic composition which does not comprise MDV3100.

In various embodiments, the therapeutic composition not comprising MDV3100 comprises bicalutatmide or a CDK4/6 inhibitor such as LEE011 or PD0332991, or a therapeutic nucleic acid.

In one embodiment, the present disclosure pertains to a method of treating a patient with an Androgen Receptor (AR)-related disease, wherein the amino acids at positions 742 and 878 of AR are phenylalanine, and wherein the method comprises the step of administering a therapeutic composition which comprises MDV3100.

In one embodiment, the present disclosure pertains to a method of treating a patient with an Androgen Receptor (AR)-related disease, wherein the amino acid at position of 877 of AR is absent or is not phenylalanine, and wherein the method comprises the step of administering a therapeutic composition which comprises a CDK4/6 inhibitor.

In various embodiments, the CDK4/6 inhibitor is LEE011 or PD0332991.

In various embodiments, the AR-related disease is prostate or breast cancer. In various embodiments, the AR-related disease is polyglutamate disease, alopecia, benign prostatic hyperplasia, hirsutism, acne, spinal and muscular atrophy or Kennedy disease.

AR(F877) Polynucleotide

In another aspect, the present disclosure provides a polynucleotide or an antisense polynucleotide that comprises at least 15 consecutive nucleotides (including 0, 1, 2 or 3 mismatches) having the sequence of and/or capable of detectably hybridizing to a sequence encoding at least 5 contiguous amino acids of SEQ ID NO: 54, including position 877, wherein the amino acid at position 877 is substituted or deleted and is an amino acid other than phenylalanine (F), wherein hybridization is under conditions that include a wash. These polynucleotides can be used to encode (e.g., express) a AR(F877) polypeptide, or incorporated into a therapeutic nucleic acid [e.g., a siRNA or the like to AR(F877)].

Another embodiment of the disclosure provides an isolated Androgen Receptor polynucleotide, wherein the isolated polynucleotide or its complement encodes at least 5, 6, 7, 8, 9, 10, 11, 12, 13, 14 or 15 contiguous amino acids of SEQ ID NO: 2, wherein the at least 5, 6, 7, 8, 9, 10, 11, 12, 13, 14 or 15 contiguous amino acids comprise or span position 877 of SEQ ID NO: 2, and wherein the amino acid at position 877 is not Phenylalanine (F), and wherein, optionally, the amino acid at position 878 is not threonine (T), the amino acid at 875 is not histidine (H), the amino acid at position 716 is not valine (V), and/or the amino acid at position at 742 is not tryptophan (W).

Another embodiment of the disclosure provides an expression construct (or vector) comprising an isolated Androgen Receptor polynucleotide as described above.

Another embodiment of the disclosure provides a host cell comprising an isolated Androgen Receptor polynucleotide as described above.

Another embodiment of the disclosure provides a polynucleotide which encodes a mutant Androgen receptor comprising an amino acid sequence of SEQ ID NO: 2 except the encoded mutant Androgen receptor protein contains an leucine (L) at position 877 of SEQ ID NO: 2.

Another embodiment of the disclosure provides a construct comprising: a promoter; and a polynucleotide segment encoding a mutant Androgen receptor or a fragment thereof, wherein the amino acid sequence of the Androgen Receptor is shown in SEQ ID NO: 2, wherein said sequence contains a mutation at amino acid position 877 of SEQ ID NO: 2 such that the amino acid at position 877 is not phenylanine (F), and wherein, optionally, the amino acid at position 878 is not threonine (T), the amino acid at 875 is not histidine (H), the amino acid at position 716 is not valine (V), and/or the amino acid at position at 742 is not tryptophan (W), and wherein the sequence of the fragment comprises at least 5 contiguous amino acids of SEQ ID NO: 2 and comprises position 877, wherein the polynucleotide segment is located downstream from the promoter, wherein transcription of the polynucleotide segment initiates at the promoter.

Another embodiment of the disclosure provides an isolated polynucleotide wherein the isolated polynucleotide or its complement encodes at least 10, 15 or 20 contiguous amino acids of SEQ ID NO: 54, wherein the at least 10 contiguous amino acids comprise position 877 of SEQ ID NO: 54, and wherein the amino acid at position 877 is substituted or deleted or is not Phenylalanine (F).

Another embodiment of the disclosure provides a host cell comprising a construct which comprises a promoter; and any polynucleotide as described herein.

Thus, in various aspects, the present disclosure pertains to a polynucleotide encoding an AR(F877) or fragment or variant thereof.

These and other aspects of the present disclosure will become apparent upon reference to the following detailed description and attached drawings. All references disclosed herein are hereby incorporated by reference in their entirety as if each is incorporated individually.

DETAILED DESCRIPTION OF THE INVENTION

Figure 1A:
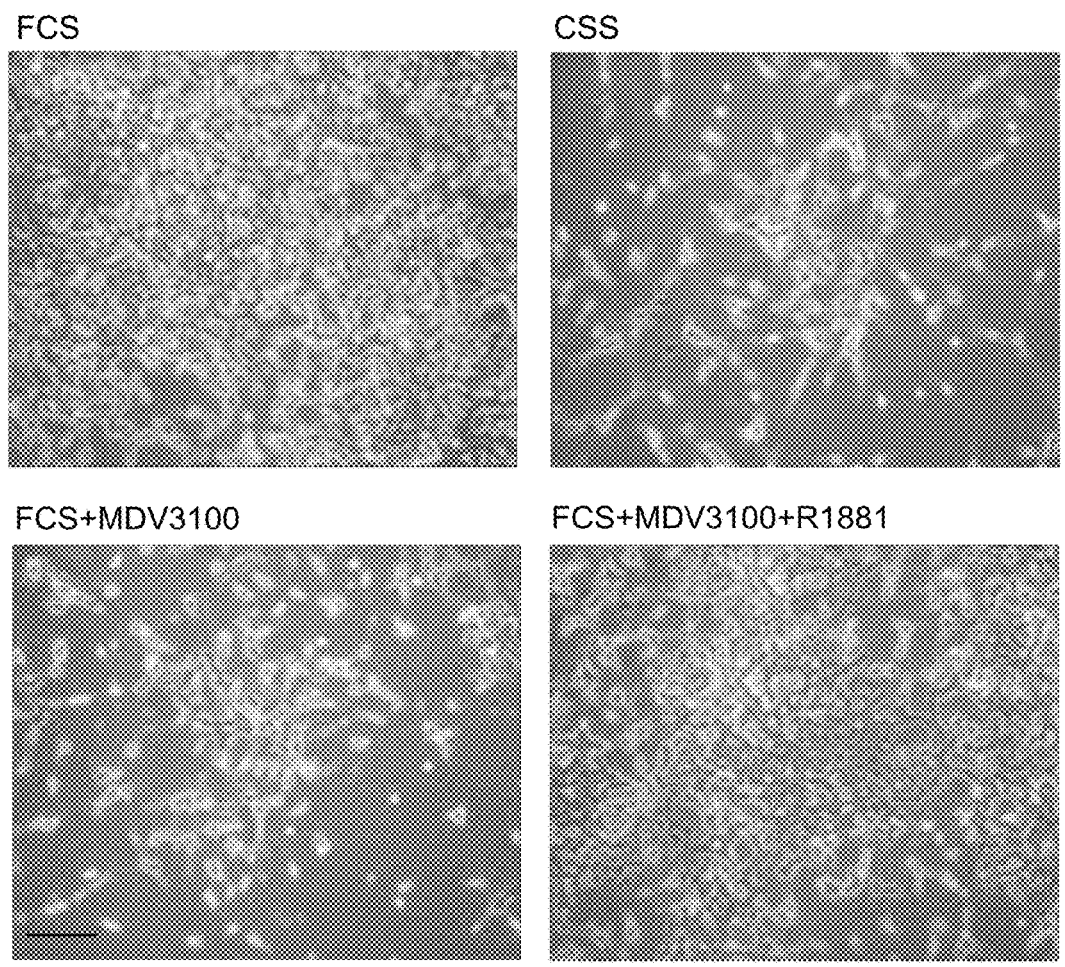
FIG. 1. Characterization of MDV3100-resistant clones derived from LNCaP cells. A, phase contrast images of LNCaP cells grown in RPMI media supplemented with 10% FCS (upper left), 10% CSS (upper right), 10% FCS+1 μM MDV3100 (lower left) and 10% FCS+1 μM MDV3100+1 nM R1881 (lower right). Scale bar, 50 μM. B, schematic representation of the experimental paradigm applied (see main text for details). C, individual (left) and average (right) growth inhibition curves for the three controls (brown line) and seven resistant clones (green and red) treated with MDV3100 (top) and bicalutamide (bottom). Data presented as percent growth relative to DMSO treatment condition as measured by CellTiter-Glo assay. D, western blot analysis of AR expression in control and resistant lines. β-actin used as loading control. E, AR pathway activity scores for C1-C3 and seven resistant clones grown in 10% FCS at baseline (following drug withdrawal for 2 weeks) (beige bars). Scores also calculated for C1-C3 treated with 10 μM MDV3100 for 24 h as reference (green bars). Genes upregulated by androgens were used for analysis.

The present disclosure pertains to Androgen Receptor (AR)-related diseases. The present disclosure pertains to a novel and clinically relevant mutation at position F877 in Androgen Receptor, which confers resistance to the drug MDV3100 and is useful for patient stratification. Androgen receptor and fragments and variants thereof comprising this mutation [AR(F877)] are also useful for devising new treatments that target this mutant receptor. In addition, the double-mutant AR at positions W742 and T878 and fragments and variants thereof comprising this double mutation [AR(W742/T878)] are also resistant to MDV3100 and useful for patient stratification. This disclosure thus has utility in prognosis, diagnosis and treatment of AR-related diseases, such as prostate diseases, such as prostate cancer (PCa), including castration-resistant Pca (CRPC), and breast cancer, as well as other disorders such as polyglutamate disease, alopecia, benign prostatic hyperplasia, hirsutism, acne, spinal and muscular atrophy and Kennedy disease.

Despite prostate cancer being one of the most commonly diagnosed cancers in the world, scientists are plagued with limited knowledge, resources and analytical methods that hamper 1) reliable diagnosis of prostate cancer, 2) the ability to distinguish benign from life-threatening disease, and 3) the ability to efficiently treat patients that have relapsed on androgen-deprivation therapies. Androgen-deprivation therapies, including chemical and surgical castration, are initially effective in treating androgen-dependent PCa. However, most tumors relapse as a much more aggressive and incurable form of PCa referred to as castration-resistant PCa (CRPC). The malignant nature of CRPC has prompted an aggressive campaign to expedite development of effective therapeutics that can be used as second-line therapies to improve survival rates of CRPC patients. To this end, antagonists that compete with androgen for binding to AR have been developed, based on the knowledge that CRPCs continue to rely on AR-signaling for survival. Success here has been marginal due to 1) lack of potency of compounds, and 2) CRPC adapting by promoting an antagonist-to-agonist switch such that the compound paradoxically enhances AR signaling. To circumvent these limitations, a more potent antagonist, MDV3100 (enzalutamide), has recently been approved by the FDA for treatment of men with metastatic CRPC previously treated with docetaxel. In some cases, MDV3100 may be used as a monotherapy, even with castration-resistant prostate cancer. Although the compound has shown tremendous efficacy in clinical trials, many patients who initially responded have since developed resistance. A mechanistic understanding of resistance is lacking and this a priori knowledge is critical to designing alternate treatment strategies. To this end, this disclosure presents the identification and characterization of a novel mutation in AR—the direct target of MDV3100—that genetically and phenotypically confers resistance to MDV3100.

To elucidate mechanisms of resistance, this disclosure uses LNCaPs—a model previously used to identify a clinically relevant W742C mutation that confers resistance to bicalutamide—to establish a spontaneous resistance model specific for MDV3100. Two broad classes of resistant clones were identified; those showing either sensitivity or resistance to AR pathway modulation upon MDV3100 treatment. Excitingly, RNA-seq analysis identified a novel F877L/T878A mutation in AR that correlated with resistance to pathway modulation by MDV3100. Transactivation assays coupled with analysis of genetically engineered lines confirmed that the mutation promoted an antagonist-to-agonist switch for MDV3100—ultimately translating to phenotypic resistance. Interestingly, this disclosure finds that this mutation is highly selective for MDV3100, as treatment with bicalutamide, an older anti-androgen, sensitizes the cells once again. These findings are likely to have tremendous clinical impact as the 1) mutation can be used as a biomarker to predict drug response, and 2) patients presenting the F877L/T878A mutation can readily be treated with bicalutamide to achieve clinical benefit.

Unexpectedly, this disclosure also found that a previously identified W742C/T878A mutation (previously shown to confer resistance to bicalutamide) can also partially confer phenotypic resistance to MDV3100. Without wishing to be bound by any particular theory, this disclosure speculates that this is likely to be an indirect effect as the double mutant AR gains a constitutive active function. Regardless, this finding is likely to have a translational impact as patients presenting this mutation will be unlikely to benefit from anti-androgen therapies. Furthermore, our work highlights the importance of screening other well-characterized mutations in prostate cancer to determine their potential for conferring resistance to MDV3100—mutations such as H875Y, V716M, and L701H/T878A have been shown to possess a broadened spectrum of ligand responsiveness, and hydroxyflutamide has previously been shown to work as an agonist for these mutants.

The findings from the current disclosure will likely set the stage for expedited discovery of driver mutations for various pathological states that will ultimately impact the development and implementation of therapeutic strategies. This disclosure makes the following contributions: 1) by coupling high throughput RNA-seq technology with a model of spontaneous resistance, this disclosure identified a novel mutation in AR that genetically and phenotypically confers resistance to MDV3100—and yet retains sensitivity to bicalutamide. This will aid in patient stratification and development of alternate treatment strategies. 2) Our spontaneous lines represent at least two independent modes of resistance—a resource that will be of great value to the PCa community for further interrogation into the resistance mechanisms. 3) This disclosure shows that a conserved feature of resistant mutations in the ligand-binding pocket of AR is to confer an antagonist-to-agonist switch, unlike other classes of compounds. Compositions comprising an AR(877) can also be used to generate antibodies to this polypeptide, and can be used to generate novel therapeutics which target this polypeptide and are useful in treating androgen receptor-related diseases, including, inter alia, prostate and breast cancer.

Targeting CDK4/6 as a Therapeutic Strategy for Overcoming MDV3100 Resistance

Figure 6A:
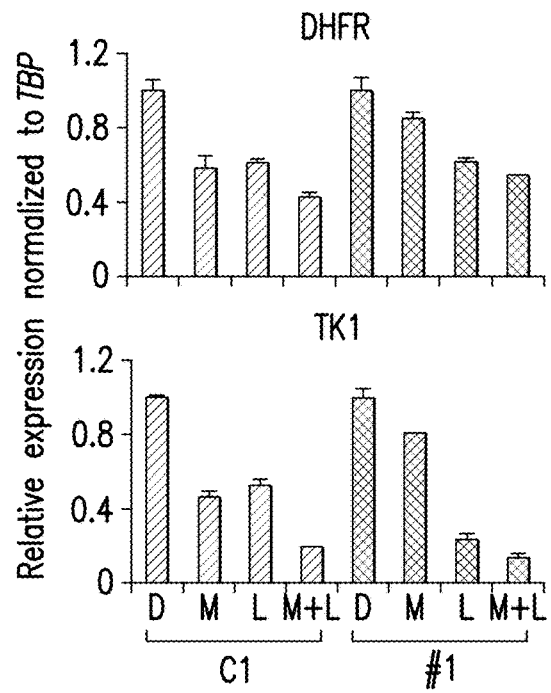
FIG. 6. Targeting CDK4/6 reduces proliferation of MDV3100-resistant prostate cancer cell lines. A, qPCR analysis of E2F1 targets DHFR and TKJ in C1 and clone #1 lines upon treatment with DMSO (D), 10 μM MDV3100 (M), 10 μM LEE011 (L) or 10 μM MDV3100 and 10 μM LEE011 (M+L) for 24 h. B, average growth inhibition curves for the three controls (brown line) and seven resistant clones (green and red) treated with PD033299 (top) and LEE011 (bottom). Data presented as percent growth relative to DMSO treatment condition as measured by CellTiter-Glo assay. C, relative quantitation of data from colony formation assays of AR-T878A and AR-F877L/T878A lines treated with DMSO, 10 μM MDV3100 (MDV), 10 μM bicalutamide (Bic) or 10 μM LEE011 (LEE) for 28 d (quantitated by Image J). D, qPCR analysis of E2F1 targets DHFR and TKJ in androgen-independent 22Rv1 line treated with DMSO, 10 μM MDV3100 (MDV), 10 μM LEE011 (LEE) or 10 μM MDV3100 and 10 μM LEE011 (MDV+LEE) for 48 h. E, colony formation assays of 22Rv1 cells treated with various indicated compounds (DMSO, bicalutamide (Bic), MDV3100 (MDV) or LEE011 (LEE)) for 14 d.
Figure 6B:
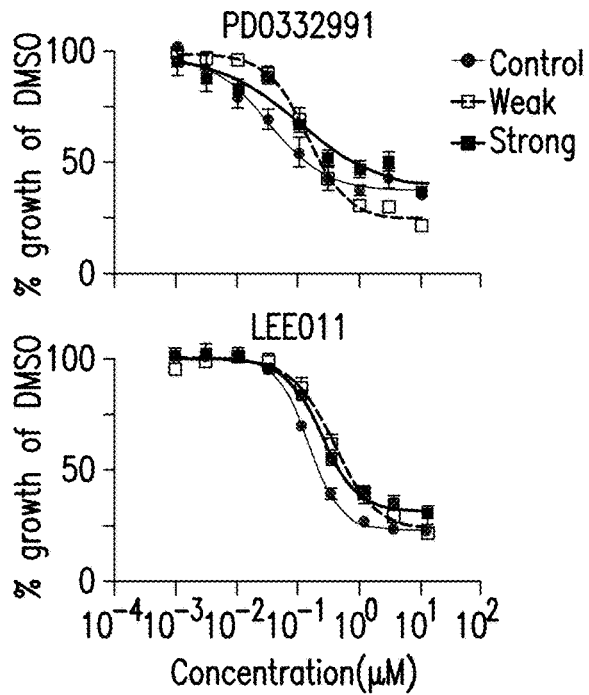
Figure 6C:
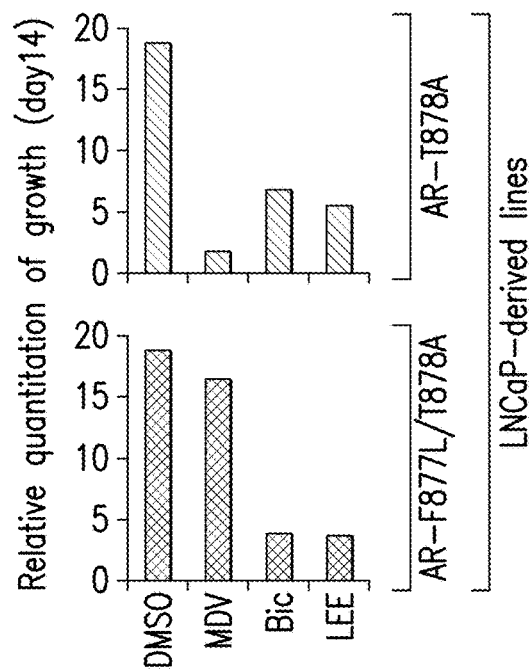
Figure 6D:
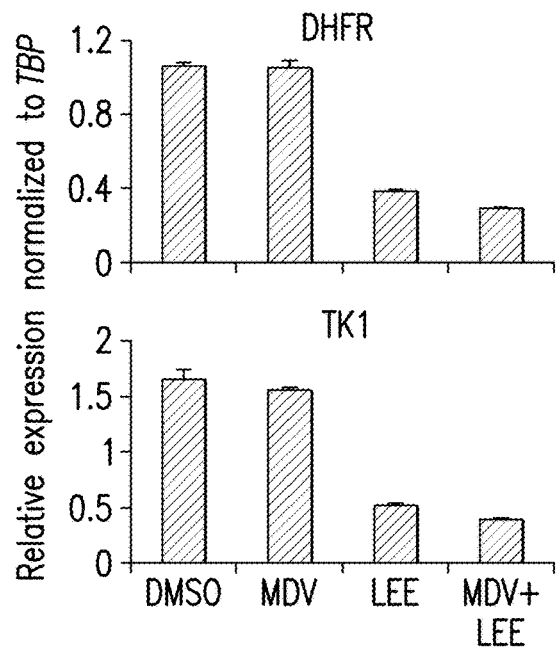
Figure 6E:
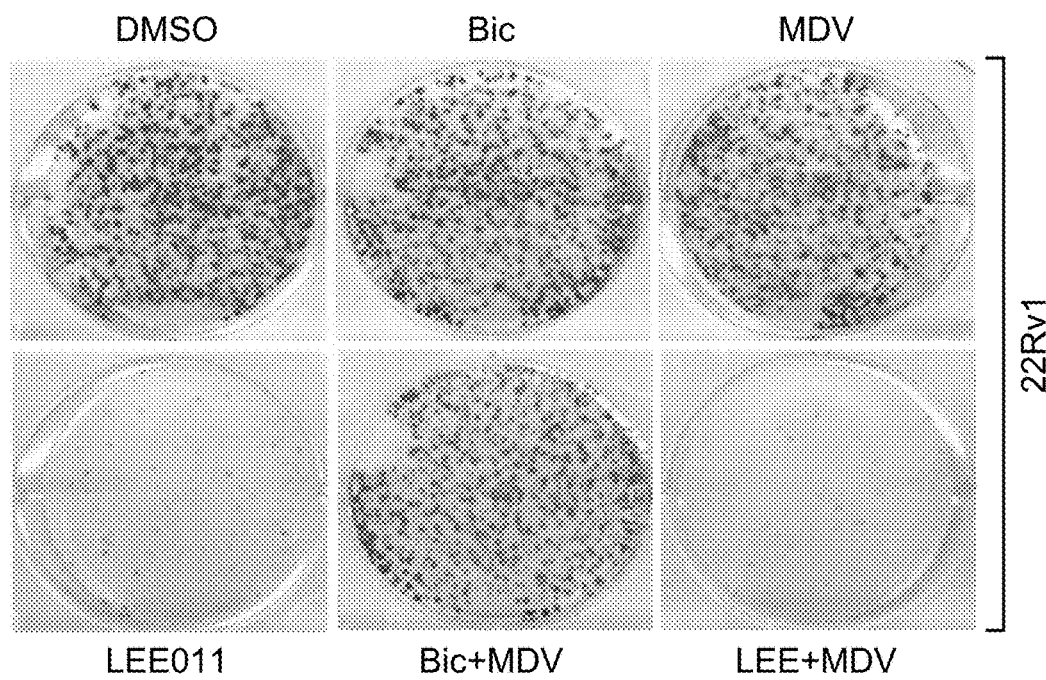
Figure 14:
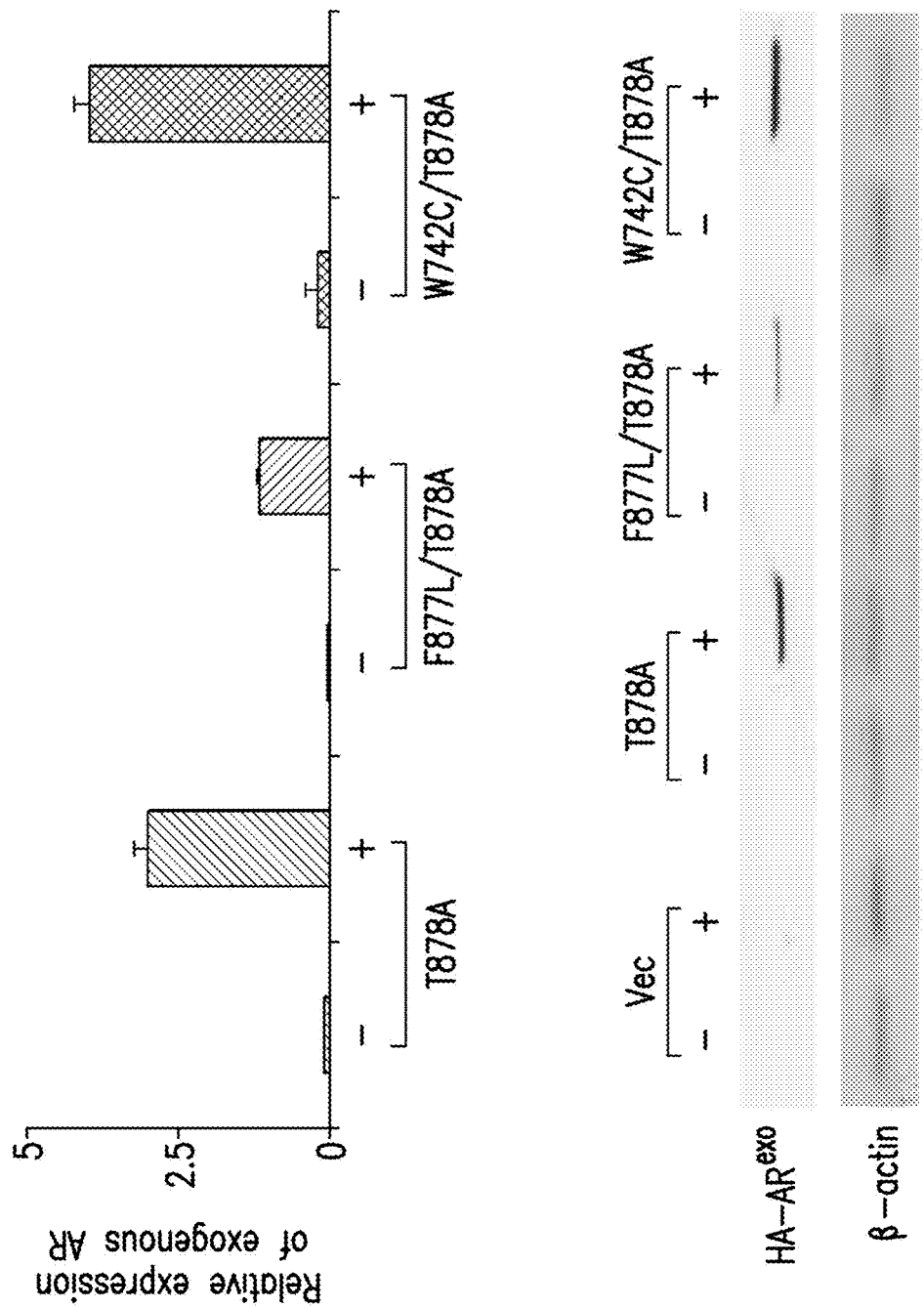
FIG. 14. LNCaPs engineered to inducibly express T878A (red bars), F877L/T878A (green bars) or W742C/T878A (blue bars) AR show modest overexpression as assessed by both qPCR (top) and western analysis (bottom). −/+, untreated or treated with Dox respectively. TBP and β-actin were used as loading controls for qPCR and western analysis, respectively. Data represent mean±SEM.

Having established that AR-F877L can promote resistance to MDV3100 under various genetic contexts in vitro and in vivo, we next aimed to develop rational strategies to antagonize the mutant allele. As an alternative to developing novel anti-androgens that continue to target the hypermutable ligand-binding pocket of AR [Balbas et al. 2013 eLife 2:e00499], we aimed to identify therapeutic strategies that may be more sustainable in the clinic. To this end, we observed a significant enrichment for genes belonging to 'cell cycle' and 'E2F1 activation' gene sets in addition to 'AR activation' in strongly resistant clones treated with MDV3100, suggesting that these clones may potentially maintain proliferation under MDV3100-treatment conditions through continued expression of E2F1 target genes. This is an appealing hypothesis as androgen signaling, a critical regulator of G1-S transition, is known to promote active CDK4/cyclin D1 assembly and hence activation of E2F1 function. Schiewer et al. 2012 End. Relat. Cancer 9: 1-12. Consistent with this notion, we observed that MDV3100-treatment suppressed expression of E2F1 target genes DHFR and TK1 in a control line, confirming AR signaling as a regulator of E2F1 function. In contrast, F877L-bearing cells were capable of maintaining higher expression of DHFR and TK1 under MDV3100-treatment conditions relative to a control line (FIG. 6A). Based on these data, we reasoned that E2F1 activity may serve as a downstream effector of AR signaling, and as such, regulators of E2F1 function may serve as critical therapeutic nodes when AR-directed therapies become ineffective. In agreement with this hypothesis, we found that growth of strongly resistant clones (FIG. 14) and LNCaP lines engineered to express AR-F877L/T878A (FIG. 6C) were as sensitive to CDK4/6 inhibitors LEE011 [Rader et al. 2013 CDK4/CDK6 inhibition is potently active in a definable subset of human neuroblastomas American Association for Cancer Research; Philadelphia, Pa.] and PD0332991, as bicalutamide. Interestingly, response to CDK4/6 inhibition was not only limited to F877L-bearing cells as androgen-independent 22Rv1 cells—a PCa line expressing WT AR and capable of maintaining AR signaling and expression of DHFR and TK1 under MDV3100 treatment conditions (FIG. 6D)—also showed strong sensitivity to CDK4/6 inhibition (FIG. 6E). These data cumulatively suggest that targeting CDK4/6 function may serve as an effective strategy for treatment of multiple mechanisms of resistance to MDV3100 and likely androgen-independence in general.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

Androgen Receptor

By "Androgen receptor" or "AR" is meant the gene or gene product (e.g., a polypeptide) also known as NR3C4 (nuclear receptor subfamily 3, group C, member 4) and also known by the symbols AR; AIS; DHTR; HUMARA; HYSP1; KD; NR3C4; SBMA; SMAX1; and TFM; and External IDs OMIM: 313700 MGI: 88064 HomoloGene: 28 IUPHAR: NR3C4 ChEMBL: 1871. A polypeptide and a nucleotide sequence of an example AR are shown in SEQ ID NO: 1 and 2, respectively. An example AR(F877) polypeptide sequence is shown in SEQ ID NO: 54.

Androgen receptor is a type of nuclear receptor [Lu et al. 2006 Pharmacol. Rev. 58: 782-97] that is activated by binding of either of the androgenic hormones testosterone or dihydrotestosterone [Roy et al. Vitam. Horm. 55: 309-52] in the cytoplasm and then translocating into the nucleus. The androgen receptor is most closely related to the progesterone receptor, and progestins in higher dosages can block the androgen receptor. Bardin et al. 1983 Pharm. Ther. 23: 443-59; and Raudrant et al. 2003 Drugs 63: 463-92. The main function of the androgen receptor is as a DNA-binding transcription factor that regulates gene expression [Mooradian et al. 1987 Endocr. Rev. 8: 1-28]; however, the androgen receptor has other functions as well [Heinlein et al. 2002. Mol. Endocrinol. 16: 2181-7]. Androgen regulated genes are critical for the development and maintenance of the male sexual phenotype.

The binding of androgen to the androgen receptor induces a conformational change to the receptor, resulting in a dissociation of heat shock proteins, dimerization and transport from the cytosol to the cell nucleus where the androgen receptor dimer binds to specific DNA sequences-referred to as hormone response elements or androgen response elements (ARE). Depending on the interaction with other nuclear proteins, the AR controls gene expression, either increasing or decreasing transcription of specific genes, such as insulin-like growth factor I (IGF-1).

Androgen receptors can also have cytoplasmic activities though with signal transduction proteins in the cytoplasm. Androgen binding to cytoplasmic androgen receptors, can cause rapid changes in cell function independent of gene transcription, for example ion transport, as well as indirect influence of gene transcription, for example via mediating other signal transduction pathways, thereby influencing the activity of other transcription factors.

Androgen Receptor Sequence and Mutations

The amino acid sequence of an example AR is shown below:

```
                                              (SEQ ID NO: 1)
MEVQLGLGRVYPRPPSKTYRGAFQNLFQSVREVIQNPGPRHPEAASAAPP

GASLLLLQQQQQQQQQQQQQQQQQQQQQQQQETSPRQQQQQQGEDGSPQAH

RRGPTGYLVLDEEQQPSQPQSALECHPERGCVPEPGAAVAASKGLPQQLP
```

APPDEDDSAAPSTLSLLGPTFPGLSSCSADLKDILSEASTMQLLQQQQQE

AVSEGSSSGRAREASGAPTSSKDNYLGGTSTISDNAKELCKAVSVSMGLG

VEALEHLSPGEQLRGDCMYAPLLGVPPAVRPTPCAPLAECKGSLLDDSAG

KSTEDTAEYSPFKGGYTKGLEGESLGCSGSAAAGSSGTLELPSTLSLYKS

GALDEAAAYQSRDYYNFPLALAGPPPPPPPPHPHARIKLENPLDYGSAWA

AAAAQCRYGDLASLHGAGAAGPGSGSPSAAASSSWHTLFTAEEGQLYGPC

GGGGGGGGGGGGGGGGGGGGGEAGAVAPYGYTRPPQGLAGQESDFTAP

DVWYPGGMVSRVPYPSPTCVKSEMGPWMDSYSGPYGDMRLETARDHVLPI

DYYFPPQKTCLICGDEASGCHYGALTCGSCKVFFKRAAEGKQKYLCASRN

DCTIDKFRRKNCPSCRLRKCYEAGMTLGARKLKKLGNLKLQEEGEASSTT

SPTEETTQKLTVSHIEGYECQPIFLNVLEAIEPGVVCAGHDNNQPDSFAA

LLSSLNELGERQLVHVVKWAKALPGFRNLHVDDQMAVIQYSWMGLMVFAM

GWRSFTNVNSRMLYFAPDLVFNEYRMHKSRMYSQCVRMRHLSQEFGWLQI

TPQEFLCMKALLLFSIIPVDGLKNQKFFDELRMNYIKELDRIIACKRKNP

TSCSRRFYQLTKLLDSVQPIARELHQFTFDLLIKSHMVSVDFPEMMAEII

SVQVPKILSGKVKPIYFHTQ

Several amino acids of note are underlined:
W 742, mutated to W742C/L in a number of bicalutamide resistant tumors.
H 875, mutated to H875Y in a number of prostate tumors.
F 877, shown herein to be mutated, e.g., to F877L. F877L single mutant and F877L/T878A double mutant ARs had a substantial transactivation response to MDV3100, suggesting an antagonist-to-agonist switch that is exquisitely specific for MDV3100.
T 877, mutated to T878A in a number of late stage and flutamide resistant tumors.

Additional mutations known to occur in AR include V 716 and others described herein and in the art.
The current work identifies the F877L mutation, neighboring the T878A mutation.
This disclosure also tested the W742C/T878A mutation and found that ectopic expression of this protein confers non-specific resistance to MDV3100.
These mutations are useful in patient stratification and development of novel therapeutics, as disclosed herein.
The nucleotide sequence of an example AR is shown below:

(SEQ ID NO: 2)
ATGGAAGTGCAGTTAGGGCTGGGAAGGGTCTACCCTCGGCCGCCGTCCAA

GACCTACCGAGGAGCTTTCCAGAATCTGTTCCAGAGCGTGCGCGAAGTGA

TCCAGAACCCGGGCCCCAGGCACCCAGAGGCCGCGAGCGCAGCACCTCCC

GGCGCCAGTTTGCTGCTGCTGCAGCAGCAGCAGCAGCAGCAGCAGCAGCA

GCAGCAGCAGCAGCAGCAGCAGCAGCAGCAGCAAGAGACTAGCC

CCAGGCAGCAGCAGCAGCAGGGTGAGGATGGTTCTCCCCAAGCCCAT

CGTAGAGGCCCCACAGGCTACCTGGTCCTGGATGAGGAACAGCAACCTTC

ACAGCCGCAGTCGGCCCTGGAGTGCCACCCCGAGAGAGGTTGCGTCCCAG

AGCCTGGAGCCGCCGTGGCCGCCAGCAAGGGGCTGCCGCAGCAGCTGCCA

GCACCTCCGGACGAGGATGACTCAGCTGCCCCATCCACGTTGTCCCTGCT

GGGCCCCACTTTCCCCGGCTTAAGCAGCTGCTCCGCTGACCTTAAAGACA

TCCTGAGCGAGGCCAGCACCATGCAACTCCTTCAGCAACAGCAGCAGGAA

GCAGTATCCGAAGGCAGCAGCAGCGGGAGAGCGAGGGAGGCCTCGGGGGC

TCCCACTTCCTCCAAGGACAATTACTTAGGGGGCACTTCGACCATTTCTG

ACAACGCCAAGGAGTTGTGTAAGGCAGTGTCGGTGTCCATGGGCCTGGGT

GTGGAGGCGTTGGAGCATCTGAGTCCAGGGGAACAGCTTCGGGGGGATTG

CATGTACGCCCCACTTTTGGGAGTTCCACCCGCTGTGCGTCCCACTCCTT

GTGCCCATTGGCCGAATGCAAAGGTTCTCTGCTAGACGACAGCGCAGGC

AAGAGCACTGAAGATACTGCTGAGTATTCCCCTTTCAAGGGAGGTTACAC

CAAAGGGCTAGAAGGCGAGAGCCTAGGCTGCTCTGGCAGCGCTGCAGCAG

GGAGCTCCGGGACACTTGAACTGCCGTCTACCCTGTCTCTCTACAAGTCC

GGAGCACTGGACGAGGCAGCTGCGTACCAGAGTCGCGACTACTACAACTT

TCCACTGGCTCTGGCCGGACCGCCGCCCCTCCGCCGCCTCCCCATCCCC

ACGCTCGCATCAAGCTGGAGAACCCGCTGGACTACGGCAGCGCCTGGGCG

GCTGCGGCGGCGCAGTGCCGCTATGGGACCTGGCGAGCCTGCATGGCGC

GGGTGCAGCGGGACCCGGTTCTGGGTCACCCTCAGCCGCCGCTTCCTCAT

CCTGGCACACTCTCTTCACAGCCGAAGAAGGCCAGTTGTATGGACCGTGT

GGTGGTGGTGGGGGTGGTGGCGGCGGCGGCGGCGGCGGCGGCGGCGGCGG

CGGCGGCGGCGGCGGCGGCGAGGCGGGAGCTGTAGCCCCCTACGGCTACA

CTCGGCCCCCTCAGGGGCTGGCGGGCCAGGAAAGCGACTTCACCGCACCT

GATGTGTGGTACCCTGGCGGCATGGTGAGCAGAGTGCCCTATCCCAGTCC

CACTTGTGTCAAAAGCGAAATGGGCCCCTGGATGGATAGCTACTCCGGAC

CTTACGGGGACATGCGTTTGGAGACTGCCAGGGACCATGTTTTGCCCATT

GACTATTACTTTCCACCCCAGAAGACCTGCCTGATCTGTGGAGATGAAGC

TTCTGGGTGTCACTATGGAGCTCTCACATGTGGAAGCTGCAAGGTCTTCT

TCAAAAGAGCCGCTGAAGGGAAACAGAAGTACCTGTGCGCCAGCAGAAAT

GATTGCACTATTGATAAATTCCGAAGGAAAAATTGTCCATCTTGTCGTCT

TCGGAAATGTTATGAAGCAGGGATGACTCTGGGAGCCCGGAAGCTGAAGA

AACTTGGTAATCTGAAACTACAGGAGGAAGGAGAGGCTTCCAGCACCACC

AGCCCCACTGAGGAGACAACCCAGAAGCTGACAGTGTCACACATTGAAGG

CTATGAATGTCAGCCCATCTTTCTGAATGTCCTGGAAGCCATTGAGCCAG

GTGTAGTGTGTGCTGGACACGACAACAACCAGCCCGACTCCTTTGCAGCC

TTGCTCTCTAGCCTCAATGAACTGGGAGAGAGACAGCTTGTACACGTGGT

CAAGTGGGCCAAGGCCTTGCCTGGCTTCCGCAACTTACACGTGGACGACC

AGATGGCTGTCATTCAGTACTCCTGGATGGGGCTCATGGTGTTTGCCATG

GGCTGGCGATCCTTCACCAATGTCAACTCCAGGATGCTCTACTTCGCCCC

TGATCTGGTTTTCAATGAGTACCGCATGCACAAGTCCCGGATGTACAGCC

AGTGTGTCCGAATGAGGCACCTCTCTCAAGAGTTTGGATGGCTCCAAATC

ACCCCCCAGGAATTCCTGTGCATGAAAGCACTGCTACTCTTCAGCATTAT

TCCAGTGGATGGGCTGAAAAATCAAAAATTCTTTGATGAACTTCGAATGA

ACTACATCAAGGAACTCGATCGTATCATTGCATGCAAAAGAAAAAATCCC

```
-continued
ACATCCTGCTCAAGACGCTTCTACCAGCTCACCAAGCTCCTGGACTCCGT

GCAGCCTATTGCGAGAGAGCTGCATCAGTTCACTTTTGACCTGCTAATCA

AGTCACACATGGTGAGCGTGGACTTTCCGGAAATGATGGCAGAGATCATC

TCTGTGCAAGTGCCCAAGATCCTTTCTGGGAAAGTCAAGCCCATCTATTT

CCACACCCAGTGA
```

Codons corresponding to the amino acids of note listed above (W 742, H 875, F 877, and T 878) are underlined. Of these:
TTC, mutated to CTC in all our resistant clones
ACT, mutated to GCT in a number of late stage and flutamide resistant tumors AR Mutations The present disclosure pertains to full-length Androgen Receptor or fragments or variants comprising a mutation at F877 and/or a double mutation at W742 and T878, wherein optionally the AR or fragment or variant can comprise additional mutations.

As defined herein, a "mutation" (e.g., of AR) can comprise a deletion or substitution of an amino acid.

As defined herein, a "fragment" or "variant" of AR comprises a polypeptide derived from the AR or a shortened form thereof. A "full-length" AR, as described herein, includes a polypeptide comprising an entire AR sequence, e.g., comprising the entire sequence shown in SEQ ID NO: 1 or 54. An AR fragment includes, without limitation, an AR which comprises less than the full-length sequence (e.g., less than that shown in SEQ ID NO: 1 or 54), but which retains at least one activity mediated by AR or an AR mutant [such as AR(F877)]. A variant is a fragment or full-length AR which has been modified. Such modifications include, without limitation, a post-translational modification (PEGylation, glycosylation, methylation, etc.). Modifications of AR or fragments also include combinations of the AR or fragment with an additional component, which may be covalently or non-covalently attached. Such other components may include a fusion partner (such as Fc, such as FcLALA), forming a fusion polypeptide or fusion protein.

Fragments and variants of AR may comprise various isoforms of AR, and/or comprise one or more of the domains of AR. AR is known to exist in two isoforms: AR-A (87 kDa), which is N-terminally-truncated and lacks the first 187 aa (amino acids), as a result of in vitro proteolysis. The isoform AR-B is 100 kDa and full-length. See: Wilson et al. 1994 Proc. Natl. Acad. Sci. USA 91: 1234-8; and Gregory et al. 2001 2001. J. Mol. Endocrinol. 27: 309-19.

Fragments can also include those "spanning" the F877 position, as described herein.

The various domains of AR include the N-terminal regulatory domain (including activation function 1, AF-1; activation function 5, AF-5; and dimerization surface), a DNA binding domain (DBD), a hinge region, a ligand binding domain (LBD), and a C-terminal domain. An AR(F877) and AR(W742/T878), for example, can have one or more domains, provided that the sequence of the AR(F877) and AR(W742/T878) encompass the positions F877, or 742 and 877, respectively.

It is also noted that Androgen Receptor mutations comprise both deletions and substitutions of particular amino acids. Thus, an AR(F877) is a fragment or full-length AR or variant which can have a deletion at F877; thus, there is no amino acid at the position normally corresponding to F877 (e.g., as shown in SEQ ID NO: 54). Thus, the AR(F877) can comprise an amino acid at position 875 directly linked to the amino acid corresponding to position 877, skipping F877. The amino acids at positions 875 and 877 can, in various embodiments, be optionally mutated, too.

The term "AR(F877)" and "AR(W742/T878)" are thus meant to include any full-length, fragment, variant or other form of AR which retains at least one activity mediated by AR and which comprises, respectively, a mutation at F877 or a double mutation at both W742 and T878, optionally comprising additional mutations.

The disclosure also pertains to compositions comprising a AR(F877) and AR(W742/T878) "polypeptide", "polypeptide moiety", "protein" and the like. The terms "polypeptide", "polypeptide moiety", "protein", and the like are used interchangeably herein to refer to any polymer of amino acid residues of any length. The polymer can be linear or non-linear (e.g., branched), it can comprise modified amino acids or amino acid analogs, and it can be interrupted by chemical moieties other than amino acids. The terms also encompass an amino acid polymer that has been modified naturally or by intervention; for example, by disulfide bond formation, glycosylation, lipidation, acetylation, phosphorylation, or any other manipulation or modification, such as conjugation with a labeling or bioactive component.

The present disclosure thus relates to AR or fragments or variants thereof comprising a mutation at F877 or a double mutation at W742/T878, optionally comprising other mutations, which are useful in patient stratification and/or in generating novel therapeutics for use in treating androgen receptor-related diseases.

Activities of WT or Mutant AR

In various aspects, the fragment and/or variant of the AR or a mutant AR (such as AR(F877) and/or AR(W742/T878) retains at least one activity of the full-length WT or mutant polypeptide (e.g., a polypeptide of SEQ ID NOs: 1 or 54). Such activities include: but are not limited to an androgen, testosterone and/or dihydrotestosterone; inability to bind MDV3100; a conformational change upon binding of a ligand; dissociation of heat shock proteins; transport from the cytosol into the cell nucleus; dimerization; ability to bind DNA; sequence-specific binding to a HRE (hormone response element) sequence in DNA; regulation of gene transcription; a role in phosphorylation of other receptors; interaction with signal transduction proteins in the cytoplasm; activation function 1 (AF-1) for full ligand activated transcriptional activity; activation function 2 (AF-2), responsible for agonist induced activity; and/or interaction with AKT1, BAG1, Beta-catenin, BRCA1, C-jun, Calmodulin 1, Caveolin 1, CDK9, COX5B, CREB-binding protein, Cyclin D1, Cyclin-dependent kinase 7, Death associated protein 6, Deleted in Colorectal Cancer, EFCAB6, Epidermal growth factor receptor, FOXO1, GAPDH, Gelsolin, GNB2L1, GSK3B, HDAC1, HSP90AA1, HTATIP, MAGEA11, MED1, MYST2, NCOA1, NCOA2, NCOA3, NCOA4, NCOA6, NCOR2, NONO, PA2G4, PAK6, PATZ1, PIAS2, PRPF6, PTEN, RAD9A, RANBP9, RCHY1, Retinoblastoma protein, RNF14, RNF4, SART3, SMAD3, Small heterodimer partner, Src, SRY, STAT3, SVIL, Testicular receptor 2, Testicular receptor 4, TGFB1I1, TMF1, TRIM68, UBE2I, UXT, and/or ZMIZ1, or mediating specific immunogenicity [e.g., a fragment of AR(F877) can be any fragment which is long enough to mimic the immunogenicity or which can be used to raise or elicit antibodies which bind to the corresponding fragment or sequence of AR or AR(F877)]. Thus, for example, an AR(F877) fragment is any fragment which retains the activity of being capable of eliciting an immune response specific to a sequence of the whole AR(F877) or a fragment thereof spanning the AR(F877).

At least one such activity of AR is retained by an AR mutant, fragment or variant, such as AR(F877) or AR(W742/T878), which are described in more detail below.

AR(F877)

As detailed herein, the emergence of the F877 mutation in AR correlated with blunted AR response to MDV3100 and sustained proliferation during treatment. A recurrent F877L mutation in the AR gene was conserved among all four strongly resistant clones (described herein) and not found in weakly resistant clones or control cell lines. The F877 mutation allows AR(F877L) to use MDV3100 as an agonist and, consistently with this, F877L-bearing cells required the presence of MDV3100 for growth in vivo.

The mechanism by which MDV3100 inhibits AR signaling has been attributed partially to its ability to hinder nuclear translocation of AR. Tran et al. 2009 Science 324: 787-90. The F877 mutation is localized to the ligand-binding domain of AR. To assess the potential impact of the F877L mutation on MDV3100 response, we computationally modeled the binding of MDV3100 to the wild-type (WT) and mutant receptors. We found that in the docking modes of the antagonistic state of WT AR, MDV3100 only displayed a weak interaction with AR(F877). However, in the presence of the F877L mutation, the benzamide motif of MDV3100 can extend into the access channel created by the smaller leucine residue. This would potentially prevent the compound from clashing with helix-12 of the AR ligand-binding domain in the agonistic mode. Thus, computational modeling suggested that F877L mutation in AR may abolish the antagonistic activity of MDV3100 and could potentially allow agonist activity.

An "AR(F877)" or "AR-F877", as defined herein, is a polypeptide or the like comprising Androgen Receptor or a fragment or variant thereof comprising or spanning position 877, wherein the amino acid at position 877 is substituted or deleted or is other than phenylalanine (F) (wherein the position of the amino acids is in accordance with the numbering of SEQ ID NO: 1 or SEQ ID NO: 54). An "AR(F877L)" or "AR-F877L", as defined herein, is a polypeptide or the like comprising Androgen Receptor or a fragment or variant thereof comprising or spanning position 877, wherein the amino acid at position 877 is substituted with Leucine (L) (wherein the position of the amino acids is in accordance with the numbering of SEQ ID NO: 1 or SEQ ID NO: 54).

Thus, an "AR(F877)" comprises the whole or a fragment of SEQ ID NO: 54, below (which is identical to SEQ ID NO: 1, except that the F877 is indicated by an "X", meaning that any amino acid other than F can be substituted in this position, or that this amino acid can be deleted). Thus, in an AR(F877), the position X can be deleted or can be any amino acid other than F.

A non-limiting example of an AR(F877) polypeptide sequence is shown below:

```
                                              (SEQ ID NO: 54)
MEVQLGLGRVYPRPPSKTYRGAFQNLFQSVREVIQNPGPRHPEAASAAPP

GASLLLLQQQQQQQQQQQQQQQQQQQQQQQQQETSPRQQQQQQGEDGSPQAH

RRGPTGYLVLDEEQQPSQPQSALECHPERGCVPEPGAAVAASKGLPQQLP

APPDEDDSAAPSTLSLLGPTFPGLSSCSADLKDILSEASTMQLLQQQQQE
```

-continued
```
AVSEGSSSGRAREASGAPTSSKDNYLGGTSTISDNAKELCKAVSVSMGLG

VEALEHLSPGEQLRGDCMYAPLLGVPPAVRPTPCAPLAECKGSLLDDSAG

KSTEDTAEYSPFKGGYTKGLEGESLGCSGSAAAGSSGTLELPSTLSLYKS

GALDEAAAYQSRDYYNFPLALAGPPPPPPPPHPHARIKLENPLDYGSAWA

AAAAQCRYGDLASLHGAGAAGPGSGSPSAAASSSWHTLFTAEEGQLYGPC

GGGGGGGGGGGGGGGGGGGGGGGGEAGAVAPYGYTRPPQGLAGQESDFTAP

DVWYPGGMVSRVPYPSPTCVKSEMGPWMDSYSGPYGDMRLETARDHVLPI

DYYFPPQKTCLICGDEASGCHYGALTCGSCKVFFKRAAEGKQKYLCASRN

DCTIDKFRRKNCPSCRLRKCYEAGMTLGARKLKKLGNLKLQEEGEASSTT

SPTEETTQKLTVSHIEGYECQPIFLNVLEAIEPGVVCAGHDNNQPDSFAA

LLSSLNELGERQLVHVVKWAKALPGFRNLHVDDQMAVIQYSWMGLMVFAM

GWRSFTNVNSRMLYFAPDLVFNEYRMHKSRMYSQCVRMRHLSQEFGWLQI

TPQEFLCMKALLLFSIIPVDGLKNQKFFDELRMNYIKELDRIIACKRKNP

TSCSRRFYQLTKLLDSVQPIARELHQXTFDLLIKSHMVSVDFPEMMAEII

SVQVPKILSGKVKPIYFHTQ
```

Thus, example AR(F877) polypeptides or fragments or variants thereof can comprise a subset of SEQ ID NO: 54, for example, ELHQXTFDLL (SEQ ID NO: 20), LHQXTF (SEQ ID NO: 21), HQXTFD (SEQ ID NO: 22), QXTFD (SEQ ID NO: 23), etc., wherein X is deleted or is any amino acid other than F. Other non-limiting examples of AR(F877) polypeptides include those that comprise, for example, any of SEQ ID NOs: 3-53, as shown herein. In various embodiments, the fragment can mediate any activity of an AR.

The term "AR(F877)" explicitly also encompasses AR with a deletion at position F877. Thus: By "spanning" is meant that the mutant AR comprises a sequence such that the amino acid at position F877 is absent or deleted. For example, a mutant AR comprising a sequence "spanning" F877 can comprise an amino acid sequence comprising, inter alia, the amino acids at position 875 and 877 but not F877. In another non-limiting example, the mutant AR comprising a sequence "spanning" F877 can comprise a gap of 1, 2, 3 or 4 amino acids including F877; e.g., the mutant AR can have a sequence that comprises the amino acids at positions 875 and 878 (lacking those between, including 877 and F877), or comprising the amino acids at positions 875 and 877 (lacking those between, including 875 and 877). Thus, example AR(F877) polypeptides or fragments or variants thereof can comprise, for example, ELHQ_T (SEQ ID NO: 24), LHQ_TF (SEQ ID NO: 25), HQ_TFD (SEQ ID NO: 26), or Q_TFDL (SEQ ID NO: 27), etc., wherein "_" indicates a deletion of the amino acid at position F877.

The AR(F877) can comprise additional mutations, such as at position T878. Specific AR(F877) include those designated, for example, "F877L" ("F877L AR") or "F877L/T878A" ("F877L/T878A AR"), indicating that they have a F to L substitution at position 877, or else both a F to L substitution at position 877 and a T to A substitution at position 877.

A AR(F877) polypeptide, fragment or variant can thus comprise a subset of the amino acid sequence of SEQ ID NO:1, wherein the subset comprises the position 877, which is represented as "X" to indicate that any amino acid other than phenylalanine (F) is at position 877. Thus, a AR(F877) polypeptide, fragment or variant can comprise, without limitation and inter alia, for example:

PIARELHQXT (SEQ ID NO: 3)

IARELHQXTF (SEQ ID NO: 4)

ARELHQXTFD (SEQ ID NO: 5)

RELHQXTFDL (SEQ ID NO: 6)

ELHQXTFDLL (SEQ ID NO: 7)

LHQXTFDLLI (SEQ ID NO: 8)

HQXTFDLLIK (SEQ ID NO: 9)

QXTFDLLIKS (SEQ ID NO: 10)

QXTFDLLIKSH (SEQ ID NO: 11)

Alternatively, a AR(F877) polypeptide, fragment or variant can thus comprise a sequence spanning the position 877, wherein the amino acid at his position is deleted, which is represented as "_" below. Thus, a AR(F877) polypeptide, fragment or variant can comprise, without limitation and inter alia, for example:

QPIARELHQ_T (SEQ ID NO: 28)

PIARELHQ_TF (SEQ ID NO: 29)

IARELHQ_TFD (SEQ ID NO: 30)

ARELHQ_TFDL (SEQ ID NO: 31)

RELHQ_TFDLL (SEQ ID NO: 32)

ELHQ_TFDLLI (SEQ ID NO: 33)

LHQ_TFDLLIK (SEQ ID NO: 34)

HQ_TFDLLIKS (SEQ ID NO: 35)

Q_TFDLLIKSH (SEQ ID NO: 36)

In some embodiments, a AR(F877) polypeptide, fragment or variant can comprise a mutation at one or more other positions, in addition to a mutation at F877.

Thus, in some embodiments, the AR(F877) polypeptide, fragment or variant can comprise a mutation at both F877 (indicated by the first "X" in the sequence "XX") and T878 (indicated by the second "X" in the sequence "XX"), below. Thus, a AR(F877) polypeptide, fragment or variant can comprise, without limitation and inter alia, for example:

QPIARELHQXX (SEQ ID NO: 37)

PIARELHQXXF (SEQ ID NO: 38)

IARELHQXXFD (SEQ ID NO: 39)

ARELHQXXFDL (SEQ ID NO: 40)

RELHQXXFDLL (SEQ ID NO: 41)

ELHQXXFDLLI (SEQ ID NO: 42)

LHQXXFDLLIK (SEQ ID NO: 43)

HQXXFDLLIKS (SEQ ID NO: 44)

QXXFDLLIKSH (SEQ ID NO: 45)

In some embodiments, the AR(F877) polypeptide, fragment or variant can comprise a mutations at: H875 (indicated by the "X" in the sequence "XQXX"); F877 (indicated by the second "X" in the sequence "XQXX") and T878 (indicated by the third "X" in the sequence "XQXX"), below. Thus, a AR(F877) polypeptide, fragment or variant can comprise, without limitation and inter alia, for example:

QPIARELXQXX (SEQ ID NO: 46)

PIARELXQXXF (SEQ ID NO: 47)

IARELXQXXFD (SEQ ID NO: 48)

ARELXQXXFDL (SEQ ID NO: 49)

RELXQXXFDLL (SEQ ID NO: 50)

ELXQXXFDLLI (SEQ ID NO: 51)

LXQXXFDLLIK (SEQ ID NO: 52)

XQXXFDLLIKS (SEQ ID NO: 53)

In various other embodiments, the AR(F877) polypeptide, fragment or variant can comprise a substitution or deletion at F877 and one or more other mutations, modifications, etc. The AR(F877) polypeptide, fragment or variant can comprise a mixed variety of substitutions and deletion mutations.

Other AR Mutations

Other AR mutations have been previously described.

W742 mutations, e.g. W742C, occur in a number of bicalutamide resistant tumors. Hara et al. Cancer Res. 63: 149-153 (2003). Taplin et al. J. Clin. Oncol. 21: 2673-2678 (2003); Haapala et al. Labor. Invest. 81: 1647-1651 (2001). This disclosure shows that this mutation, in combination with a mutation at T878 can also partially confer phenotypic resistance to MDV3100. Without wishing to be bound to any particular theory, this disclosure speculates that this may be due to an indirect effect as the double mutant AR gains a constitutive active function.

H875 mutations, such as H875Y, are known to occur in a number of prostate tumors.

F877 mutations, e.g., F877L, are shown herein to cause resistance to MDV3100. However, patients presenting the F877L/T878A mutation can readily be treated with treatments which lack MDV3100 such as bicalutamide to achieve clinical benefit.

It is noted, however, that W742C/L single mutants are sensitive (at least as determined by reporter assays); however, the W742C/T878A AR becomes constitutively active and shows phenotypic resistance.

T878 mutations, e.g., T878A, are known to occur in a number of late stage and flutamide resistant tumors. Fenton et al. Clin. Cancer Res. 3: 1383-1388 (1997); Taplin et al. Cancer Res. 59: 2511-2515 (1999). This disclosure shows that the double mutation at W742 and T878 also causes resistance to MDV3100.

Additional AR mutations include, for example, those at L701 (e.g., L701H), V716 (e.g., V716M), Q902 (e.g., Q902R), and A721 (e.g., A721T). Fenton et al. Clin. Cancer Res. 3: 1383-1388 (1997). Some mutation sites are known to be clinically relevant. For example, H875Y, V716M, and L701H/T878A have been shown to possess a broadened spectrum of ligand responsiveness, and hydroxyflutamide has previously been shown to work as an agonist for these mutants. Fenton et al. Clin. Cancer Res. 3: 1383-1388 (1997); Hara et al. Cancer Res. 63: 149-153 (2003); Veldscholte et al. Biochem. 31: 2393-2399 (1992); Zhao et al. Nature Med. 6: 703-706 (2000). T878A, T878S, and H875Y mutants are known to have increased responses to both estradiol and progesterone relative to WT AR. H875Y and T878S AR can be activated by nilutamide. See: Fenton et al. Clin. Cancer Res. 3: 1383-1388 (1997) and references cited therein.

Sites known to be susceptible to be mutation are sometimes referred to as "hotspots".

In patient stratification and drug regimen design, the known roles, drug sensitivities, and antagonist-to-agonist switches of various known AR mutations should be taken into account.

While, in some cases, only one substitution has been described for a particular position, this disclosure contemplates that any amino acid (or none at all, in the case of a deletion) can be at the site for a mutation. Thus, the disclosure contemplates that any amino acid other than F (or none at all) can be at position F877 in AR(F877). Preferred substitutions are those that demonstrate the ability (such as shown by F877L) to be resistant to MDV3100. Similarly, any amino acids can be substituted (or the position deleted) in the double mutation of W742/T878, especially if the double mutation (like that of W742C/T878A) also confers resistance to MDV3100.

Additional description and discussion of the AR(F877) mutation and W742/T878 double mutation are presented below. In these texts, the disclosure discusses: whether the F877L example of the AR(F877) mutation is pre-existing or acquired in response to MDV3100; W742C/T878A mutation indirectly confers resistance to MDV-3100; the antagonist-to-agonist switch; and alternative mechanisms of resistance to MDV3100.

F877L: Hotspot Mutation in AR in Response to MDV3100 Treatment

Figure 3A:
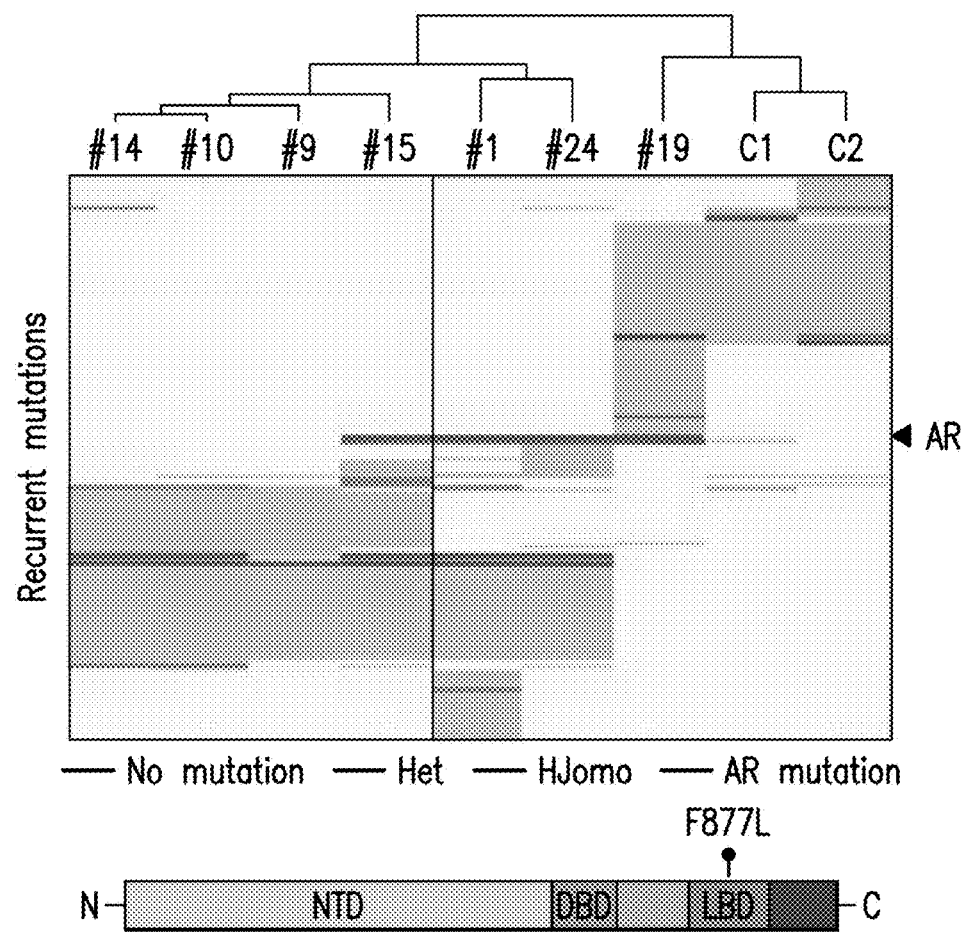
FIG. 3. Whole-transcriptome sequencing analysis identifies a novel F877L mutation in AR in strongly resistant lines and xenograft tumors. A, upper, unbiased hierarchical clustering of somatic mutations detected in controls (brown font), weakly resistant (red font), and strongly resistant clones (green font). Grey line represents lack of mutation; orange line represents single recurrent heterozygous mutation; red line represents recurrent homozygous mutation; green line represents recurrent mutation in AR, as indicated by green arrowhead. Lower, schematic of human androgen receptor. NTD, N-terminal domain; DBD, DNA-binding domain; LBD, ligand-binding domain. Site of F877L mutation indicated by green line and green font. B, left, IGV plot showing heterozygous nature of F877L mutation in exon 8 of AR in strongly resistant clones (indicated by green arrowheads). F877L mutation is adjacent to a preexisting homozygous T878A mutation (orange shade) in LNCaP. Right, raw counts of wild-type (WT, red shade) and mutant (Mut, green shade) AR alleles in strongly resistant clones. C, tumor growth kinetics of two vehicle-treated (red curves) and four MDV3100-treated (green curves) LNCaP tumors. D, IGV plot showing the relative position and frequency of nucleotide substitutions promoting F877L in MDV3100 resistant tumors. C1-C2, vehicle-treated tumors; R1-R4, MDV3100-resistant tumors. E, table summarizing data from IGV plot. Red shade represents tumors bearing WT AR whereas green shade highlights tumors bearing F877L mutant AR. F, bar graphs showing relative expression of AR target genes KLK3 and NKX3-1 in LNCaP tumors. Red bars, expression data from tumors expressing AR-WT; green bars, expression data from tumors harboring AR-F877L.
Figure 3B:
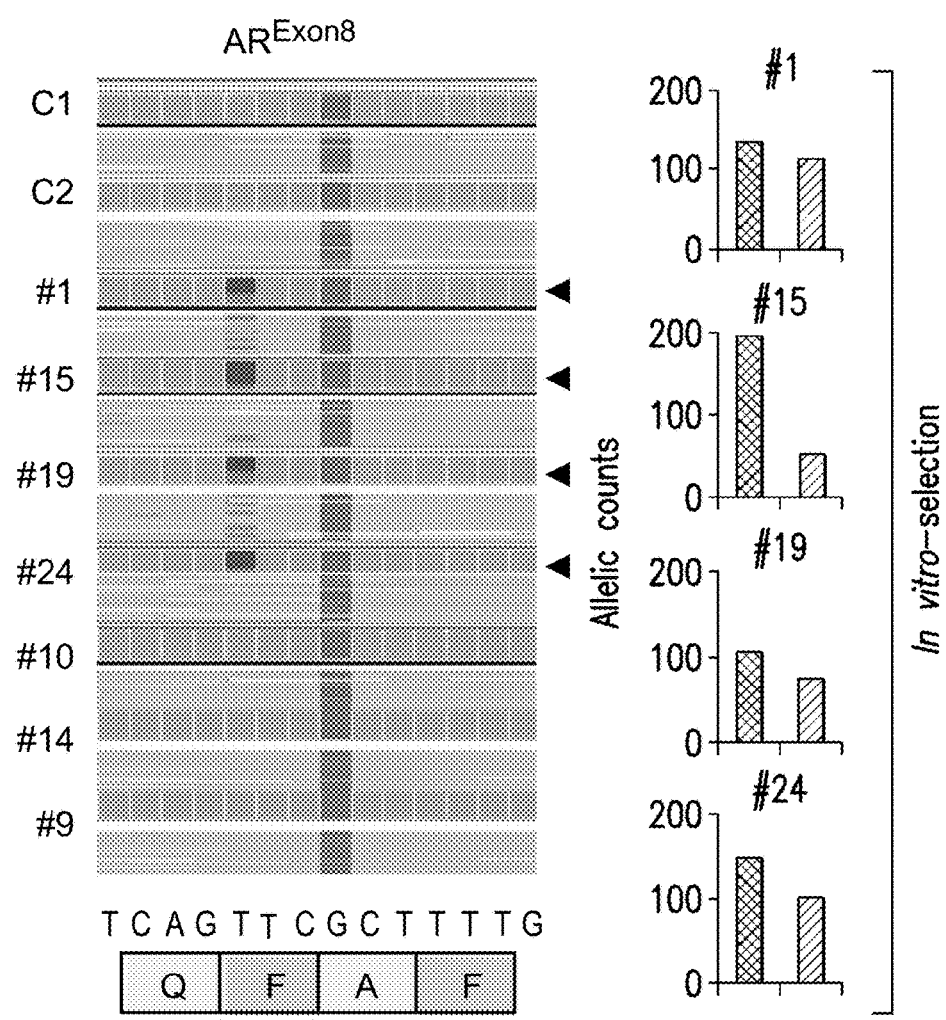
Figure 3C:
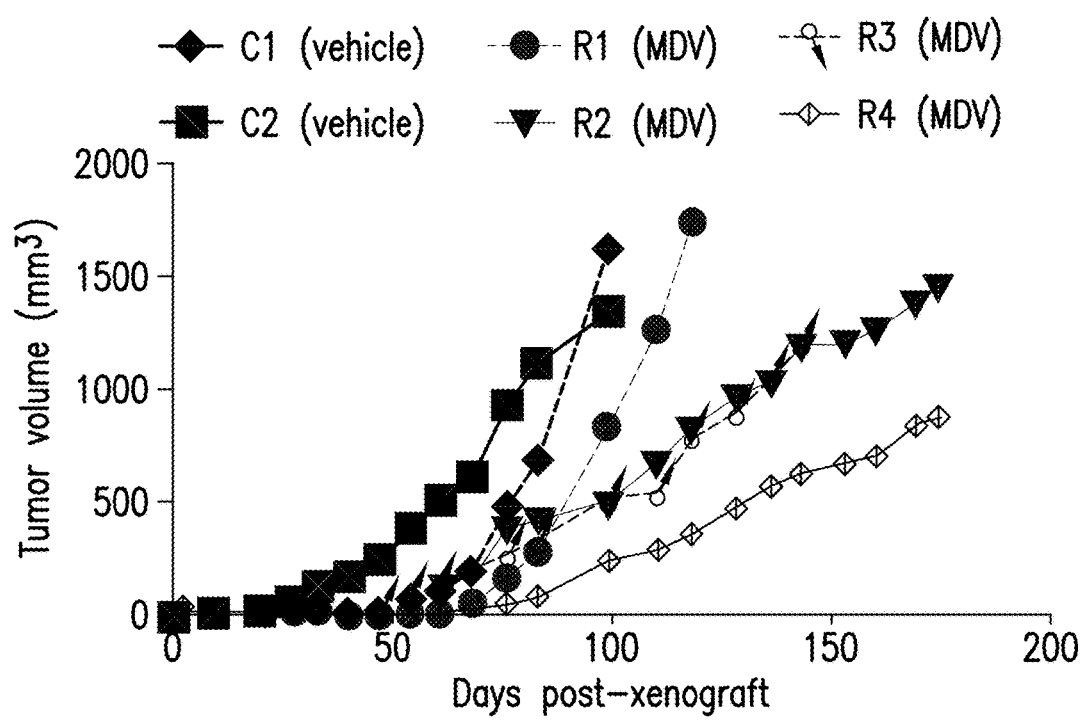
Figure 3D:
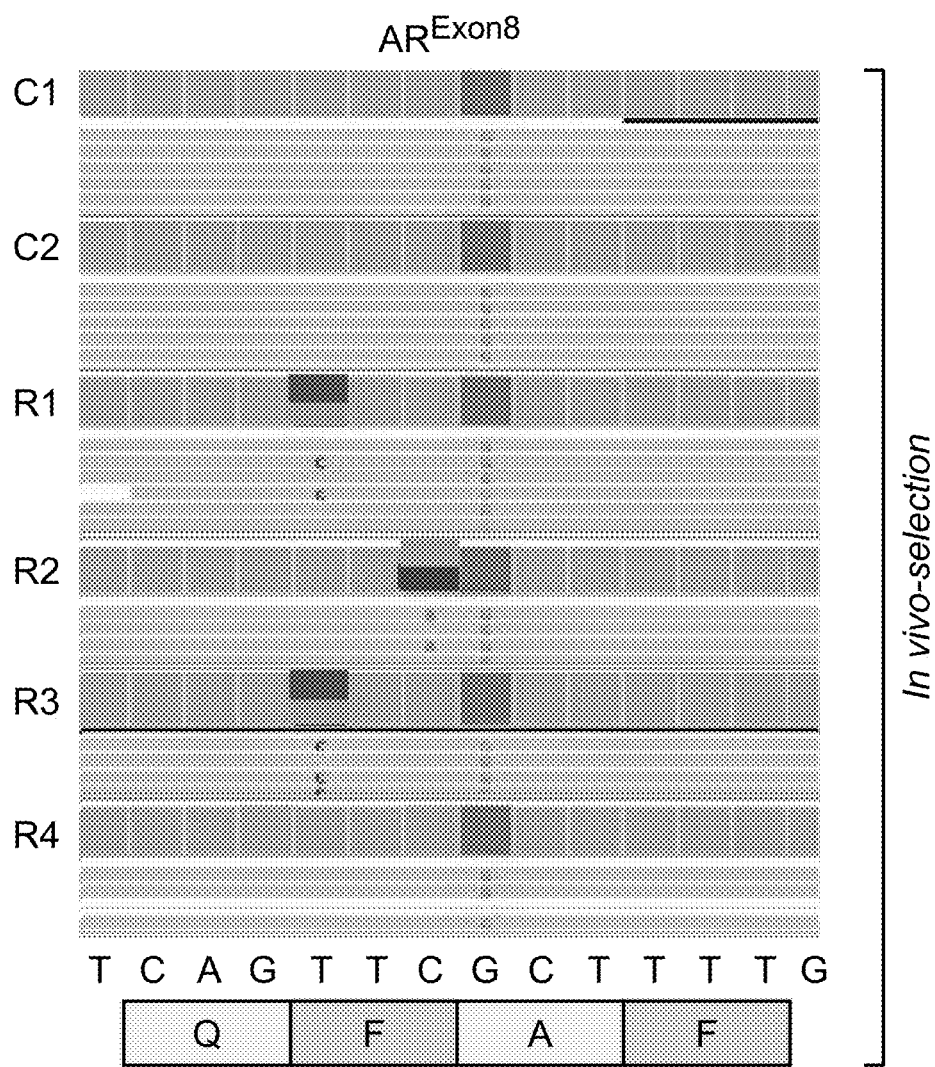
Figures 3E, 3F:
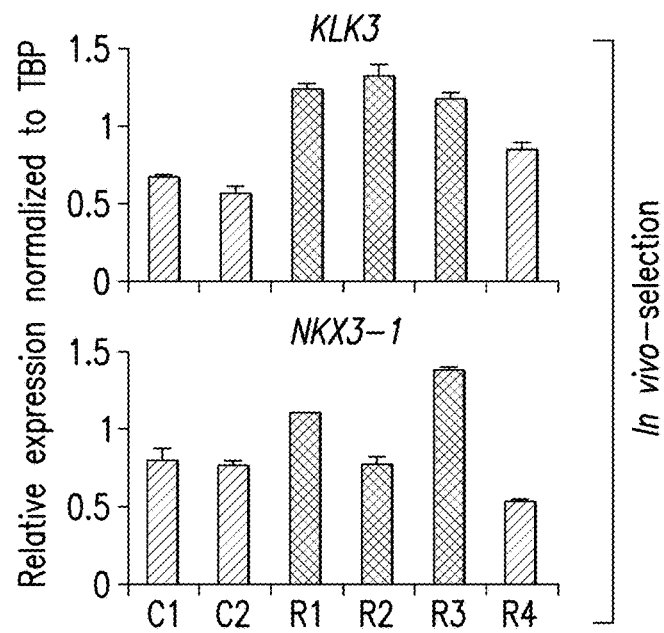
Figure 4A:
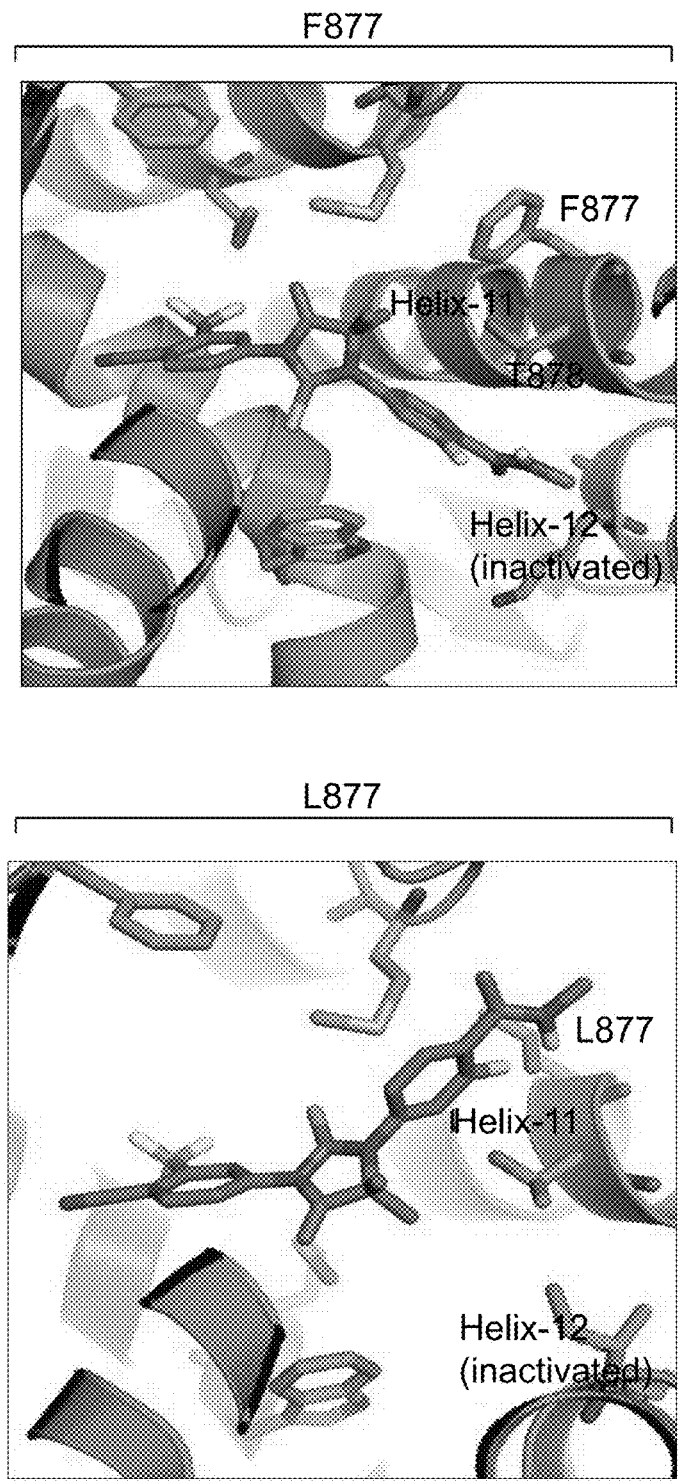
FIG. 4. F877L mutation functionally confers an antagonist-to-agonist switch. A, comparison of the docking modes of MDV3100 in an inactivated state of wild-type (WT) AR (left) with a speculative model of MDV3100 bound to an activated state of mutant AR (right). B, bar graphs showing normalized AR reporter activity following transfection of 293T (top) and VCaP (bottom) cells with various AR expression constructs ($AR^{WT}$, $AR^{T878A}$, $AR^{F877L}$, $ARF^{877L/T878A}$) and subsequent treatment with vehicle (Veh), 0.1 nM R1881 (R), 10 μM MDV3100 (MDV), 10 μM bicalutamide (Bic), 10 μM MDV3100+0.1 nM R1881 (M/R) or 10 μM bicalutamide+0.1 nM R1881 (B/R) for 24 h. All data is normalized to Renilla luciferase ($R_{LUC}$) expression. Data represent mean±SEM; n=3. *P<0.001 (Student's t-test). C, qPCR analysis of KLK3 expression in a control line (C1), weakly resistant (red font) and strongly resistant (green font) clones following treatment with vehicle (V), 0.1 nM R1881, 0.1 nM R1881+10 μM MDV3100 (MDV) and 0.1 nM R1881+10 μM bicalutamide (Bic) in 10% CSS for 24 h. TBP used to normalize expression. Data represent mean±SEM; n=3. *P<0.05, **P<0.01 (Student's t-test).
Figure 4B:
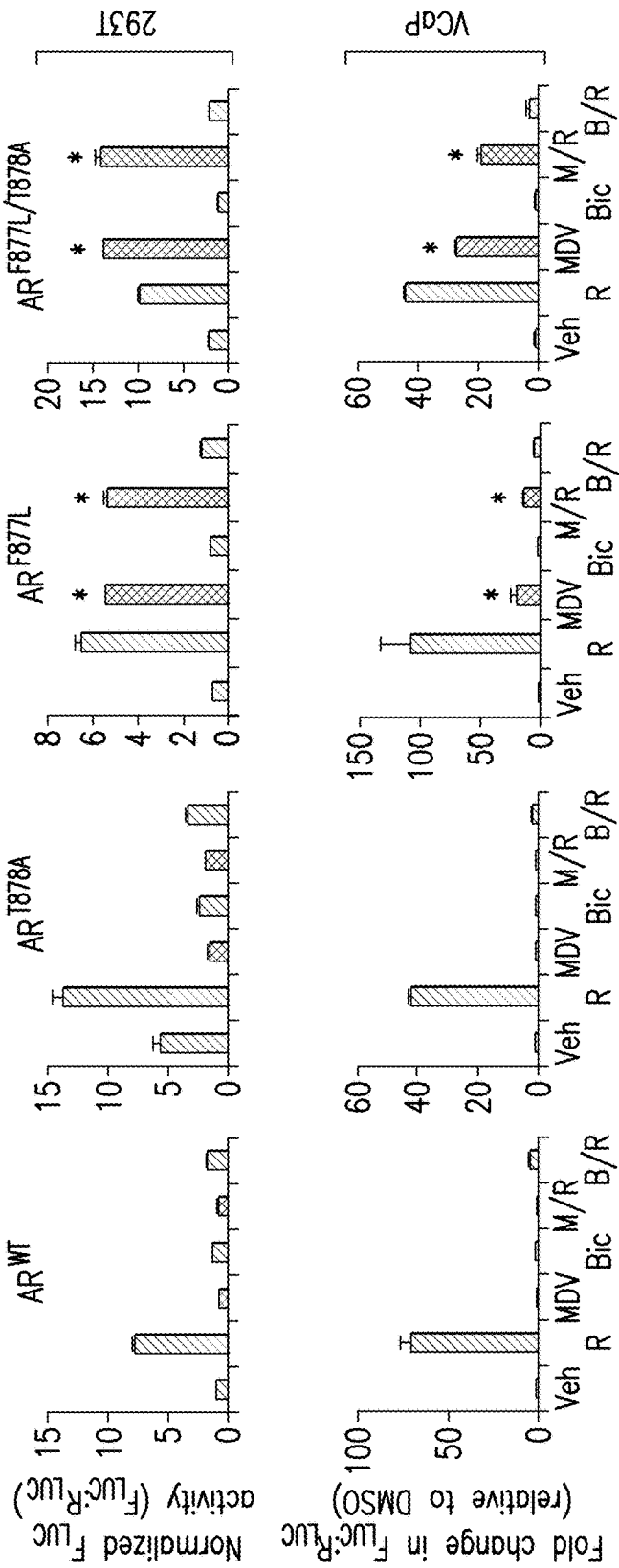
Figure 4C:
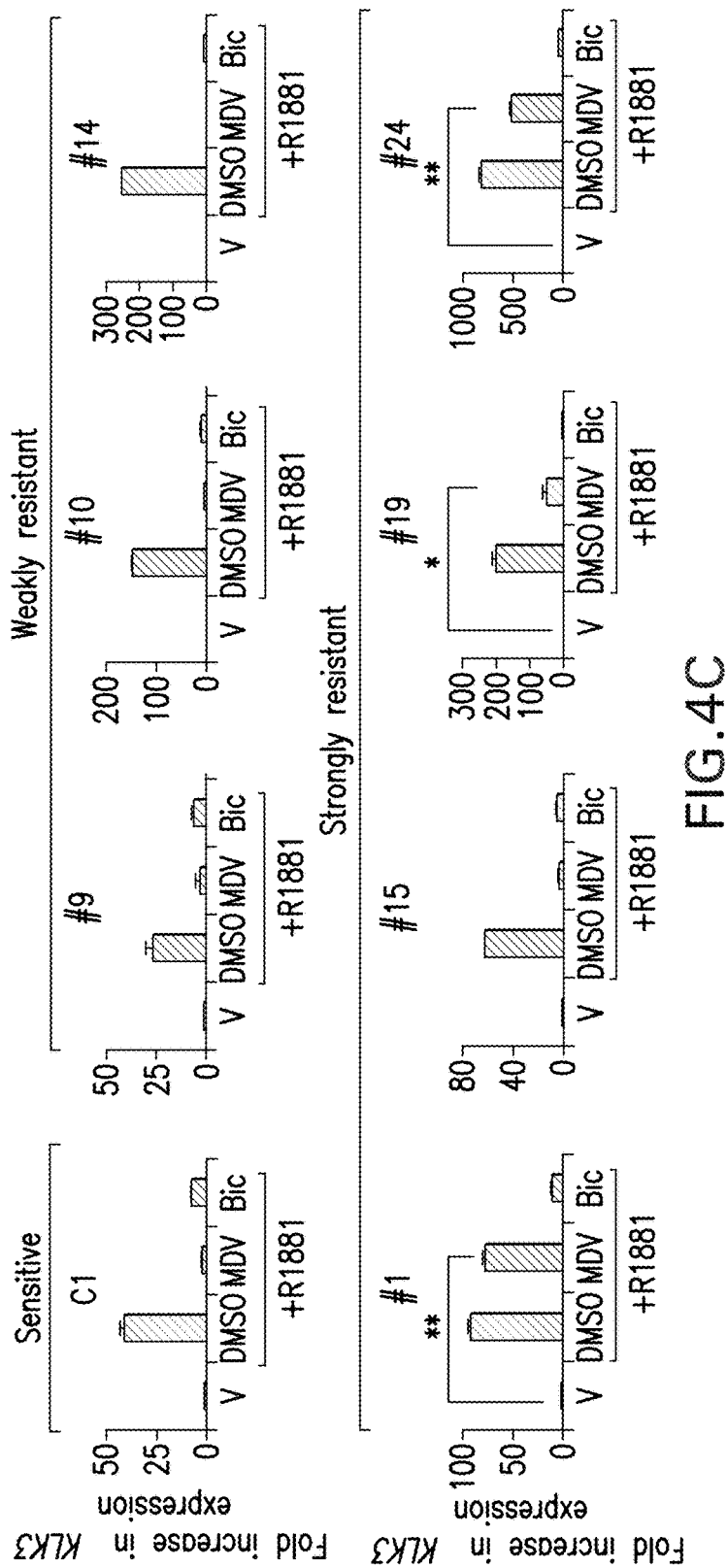

The relatively quick emergence of the F877L mutation during in vitro selection (FIG. 3A, B) initially suggested that this mutation was likely pre-existing at a low frequency. However, the fact that two independent nucleotide substitutions led to the F877L mutation during in vivo selection (FIGS. 3D and E) implies that the mutation may have been acquired during treatment. Since LNCaP cells possess defects in the mismatch repair (MMR) mechanism, deficiencies found to also exist in a subset of PCa [Chen et al. 2001 Cancer Res. 61: 4112-21] it is conceivable that they may more easily acquire this mutation (either with or without MDV3100 treatment). However, the fact that Balbas and colleagues (2013) also reported the spontaneous emergence of F877L upon prolonged treatment of CWR22PC cells [Balbas et al. 2013 eLife 2:e00499] a line that is believed to possess an intact MMR mechanism, suggests that F877L may truly be a hotspot mutation that may possess the capacity to confer resistance in prostate tumors irrespective of the MMR status.

W742C/T878A Mutation Indirectly Confers Resistance to MDV3100

It was noted above that the double mutation AR(W742/T878), in addition to AR(F877) confers resistance to MDV3100.

Figure 15:
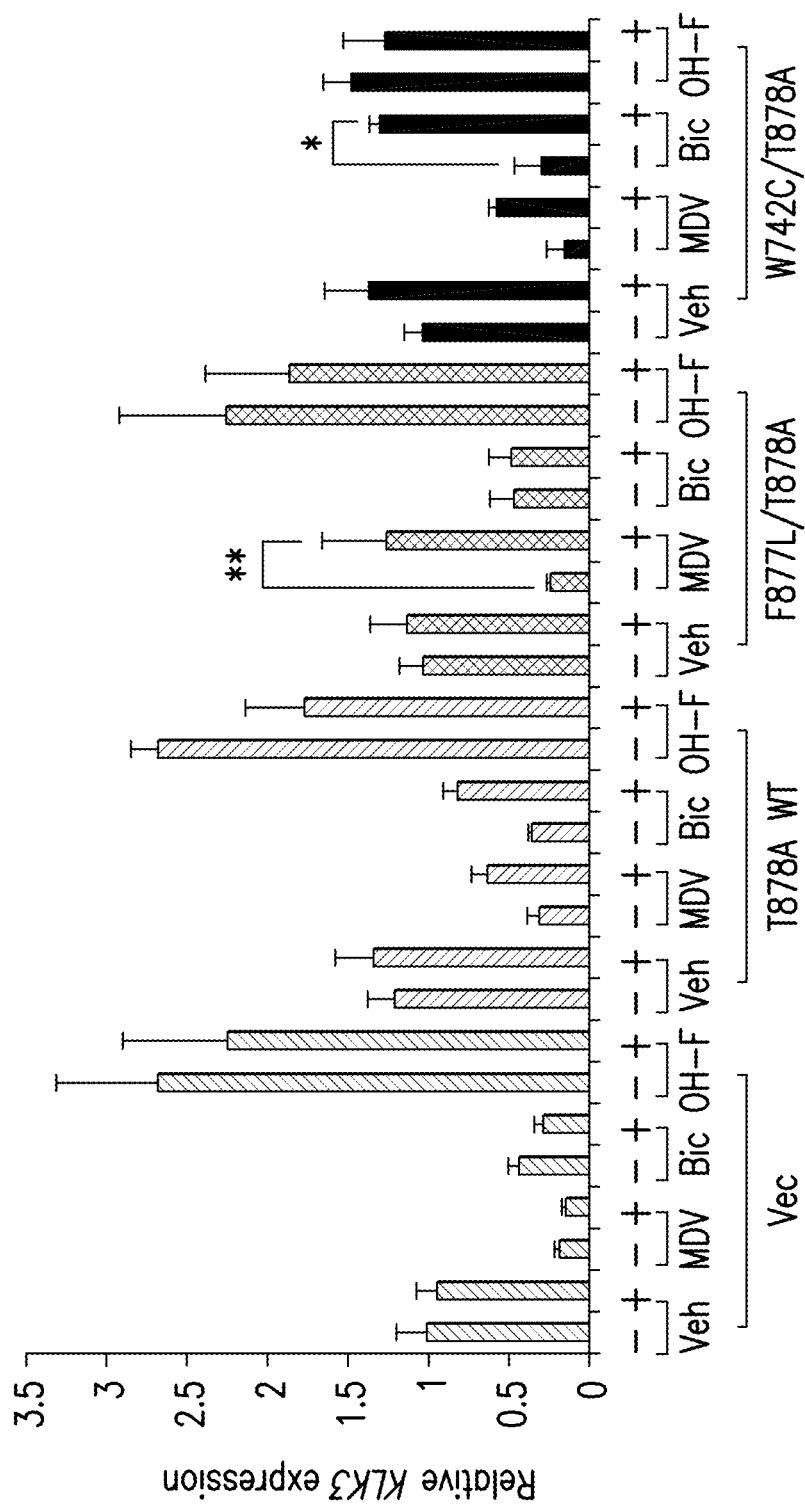
FIG. 15. F877L/T878A mutant AR can efficiently rescue AR signaling in the presence of MDV3100. qPCR analysis of KLK3 expression in various engineered lines (vector-beige bars; T878A-red bars; F877L/T878A-green bars; W742C/T878A-blue bars) following treatment with DMSO (Veh), 10 μM MDV3100 (MDV), 10 μM bicalutamide (Bic) or 10 μM hydroxyflutamide (OH—F) in RPMI 1640 supplemented with 10% FCS. −/+, untreated or treated with Dox respectively. TBP used to normalize expression. Data represent mean±SEM; n=3. * P<0.05, **P<0.01 (Student's t-test).
Figure 16A:
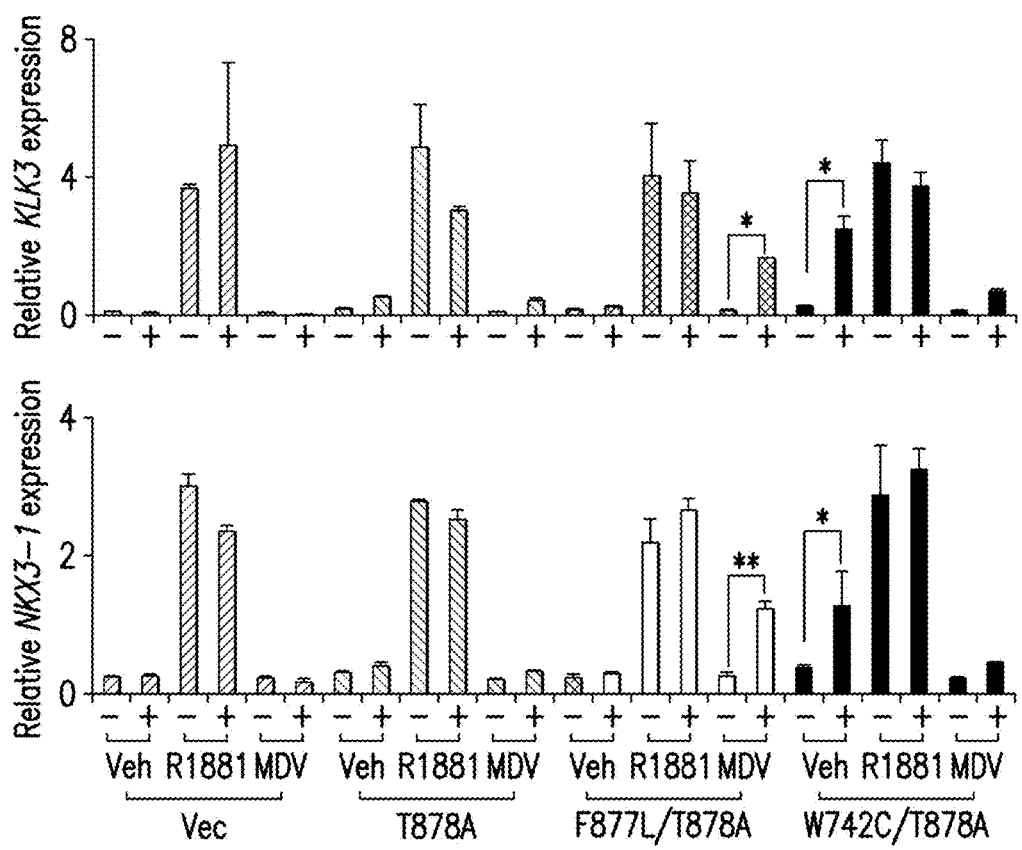
FIG. 16. F877L/T878A mutant AR utilizes MDV3100 as an agonist in androgen-depleted media. A, qPCR analysis of KLK3 and NKX3-1 expression in various engineered lines (vector-beige bars; T878A-red bars; F877L/T878A-green bars; W742C/T878A-blue bars) treated with DMSO (Veh), 0.1 nM R1881 (R1881) or 10 μM MDV3100 (MDV) in 10% CSS. −/+, untreated or treated with Dox respectively. TBP used to normalize expression. Data represent mean±SEM; n=3. *P<0.05, **P<0.01 (Student's t-test). B, western analysis of exogenous AR expression levels (probed with HA) in cytoplasmic and nuclear fractions of T878A and F877L/T878A engineered lines treated with DMSO (Veh), 0.1 nM R1881 (R1881) or 10 μM MDV3100 (MDV) for 24 h. β-tubulin (cytosolic protein) and histone H3 (nuclear protein) were probed to verify purity of fractions. Engineered lines were cultured in 10% CSS in the presence of Dox for 3-4 d prior to treatment.

Although unexpected, this disclosure consistently found that expressing the W742C/T878A AR, albeit much stronger expression levels than the F877L/T878A allele, conferred phenotypic resistance to MDV3100. This phenomenon is likely to be an indirect effect by virtue of the W742C/T878A mutant AR gaining constitutively active characteristics, in support of an earlier report. Hara, T., et al. *Cancer research* 63, 149-153 (2003). Although gene expression analysis suggests that this mutation can rescue AR pathway activity more efficiently than the T878A mutant AR in the presence of MDV3100 (FIG. 5a), this is likely independent of MDV3100 since ectopic expression of this allele can significantly enhance AR signaling at baseline (FIGS. 15 and 16a and data not shown). In support of this, this disclosure observes greater nuclear localization of the W742C/T878A mutant AR at baseline relative to the T878A AR under androgen-depleted conditions. While nuclear localization remains sensitive to MDV3100—as treatment reduces localization significantly—the level of nuclear W742C/T878A protein remains higher than the T878A AR following MDV3100 treatment, translating to a greater degree of resistance. Although the resistance mechanism is likely to be indirect for the reasons described above, it is still a notable observation as it would imply that MDV3100 or other anti-androgens are likely to be completely ineffective, and 'combined androgen blockade' treatments using other classes of AR antagonists or combination therapies with agents that also target other key signaling pathways, may be more effective in treating tumors harboring the W742C/T878A mutation.

The unexpected finding that the W742C/T878A allele can confer partial resistance to MDV3100 implies the necessity to screen the functions of other well documented mutations in AR in clinical prostate cancer samples. Taplin, M. E., et al. *The New England journal of medicine* 332, 1393-1398 (1995); Marcelli, M., et al. *Cancer research* 60, 944-949 (2000); and Culig, Z., et al. *Molecular endocrinology* 7, 1541-1550 (1993). Several mutations such as H875Y, V716M, and L701H/T878A have been shown to possess a broadened spectrum of ligand responsiveness, and hydroxyflutamide has previously been shown to work as an agonist for these mutants. Fenton, M. A., et al. *Clinical cancer research: an official journal of the American Association for Cancer Research* 3, 1383-1388 (1997); Hara, T., et al. *Cancer research* 63, 149-153 (2003); Veldscholte, J., et al.

Biochemistry 31, 2393-2399 (1992); and Zhao, X. Y., et al. Nature medicine 6, 703-706 (2000). Thus, it will be clinically important to test whether any of the previously identified AR mutations can also confer resistance to MDV3100, and if so, combine those mutations with F877L to predict drug sensitivity in the clinical setting.

Thus, an analysis of a patient sample which tests for the presence or absence of a mutation at position 877 in AR (e.g., AR(F877) can also, optionally, test for the presence or absence of the double mutation at positions 742 and 877 (e.g., AR(W742/T878). The presence or absence of these mutations, as described herein, has implications for patient stratification and design of drug regimens.

Antagonist-to-Agonist Switch and Alternate Therapeutic Strategies

This disclosure shows that the AR(F877) mutation not only allows resistance to MDV3100, but causes an antagonist-to-agonist switch, wherein cells expressing AR(F877) grow better or grow only in the presence of MDV3100.

A recurring theme in acquired resistance to anti-androgens is the emergence of mutations that can ultimately utilize the small molecule inhibitor as an agonist. T878A/S, W742C/L and (as shown herein) F877L (FIG. 15) promote an antagonist-to-agonist switch for hydroxyflutamide, bicalutamide and MDV3100 respectively. This is in stark contrast to the resistance observed for other classes of inhibitors, such as those targeting BCR-ABL [Gorre, M. E., et al. Science 293, 877-880 (2001)], where the mutations render the molecular targets unresponsive to the therapeutic. The fact that this switch is such a common feature to anti-androgens suggests that either 1) more potent compounds with better therapeutic indices be developed, or 2) alternate therapeutic strategies be sought. To address the first point, Sawyers and Jung recently developed a next generation anti-androgen AFN-509, that is shown to be more potent, has a higher therapeutic index and longer half-life, all of which should translate to less resistance. Clegg et al. Cancer Res. 72: 1494-1503 (2012). If future studies identify resistance-conferring mutations specific for AFN-509 despite the high therapeutic index, then alternate strategies to target AR should most likely be sought-strategies that may be less amenable to resistance by mutations in AR. One such strategy may include combining two anti-androgens (in combination or sequentially) in hopes that the likelihood of mutations conferring resistance to both be vastly reduced. Secondly, strategies such as development of AR specific peptide antagonists 1) that block the activation function 2 (AF2) function [Gao, W. Current pharmaceutical design 16, 1106-1113 (2010)], or 2) that target the N-terminal domain, in a manner similar to EPI-001 that is shown to inhibit N-terminal domain-activated reporter gene transcription, may serve as viable options. Gao, W. Current pharmaceutical design 16, 1106-1113 (2010); and Andersen, R. J., et al. Cancer cell 17, 535-546 (2010). Alternatively, rather than compromising the function of individual domains in AR, compounds that destabilize/degrade AR may be also considered.

Having shown that MDV3100 can act as an agonist of the AR pathway in clones harboring the F877L mutation, this disclosure next questioned whether this agonist switch can enhance cellular growth under androgen-depleted conditions. Interestingly, although the switch failed to drive proliferation of F877L-bearing clones in vitro, this disclosure observed a notable MDV-dependent growth in vivo. Whereas C1 (control 1) tumors showed immediate stasis upon MDV3100 treatment, the growth of clone#1 tumors [AR(F877)] was actually stimulated by MDV3100, with 11 of 15 mice treated with MDV presenting tumors compared to 2 of 15 in the vehicle group. Furthermore, clone#1 [AR(F877)] tumors continued to grow in the presence of MDV3100, in agreement with earlier observations. Collectively, these data imply that the F877L mutation likely mediates genetic and phenotypic resistance to MDV3100 by allowing mutant AR to utilize MDV3100 as an agonist. In various experiments described herein, the vehicle is DMSO.

In addition, we show here that the F877L mutation is sufficient to induce genetic and phenotypic resistance to MDV3100 in genetically engineered LNCaP cells.

The resistance-conferring role of AR(F877) is broadly applicable to several prostate cancer cell lines. Human VCaP (harboring TMPRSS2-ERG fusion and AR amplification) and murine Myc-CaP (over-expressing Myc) lines were transduced to stably express the mutant AR. Consistent with the resistance phenotype observed in LNCaP cells, both lines also presented partial resistance to MDV3100.

Furthermore, we show that AR(F877)-bearing cells are resistant to MDV3100 in the castrate setting in vivo. We observed a marked dependence on MDV3100 for growth in vivo when F877L-bearing cells were implanted into castrated male mice.

We also show that targeting CDK4/6 is a therapeutic strategy for overcoming MDV3100 resistance, using CDK4/6 inhibitors LEE011 and PD033299.

This disclosure shows that LEE011 and PD0332991 can be used as a therapeutic for AR-related diseases. This includes AR-related diseases wherein AR comprises a F877 mutation. In addition, PD0332991, LEE011 and other CDK4/6 inhibitors are useful as therapeutics against AR-related diseases wherein AR is wild-type. For example, as shown herein, a PCa line expressing WT (wild-type) AR and capable of maintaining AR signaling and expression of DHFr and TK1 under MDV3100 treatment conditions also showed strong sensitivity to CDK4/6 inhibition.

Alternate Mechanisms of Resistance to MDV3100

Two mechanisms of resistance have been implicated for MDV3100—expression of splice variants that lead to constitutive ligand-independent AR activation [Li, Y., et al. Cancer research 73, 483-489 (2013)] and activation of the PI3K signaling pathway. Mulholland, D. J., et al. Cancer cell 19, 792-804 (2011); and Carver, B. S., et al. Cancer cell 19, 575-586 (2011). However, in our work, weakly resistant clones (F877L null) did not express truncated AR isoforms (data not shown) and continued to show baseline PI3K activity (data not shown), suggesting that neither is an important mechanism of resistance in these clones. In support, ectopic expression of variant V7—a clinically relevant isoform of AR that is highly expressed in CRPC patients—in LNCaP cells failed to confer phenotypic resistance to MDV3100 despite a strong rescue in AR signaling (data not shown), supporting an earlier study. Watson, P. A., et al. Proceedings of the National Academy of Sciences of the United States of America 107, 16759-16765 (2010)]. Considering the data presented herein, but without wishing to be bound by any particular theory, this disclosure is consistent with the idea that the resistance mechanism utilized by clones lacking the F877L allele is likely to drive general resistance to anti-androgens (based on the lack of specificity to MDV3100). It is possible that mutations unique to these clones, such as a mutation in the tyrosine kinase BMX, a kinase previously shown to drive castration-resistant growth in prostate cancer [Dai, B., et al. Cancer research 70, 5587-5596 (2010)], may potentially serve as a driver of general resistance. Follow-up studies exploring the potential role of additional mutations identified by RNA-seq analysis are currently on-going.

Figure 7:
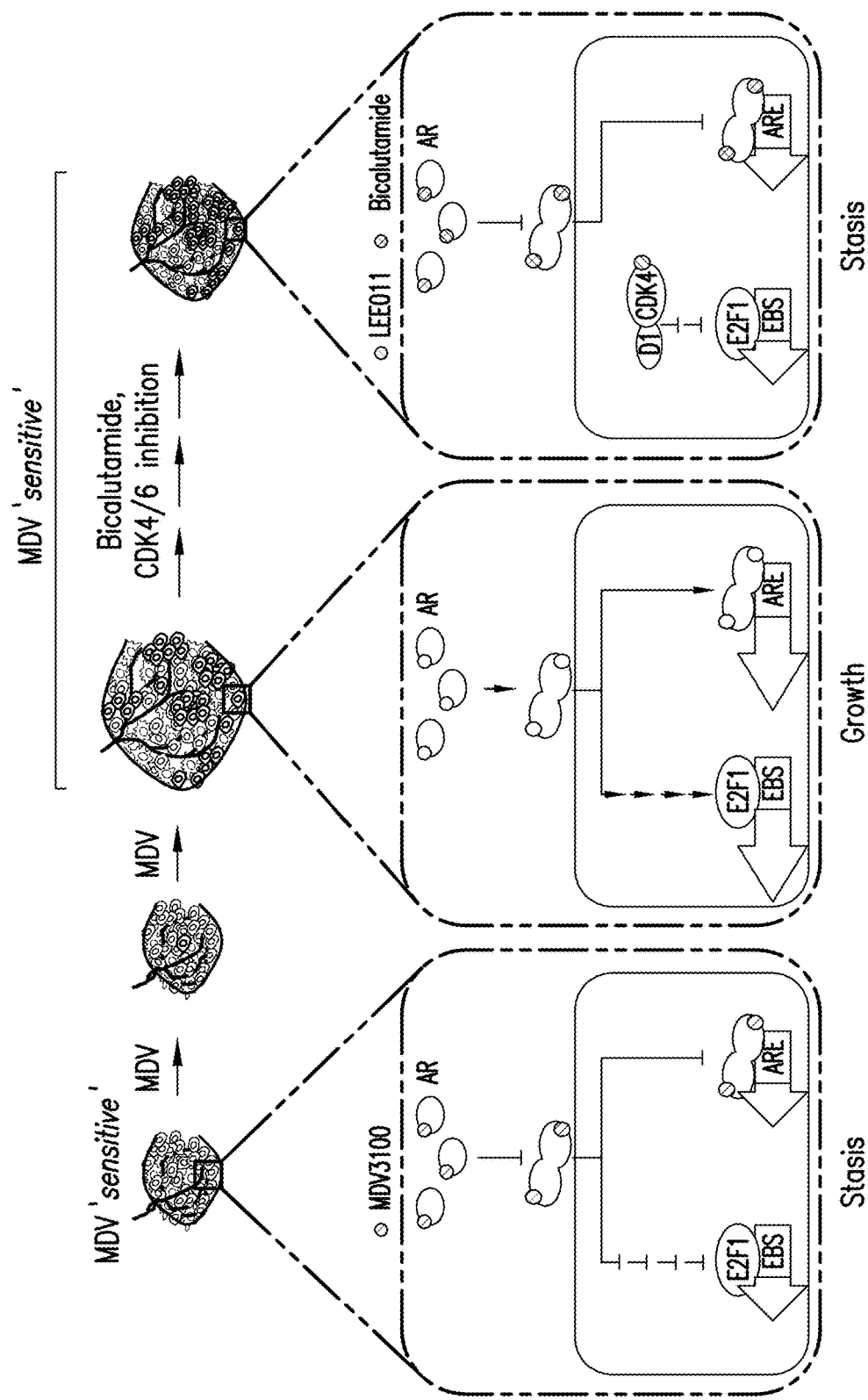
FIG. 7. Schematic representation of the therapeutic strategies that can be applied to target AR-F877L. Left, MDV3100 (brown circles) suppresses expression of E2F1 and canonical AR target genes upon binding to AR-WT (red ovals). Middle, AR-F877L (green ovals) utilizes MDV3100 as an agonist and thus maintains expression of E2F1 and canonical AR target genes. Right, targeting CDK4/6 or AR with structurally distinct anti-androgens can hinder proliferation through suppression of E2F1 and canonical AR target genes respectively. Length of grey arrow represents relative level of pathway activity. Red and blue circles represent CDK4/6 inhibitor and bicalutamide respectively. EBS, E2F1-binding sites; ARE, androgen-responsive elements.
Figure 8:
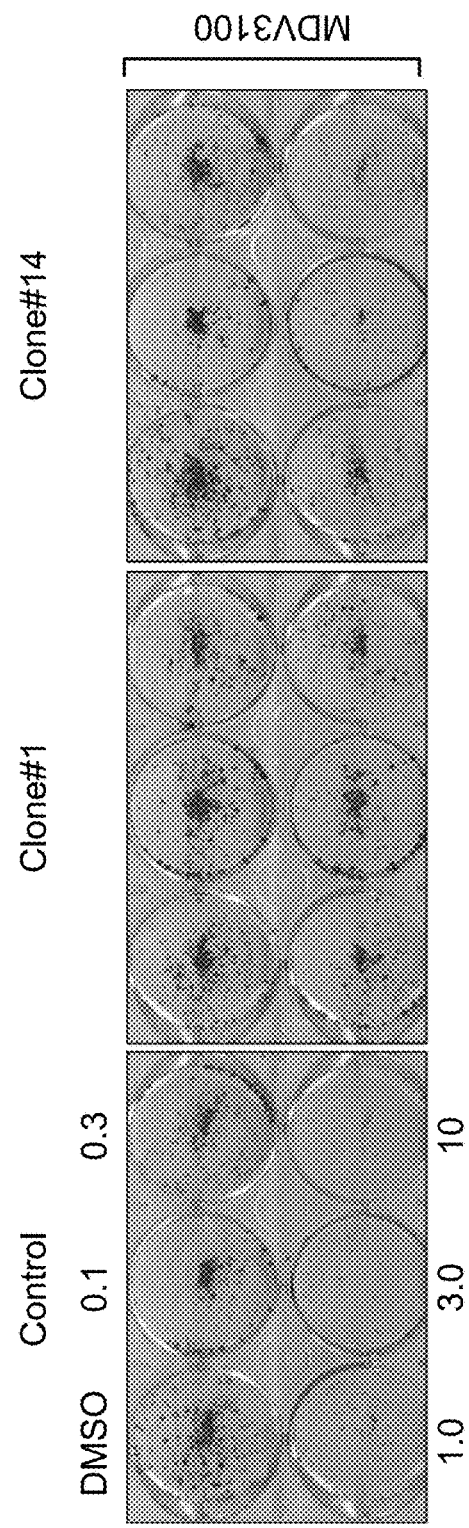
FIG. 8. Weakly and strongly resistant clones show partial resistance to MDV3100. Long-term colony formation assays for control 1 (C1, left), strongly resistant clone #1 (middle) and weakly resistant clone #14 (right) treated with various concentrations of MDV3100 (indicated in yellow font, μM).

In summary, this disclosure firmly establishes the F877L/T878A allele as a driver of genetic and phenotypic resistance to MDV3100 that retains sensitivity to bicalutamide. The clinical implications are far-reaching; 1) the mutation can serve as a biomarker used to predict drug sensitivity in patients, and 2) patients that present this mutation can alternatively be treated with bicalutamide to achieve clinical benefit (FIG. 7).

Thus, the present disclosure shows that the AR(F877) mutation and the AR(W742/T878) double mutation are both clinically relevant, conferring resistance to MDV3100, and useful for patient stratification and drug regimen design during treatment of various AR-related diseases, which are discussed in greater detail below.

Androgen Receptor-Related Diseases

The over-expression and/more mutation of androgen receptor has been indicated in several diseases, such as cancer, including prostate cancer and breast cancer, as well as other disorders such as polyglutamate disease, alopecia (e.g., androgeneic alopecia), benign prostatic hyperplasia, hirsutism, acne, spinal and muscular atrophy and Kennedy disease. See: Sawaya et al. J. Cutaneous Med. Surg. 3: 9-15 (1998); Schmidt et al. Gyn. Obstet. Invest. 22: 206-211 (1986); Giovannucci et al. Prostate 39: 130-134 (1999); Amato et al. Neurology 43: 4791 (1993); Ferlini et al. Am. J. Med. Gen. 55: 105-111 (2005); Monks et al., PNAS Nov. 2 2007; Hillmer Am. J. H. Genet. 77: 140-148 (2005); WO 2012/065051 and US 2010/0022632 and references cited therein.

AR-related diseases such as prostate diseases and breast cancer are described in more detail below.

Androgen-Receptor-Related Diseases: Prostate Diseases

By "prostate" is meant the muscular, glandular organ that surrounds the urethra of males at the base of the bladder. The prostate is a non-essential organ. The prostate helps make and store seminal fluid. In adult men, the typical prostate is about three centimeters long and weighs about twenty grams. It is located in the pelvis, under the urinary bladder and in front of the rectum. The prostate surrounds part of the urethra, the tube that carries urine from the bladder during urination and semen during ejaculation. The prostate contains many small glands which make about twenty percent of the fluid constituting semen.

By "prostate diseases" is meant any disease affecting the prostate, such as benign prostatic hyperplasia (BPH), prostatitis, and prostate cancer (PCa), including castration-resistant PCa (CRPC). Prostate diseases sometimes cause symptoms such as frequent urination, nocturia (increased urination at night), difficulty starting and maintaining a steady stream of urine, hematuria (blood in the urine), and dysuria (painful urination). Many victims of prostate disease display no symptoms.

Prostate diseases include benign prostatic hyperplasia (BPH), although the exact role of AR in BPH remains unresolved. Chatterjee Mol. Cell. Biochem. 253: 89-101 (2003); and Ho et al. Nat. Rev. Urol. 8: 29-41 (2011), and references cited therein. BPH is an increase in the size of the prostate and causes urinary obstruction, resulting in urinary incontinence. It occurs in almost 80% of men by the age of 80. BPH is often treated surgically with a transurethral resection of the prostate (TURP). This procedure is very common: 500,000 TURPs are performed in the U.S. each year and BPH is the second most common cause of surgery in males. Unfortunately, a side-effect of TURP is the elimination of the ejaculatory ducts and the nerve bundles of the penis, resulting in impotence in 90% of patients. Pharmacotherapy for the treatment of BPH is currently aimed at relaxing prostate smooth muscle (alpha$_1$ blockade) and decreasing prostate volume (androgen suppression). Clinical trials have been undertaken to evaluate selective alpha$_1$ blockers, antiandrogens, and 5-alpha reductase inhibitors for the treatment of BPH. Finasteride, a 5-alpha reductase inhibitor, has shown an ability to cause regression of the hyperplastic prostate gland in a majority of patients. Mocellini et. al. (1993) *Prostate* 22:291; and Marberger (1998) *Urology* 51:677-86.

Another prostate disease is prostatitis. Prostatitis is inflammation of the prostate. The term prostatitis refers to histological inflammation the tissue of the prostate gland. Like all forms of inflammation, it can be associated with an appropriate response of the body to an infection, but it also occurs in the absence of infection.

By "prostate cancer" or "PCa" and the like is meant a form of cancer that develops in the prostate. Androgen receptor is implicated in prostate cancer. By "cancer" is meant the abnormal presence of cells which exhibit relatively autonomous growth, so that they exhibit an aberrant growth phenotype characterized by a significant loss of cell proliferation control. One type of PCa is castration-resistant PCa (CRPC).

One embodiment of the present invention comprises methods of treating prostate cancer.

Most prostate cancers are slow growing, though some cases are aggressive. The cancer cells may metastasize from the prostate to other parts of the body, such as the bones or lymph nodes. Prostate cancer may cause pain, difficulty in urinating, problems during sexual intercourse, and/or erectile dysfunction.

The presence of prostate cancer may be indicated by symptoms, physical examination, prostate specific antigen (PSA), or biopsy.

Many different genes have been implicated in prostate cancer, including the Androgen Receptor, BRCA1 and BRCA2, HPC1, Vitamin D receptor, and TMPRSS2-ERG and TMPRSS2-ETV1/4. Tumor suppressor genes involved include P53, PTEN and KAI1, E-cadherin and CD44.

Prostate cancer is an adenocarcinoma or glandular cancer, that begins when normal semen-secreting prostate gland cells mutated into cancer cells. The region of the prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Over time, these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells that can invade other parts of the body. This invasion of the organs is called metastasis. Prostate cancer most commonly metastasizes to the bones, lymph nodes, and may invade the rectum, bladder and lower ureters.

Over-expression and/or mutation of Androgen Receptor is implicated in several other diseases, including breast cancer.

Androgen-Receptor-Related Diseases: Breast Cancer

Androgen receptor is frequently expressed in primary breast tumors; expression is estimated to be between 50% and 90%, depending on the study and the subtype of breast cancer. See: Birrell et al. J. Steroid Biochem. Mol. Biol. 52:

459-467 (1995); Moinfar et al. Cancer 98: 703-711 (2003); Buchanan et al. Cancer Res. 65: 8487-8496 (2005); Doane et al. Oncogene 25: 3994-4008 (2006); and Gonzalez-Angulo et al. Clin. Cancer Res. 15: 2472-2478 (2009). However, it is unclear if the AR acted as a tumor suppressor or an oncogene. This multifunctional role may be partly explained by the numerous pathways in which AR has been reported to be involved with, but may also from a metabolic point-of-view, in that androgens are situated between progestin and estrogen synthesis pathways which can have opposing functions. Iacopetta et al. Drug Disc. Today: Disease Mech. (2012).

Several signaling mechanisms all contribute to AR function in breast cancer. The AR is reported to exert its effects through three ways: (1) genomic signaling, where AR interacts and directly controls the expression of genes encoded in the DNA; (ii) non-genomic signaling, wherein the nuclear receptor signals via interactions with other proteins, and cross talk between the two signaling mechanisms exists but has yet to be fully understood; and (iii) singaling via cross talk with growth factors and cytokines See: Rahman et al. Trends Endocrin. Metab. 18: 371-378 (2007); and Iacopetta et al. Drug Disc. Today: Disease Mech. (2012).

AR is of potential clinical benefit in both estrogen receptor (ER) positive and negative tumors. Compared to the ER, AR contains unique functional domains with relevance to its altered role in human breast cancer. The majority of ER-positive tumors express AR, and a significant percentage of ER-negative tumors might benefit from combined targeting of AR and the ErbB2/HER2 oncogene. Signaling downstream of AR might also affect many clinically important pathways which are also emerging clinical targets in breast cancer. AR expression might also play a role during tumor progression to metastatic disease. For review, see Iacopetta et al. 2012. Drug Disc. Today: Disease Mech.

In some studies, Androgen Receptor is expressed in 60% to 85% of breast cancers, and in some cases it is more highly expressed than estrogen receptor (ER) or progesterone receptor (PR). Additionally, epidemiologic studies have found that high circulating androgen levels are associated with an increased risk of developing breast cancer, particularly among postmenopausal women. The biologic roles of androgens in the breast are incompletely understood since it is unclear whether the effects of androgens on breast cells are predominantly proliferative or anti-proliferative. Recently, the effect of androgens on breast cancer cell lines and the potential role of the androgen receptor pathway in breast cancer have been explored. Results suggest a possible anti-proliferative effect of androgen receptor stimulation and pathway activation in breast cancer.

There has been recent interest in evaluating the expression of androgen receptor among the molecularly-defined categories of invasive breast cancer, particularly among the triple negative (or basal-like) and the HER2 groups which are considered to be hormone receptor negative. However, large population based studies investigating expression of androgen receptor in relation to molecular phenotype or among women with ductal carcinoma in situ are lacking Therefore, an objective of this disclosure is to examine the expression of androgen receptor in relation to tumor stage, pathologic features and molecular phenotype using a large, well-characterized population of women with breast cancer. See Collins et al. 2011 Mod. Pathol. 24: 924-931 and references cited therein.

Collins et al. 2011 Mod. Pathol. 24: 924-931 also found that overall, 77% of the invasive breast carcinomas were androgen receptor positive. Among 2,171 invasive cancers, 64% were luminal A, 15% luminal B, 6% HER2 and 11% basal-like. The frequency of androgen receptor expression varied significantly across the molecular phenotypes ($p<0.0001$). In particular, androgen receptor expression is commonly observed in luminal A (91%) and B (68%) cancers, but is less frequently seen in HER2 cancers (59%). Despite being defined by the absence of estrogen and progesterone receptor expression and being considered hormonally unresponsive, 32% of basal-like cancers expressed androgen receptor. Among 246 cases of ductal carcinoma in situ, 86% were androgen receptor-positive, but the frequency of androgen receptor expression differed significantly across the molecular phenotypes ($p=0.001$) and high nuclear grade lesions were less likely to be androgen receptor-positive compared with lower grade lesions.

MDV3100 has been proposed as a possible treatment for at least some types of breast cancer. Naderi et al. Breast Cancer Res. 13: R36 (2011). This disclosure thus has implications for the possible use of this drug in treating this type of AR-related disease, as breast cancer patients with samples expressing AR(F877) or the double mutation of AR(W742/T878) are likely to be resistant to MDV3100.

The over-expression and/more mutation of androgen receptor has thus been indicated in several diseases, such as cancer, including prostate cancer and breast cancer, as well as other disorders such as polyglutamate disease, alopecia (e.g., androgeneic alopecia), benign prostatic hyperplasia, hirsutism, acne, spinal and muscular atrophy and Kennedy disease.

The present disclosure thus relates to AR or fragments or variants thereof comprising a mutation at F877 or a double mutation at W742/T878, optionally comprising other mutations, which are useful in patient stratification and/or in generating novel therapeutics for use in treating androgen receptor-related diseases, such as those listed above. The utility of these mutations in patient stratification and treatment is detailed below.

Treatments for Androgen-Receptor-Related Diseases

The present disclosure pertains to mutations in Androgen Receptor, which are useful for diagnosing, prognosing and treating AR-related diseases. The presence or absence of these mutations can be used for deciding among a variety of different types of disease treatments.

These treatments are useful for suppressing proliferation of cells and palliating the disease in an individual. The treatments would be delivered in an effective amount or a therapeutic amount.

As used herein, "treatment" is an approach for obtaining beneficial or desired clinical results, including, but not limited to, the suppression of proliferation of prostate cells. For purposes of this invention, beneficial or desired clinical results include, but are not limited to, alleviation of symptoms, diminishment of extent of disease, stabilization (i.e., not worsening) of state of disease, prevention of spread (i.e., metastasis) of disease, delay or slowing of disease progression, amelioration or palliation of the disease state, improvement in quality of enjoyment of life, and remission (whether partial or total), whether detectable or undetectable. "Treatment" can also mean prolonging survival as compared to expected survival if not receiving treatment. Treatments can be, for example, capable of suppressing proliferation of cells or palliating a disease.

By "suppressing proliferation of cells" means that the proliferation of cells, e.g., of the prostate gland, prostate-derived tumor cells, including metastatic tumors, or any cells expressing PSA is inhibited; or of the breast tissue, particularly breast cancer cells.

"Palliating" a disease means that the extent and/or undesirable clinical manifestations of a disease state are lessened and/or time course of the progression is slowed or lengthened, as compared to not administering polyamine analog conjugates of the present invention.

The present disclosure also pertains to treatments of an individual, using an effective amount or therapeutic amount of a treatment.

An "individual" is a vertebrate, preferably a mammal, more preferably a human. Mammals include, but are not limited to, farm animals, sport animals, rodents, primates, and pets. Preferably, the individual is known or suspected to be afflicted by a prostate disease, such as BPH, prostatitis and/or prostate cancer.

An "effective amount" or "therapeutic amount" is an amount sufficient to effect beneficial or desired clinical results. An effective amount can be administered in one or more administrations. For purposes of this invention, an effective amount of a polyamine analog conjugate is an amount that is sufficient to palliate, ameliorate, stabilize, reverse, slow or delay the progression of the disease state. A therapeutic amount of a polyamine analog conjugate of the present invention is an amount sufficient to inhibit proliferation of prostate cells. A polyamine analog conjugate is considered to be an effective agent for treating prostate diseases if it is effective against, for example, at least one type of prostate cancer cell line, even if it is not effective against a different prostate cell line.

Treatments for Androgen-Receptor-Related Diseases: Various Therapies and Treatments A variety of different treatments have been used for AR-related diseases. The present disclosure pertains to particular mutations in AR, which are useful in stratifying patients and deciding among the possible disease treatments.

For example, if a patient presents with AR(F877), a treatment comprising MDV3100 would not be useful, but a treatment not comprising MDV3100 (such as bicalutamide, LEE011, a therapeutic nucleic acid, or other treatments) could be used. If a patient presents with AR(W742/T878), a treatment comprising MDV3100 or bicalutamide would not be useful, but a treatment not comprising either of these components (such as a CDK4/6 inhibitor such as LEE011 or PD0332991, a therapeutic nucleic acid, or other treatments) could be used.

A variety of other treatments for AR-related diseases have been used which do not comprise MDV3100 and/or bicalutamide. These include surgery (e.g., radical prostatectomy), various forms of radiation therapy (e.g., brachytherapy and external beam radiation therapy), high-intensity focused ultrasound (HIFU), cryosurgery, and hormonal therapy and/or chemotherapeutic drugs. Additional therapies for AR-related diseases include, without limitation, androgen-deprivation therapies, including chemical and surgical castration, glycylcycline, benzylic oxindole pyrimidines, thieno-pyridine derivatives, desthiazolyl ritonavir, indolin-2-ones and aza-indolin-2-ones, isoflavone derivatives, nitrile derivatives, stat5 inhibitors, proton pump inhibitors, cyclopropyl dicarboxamides and analogs, 3-desoxy-2-methylene-19-nor-vitamin-D analogs, and nucleic acid therapies. US 2012/0329761; US 2012/0329771; US 2012/329774; US 2012/0329841; US 2012/0321639; US 2012/0322820; US 2012/0322834; U.S. Pat. No. 8,338,422; U.S. Pat. No. 8,338,624; U.S. Pat. No. 8,338,454; WO 2012/174095. Additional therapies are known in the art for treating Androgen Receptor (AR)-related diseases, such as prostate diseases, such as prostate cancer (PCa), including castration-resistant Pca (CRPC), and breast cancer, as well as other AR-related disorders such as polyglutamate disease, alopecia, benign prostatic hyperplasia, hirsutism, acne, spinal and muscular atrophy and Kennedy disease.

The treatments of MDV3100, bicalutamide, a CDK4/6 inhibitor such as LEE011 or PD0332991, and therapeutic nucleic acids are described in more detail below.

Treatments for Androgen-Receptor-Related Diseases: MDV3100

By "MDV3100", "MDV-3100", "Enzalutamide", "XTANDI"® (trade name), "XTANDI® capsules" and the like are meant an androgen receptor inhibitor, marketed by Astellas Pharma US, Inc., Northbrook, Ill., and Medivation Inc., San Francisco, Calif., the chemical name of which is 4-{3-[4-cyano-3-(trifluoromethyl)phenyl]-5,5-dimethyl-4-oxo-2-sulfanylideneimidazolidin-1-yl}-2-fluoro-N-methyl-benzamide. The active ingredient of XTANDI® is enzalutamide; inactive ingredients are: caprylocaproyl polyoxylglycerides, butylated hydroxyanisole, butylated hydroxytoluene, gelatin, sorbitol sorbitan solution, glycerin, purified water, titanium dioxide, black iron oxide. MDV3100 is a potent anti-androgen and lacks agonist activity. Tran et al. Science 324: 787-790 (2009). MDV3100 is indicated for the treatment of patients with metastatic castration-resistant prostate cancer who have previously received docetaxel. For references, see: Scher et al. *N. Engl. J. Med.* 2012; 367:1187-1197; and U.S. Pat. Nos. 7,709,517 and 8,183,274.

MDV3100 is chosen by Astellas Pharma and Medivation Inc. for clinical development on the basis of activity in prostate-cancer models with overexpression of the androgen receptor. Enzalutamide is distinct from the currently available antiandrogen agents in that it inhibits nuclear translocation of the androgen receptor, DNA binding, and coactivator recruitment. It also has a greater affinity for the receptor, induces tumor shrinkage in xenograft models (in which conventional agents only retard growth), and has no known agonist effects. In preclinical studies, MDV3100 works within prostate cancer cells to induce cell death, decrease proliferation and decrease tumor volume. MDV3100 competitively inhibits androgen binding to androgen receptors, inhibits androgen receptor nuclear translocation, inhibits androgen receptor interaction with DNA, and induces cell death, decreases prostate cancer cell proliferation and decreases tumor volume.

There are several contraindications, warning and precautions for MDV3100. MDV3100 can cause fetal harm when administered to a pregnant woman based on its mechanism of action. MDV3100 is not indicated for use in women. MDV3100 is contraindicated in women who are or may become pregnant.

In the randomized clinical trial, seizure occurred in 0.9% of patients on XTANDI. No patients on the placebo arm experienced seizure. Patients experiencing a seizure were permanently discontinued from therapy. All seizures resolved. Patients with a history of seizure, taking medications known to decrease the seizure threshold, or with other risk factors for seizure were excluded from the clinical trial. Because of the risk of seizure associated with XTANDI use, patients should be advised of the risk of engaging in any activity where sudden loss of consciousness could cause serious harm to themselves or others.

The most common adverse drug reactions (≥5%) reported in patients receiving XTANDI in the randomized clinical trial were asthenia/fatigue, back pain, diarrhea, arthralgia, hot flush, peripheral edema, musculoskeletal pain, headache, upper respiratory infection, muscular weakness, dizziness, insomnia, lower respiratory infection, spinal cord compression and cauda equina syndrome, hematuria, paresthesia, anxiety, and hypertension.

Drug Interactions of MDV3100. MDV3100 is a strong CYP3A4 inducer and a moderate CYP2C9 and CYP2C19 inducer in humans. Administration of strong CYP2C8 inhibitors can increase the plasma exposure to MDV3100. Co-administration of MDV3100 with strong CYP2C8 inhibitors should be avoided if possible. If co-administration of MDV3100 cannot be avoided, reduce the dose of MDV3100. Co-administration of MDV3100 with strong or moderate CYP3A4 and CYP2C8 inducers can alter the plasma exposure of MDV3100 and should be avoided if possible. Avoid CYP3A4, CYP2C9 and CYP2C19 substrates with a narrow therapeutic index, as MDV3100 may decrease the plasma exposures of these drugs. If MDV3100 is co-administered with warfarin (CYP2C9 substrate), conduct additional INR monitoring.

The recommended dose and schedule for enzalutamide is 160 mg orally once daily.

While MDV3100 has been approved for use on prostate disease patients, MDV3100 has also been posited as a potential treatment for at least some types of breast cancer. Naderi et al. Breast Cancer Res. 13: R36 (2011).

Although MDV3100 has shown tremendous efficacy in clinical trials, many who initially responded favorably have since developed resistance to this second-generation antiandrogen. Kim et al. Curr. Treat. Opt. Oncol. 13: 189-200 (2012). This disclosure shows the generation of a model of spontaneous resistance in LNCaP cells after prolonged treatment with MDV3100 in vitro. Examination of these lines revealed a highly recurrent F877L/T878A mutation in the ligand-binding pocket of AR that endows an antagonist-to-agonist switch highly specific for MDV3100. This novel mutation drives genetic and phenotypic resistance specifically to MDV3100, while remaining sensitive to the cytostatic influence of bicalutamide.

Thus, this disclosure shows that a mutation at F877 or a double mutation at W742/T878 in AR causes resistance to MDV3100. The F877 mutation can actually cause an antagonist-to-agonist switch for MDV3100. Cells displaying an AR(F877) mutation thus cannot be treated with MDV3100, but remain susceptible to other treatments which do not comprise MDV3100, such as bicalutamide.

Other Treatments for Androgen-Receptor-Related Diseases: Bicalutamide

By "Bicalutamide" and its tradenames "CASODEX", "SANDOZ BICALUTAMIDE", "COSUDEX", "CALUTIDE", "KALUMID" and the like are meant the nonsteroidal antiandrogen with the chemical name of N-[4-cyano-3-(trifluoromethyl)phenyl]-3-[(4-fluorophenyl)sulfonyl]-2-hydroxy-2-methylpropanamide. See: Furr. *Eur. Urol.* 29 Suppl 2: 83-95(1996); Furr. *Urology* 47 (1A Suppl): 13-25; discussion 29-32 (1996); Schellhammer et al. *Urology* 50 (3): 330-6 (1997); Waller et al. *J. Mol. Endocrinol.* 24 (3): 339-51 (2000); Müderris et al. *Gynecol. Endocrinol.* 16 (1): 63-6 (2002); Schellhammer. *Expert Opin Pharmacother* 3 (9): 1313-28 (2002); Fradet et al. *Expert Rev Anticancer Ther* 4 (1): 37-48 (2004); Chen et al. *Mol. Interv.* 5 (3): 173-88 (2005); Klotz *Urol. Clin. North Am.* 33 (2): 161-6, v-vi (2006); *Journal of cancer research and clinical oncology* 132 Suppl 1: S7-16 (2006); and Levine et al. *Cancer* 110 (11): 2448-56 (2007).

Bicalutamide belongs to a group of medications known as nonsteroidal antiandrogens. Another nonsteroidal antiandrogen is flutamide. Nonsteroidal antiandrogens such as bicalutamide block the effect of the male hormone testosterone in the body.

Bicalutamide is used in combination with another treatment that reduces the amount of testosterone in the body (either with medications called luteinizing hormone releasing hormone analogues (LHRH) or with surgery to remove the testicles) for the treatment of late stage (metastatic) prostate cancer. Bicalutamide belongs to a group of medications known as nonsteroidal antiandrogens.

Another nonsteroidal antiandrogen is flutamide. Nonsteroidal antiandrogens such as bicalutamide block the effect of the male hormone testosterone in the body.

Bicalutamide is used in combination with another treatment that reduces the amount of testosterone in the body (either with medications called luteinizing hormone releasing hormone analogues (LHRH) or with surgery to remove the testicles) for the treatment of late stage (metastatic) prostate cancer.

While it has an inhibitory effect on AR in hormone sensitive prostate cancer, it fails to suppress AR when cancer becomes hormone refractory. Two weaknesses of current antiandrogens are blamed for the failure to prevent prostate cancer progression from the hormone sensitive stage to the hormone refractory disease and to effectively treat hormone refractory prostate cancer. One is their weak antagonistic activities and the other is their strong agonistic activities when AR is overexpressed in hormone refractory prostate cancer. Therefore, better AR inhibitors with more potent antagonistic activities and minimal agonistic activities are needed to delay disease progression and to treat the fatal hormone refractory prostate cancer.

Nonsteroidal anti-androgens, such as bicalutamide, have been preferred over steroidal compounds for prostate cancer because they are more selective and have fewer side effects. This class of compounds has been described in many patents such as U.S. Pat. No. 4,097,578, U.S. Pat. No. 5,411,981, U.S. Pat. No. 5,705,654, PCT International Applications WO 97/00071 and WO 00/17163, and U.S. Published Patent Application No. 2004/0009969, all of which are hereby incorporated by reference.

Bicalutamide has been clinically used for many years as a monotherapy or in combination with castration to block androgen action. However, in the setting of CRPC, bicalutamide undergoes an antagonist-to-agonist switch, paradoxically enhancing AR signaling activity. Culig. Et al. Brit. J. Cancer 81: 242-251 (1999).

It is known that the W742/T878 double mutation in AR renders cells resistant to bicalutamide. This disclosure also shows that this double mutation renders cells resistant to MDV3100.

This disclosure also shows that the F877 mutation in AR renders cells resistant to MDV3100, but not bicalutamide. Thus, bicalutamide can be used as a therapeutic against cells with the AR(F877) mutation.

In addition to bicalutamide, other therapies for androgen receptor-related diseases exist which do not comprise MDV3100 and are described below.

Other Treatments for Androgen-Receptor-Related Diseases: LEE011

LEE011 (also designated Lee 011, Lee011, LEE-011, and LEE 011) (Novartis and Astex Pharmaceuticals) is a new oral drug designed to inhibit the activity of CDK4/6. See: PCT/US2007/069595; WO 2010/020675; and WO2011/130232.

The chemical name of LEE011 is 7-Cyclopentyl-2-(5-piperazin-1-yl-pyridin-2-ylamino)-7H-pyrrolo[2,3-d]pyrimidine-6-carboxylic acid dimethylamide. The structure of LEE011 is as follows:

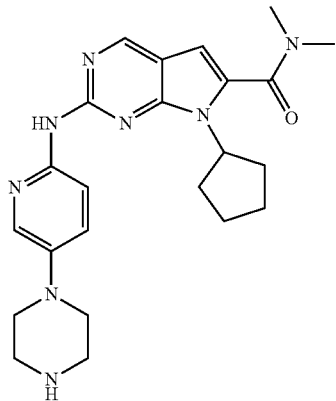 [SMILES: CN(C)C(=O)c1cc2cnc(Nc3ccc(N4CCNCC4)cn3)nc2n1C1CCCC1]

LEE011 induces complete dephosphorylation of Rb and G1 arrest in cancer cells. CDK4/6 is involved in the process that allows both normal and cancer cells to divide and multiply. Cancer cells are often driven to divide and multiply by abnormalities that increase the activity of CDK4. Hence there is hope that blocking the activity of CDK4 may slow the growth of some cancers, including breast and prostate cancers.

This disclosure shows that the F877 mutation in AR renders cells resistant to MDV3100. The W742/T878 double mutation is known to render cells resistant to bicalutamide and shown here to render cells resistant to MDV3100. However, as shown herein, cells with either the F877 mutation or W742/T878 double mutation in AR remain sensitivity to the unrelated cytostatic agent LEE011.

In addition, LEE011, PD0332991 and other CDK4/6 inhibitors are useful as therapeutics against AR-related diseases wherein AR is wild-type. For example, as shown herein, a PCa line expressing WT (wild-type) AR and capable of maintaining AR signaling and expression of DHFr and TK1 under MDV3100 treatment conditions also showed strong sensitivity to CDK4/6 inhibition.

LEE011 can also be used as part of a combination therapy with one or more other therapies and/or treatments in methods of treatment of AR-related diseases.

Other Treatments for Androgen-Receptor-Related Diseases: PD0332991

CDK4/6 inhibitor PD-0332991 [or PD0332991 or PD033299] is a potent cytostatic agent that is in phase II clinical trials for multiple malignancies, including breast cancer. Finn et al. 2009 Breast Cancer Res. 11: R77; Thangavel et al. 2011 End. Relat. Cancer 18: 333-45; Dean et al. 2010 Oncogene 29: 4018-32; and Dean et al. 2012 Cell Cycle 11: 2756-2761.

This disclosure shows that PD0332991 can be used as a therapeutic for AR-related diseases. This includes AR-related diseases wherein AR comprises a F877 mutation. In addition, PD0332991, LEE011 and other CDK4/6 inhibitors are useful as therapeutics against AR-related diseases wherein AR is wild-type. For example, as shown herein, a PCa line expressing WT (wild-type) AR and capable of maintaining AR signaling and expression of DHFr and TK1 under MDV3100 treatment conditions also showed strong sensitivity to CDK4/6 inhibition.

Other Treatments for Androgen-Receptor-Related Diseases: Therapeutic Nucleic Acids and Derivatives Several groups have shown therapeutic nucleic acids useful for treating androgen receptor-related diseases. These include antisense nucleic acids, morpholinos, siRNAs, etc.

WO97/1 1 170 reports on a method of treating a patient diagnosed as having benign prostatic hyperplasia or a prostate cancer comprising administering an antisense oligonucleotide which selectively hybridizes to the androgen receptor mRNA. Three antisense oligonucleotide sequences of between 27-29 nucleotides are disclosed. U.S. Pat. No. 6,733,776 and EP 0 692 972 report on a method for treating androgenic alopecia by applying liposomes comprising an antisense nucleic acid that hybridizes to an androgen receptor gene. No antisense molecules with specific sequences and targeting the androgen receptor are provided. US 2005/0164970 reports on a method of treating prostate cancer using siRNA complexes targeting the androgen receptor mRNA. WO 2005/027833 reports on a method of treating prostate cancer comprising of administering a morpholino oligonucleotide of between 12-40 morpholino sub-units in length to the patient. WO 2001/083740 reports on an antisense compound having an uncharged morpholino backbone of between 18 to 20 contiguous units which targets the human androgen receptor. Morpholino antisense compounds work via binding to the nucleic acid target to block access to the mRNA by other molecules, such as molecules involved in mRNA splicing or translation initiation. U.S. Pat. No. 7,067,256 reports on a ribozyme which apparently mediates inactivation of the androgen receptor. A 19 nucleotide RNA molecule antisense to a corresponding region of the androgen receptor mRNA is provided. WO 2012/065051 describes siRNAs to androgen receptor.

This disclosure shows that cells with a F877 mutation or W742/877 double mutation in AR are resistant to MDV3100. However, without wishing to be bound by any particular theory, this disclosure posits that therapeutics which do not comprise MDV3100, such as therapeutic nucleic acids (e.g., siRNAs) may be effective against these cells, provided. that the therapeutics can be delivered to the cells in sufficient quantities.

In addition, we show herein that targeting CDK4/6 is a therapeutic strategy for overcoming MDV3100 resistance, using CDK4/6 inhibitors LEE011 and PD033299.

Since we further demonstrate that the F877L variant retains sensitivity to bicalutamide, combination therapy with structurally distinct anti-androgens either in parallel or in series together with androgen deprivation may provide an appealing therapeutic strategy for combating AR resistance mechanisms in the clinic.

In addition, targeting CDK4/6 with a CDK4/6 inhibitor is a valid therapeutic strategy for an Androgen Receptor-related disease, whether the AR is WT or has a mutation such as F877.

AR(F877) Polynucleotide

In another aspect, the present disclosure provides a polynucleotide or an antisense polynucleotide that comprises at least 15 consecutive nucleotides (including 0, 1, 2 or 3 mismatches) having the sequence of and/or capable of detectably hybridizing to a sequence encoding at least 5 contiguous amino acids of SEQ ID NO: 54, including position 877, wherein the amino acid at position 877 is an amino acid other than phenylalanine (F), wherein hybridization is under conditions that include a wash in 0.1×SSC and 0.1% SDS at 50° C. for 15 minutes. Such a polynucleotide can be useful for detecting the presence of an AR(F877) polynucleotide within a cell or tissue or patient, or for producing a therapeutic nucleic acid to AR(F877). In various aspects, the therapeutic nucleic acid is RNA, DNA, siRNA (small or short interfering RNA, with or without various modifications and/or endcaps), RNA-DNA hybrid, DNA-RNA chimera (which is similar to a siRNA except that a portion of the dsRNA is replaced by dsDNA), LNA (locked nucleic acid), TNA (threose nucleic acid), GNA (glycol nucleic acid), morpholino, anti-sense oligonucleotide, shRNA, sisiRNA (small internally segmented RNA), aiRNA (assymetrical interfering RNA), or a combination of any of the above (e.g., wherein the components of the nucleic acid comprise one or more of the above, such as a RNA with some nucleotides substituted with RNA, GNA, LNA, morpholino, etc.), the like. In various embodiments, the polynucleotide and/or antisense polynucleotide are single-stranded or double-stranded, and/or modified, e.g., by 2'-OMe, 2'-F, and/or 2'-MOE, and/or by modification and/or replacement of the phosphates (e.g., by methylated phosphate, arsenic, selenium, etc.). Also provided are expression vectors comprising any of the foregoing polynucleotides, and host cells transformed or transfected with such expression vectors.

In brief, thus, the present disclosure pertains to particular mutations in AR which are useful in diagnosing, prognosing and treating (e.g., design a course of treatment) for patients with AR-related diseases.

Below, methods of detecting the particular AR mutation and patient stratification are described in more detail.

Methods of Patient Stratification and Methods of Detecting AR(F877) and Stratifying Patients Within further aspects, the present disclosure provides methods of detecting the presence or absence of a mutation at position F877 in AR in a sample (e.g., a cell or tissue sample) in or from a patient (e.g., a patient afflicted with, suffering from or exhibiting at least one clinical sign or symptom of, at risk of or prone to developing or suspected of having an AR-related disease). The mutation at F877 in AR is clinically relevant, as patients presenting such a mutant AR should not be treated with MDV3100, but rather should be treated with a treatment which does not comprise MDV3100 (e.g., bicalutamide or a CDK4/6 inhibitor such as LEE011 or PD0332991).

It is noted that the cells within a sample may be heterogeneous; some may express AR(F877), while others may express WT (wild-type) AR and/or other mutant AR. In various aspects described herein, the present disclosure pertains to methods of detecting a mutation at position F877 in AR of a sample which may comprise a mixture of AR(F877), WT AR and/or other mutant ARs. In some aspects, the method is able to determine the ratios of the mixture of AR(F877), WT AR and/or other mutant ARs. In some samples, the AR(F877) may be in a minority of AR-expressing cells.

In various aspects, the present disclosure provides a method of detecting a mutation at position F877 in an AR polynucleotide or polypeptide in a sample (e.g., from a patient), the method comprising the steps of: (a) obtaining a sample (e.g., a biological sample, tissue sample, cell sample, etc.) comprising AR from the patient; and (b) determining the sequence of the AR polynucleotide or polypeptide or a portion thereof to determine if the AR comprises a mutation at position F877 (wherein the position of the amino acids is in accordance with the numbering of SEQ ID NO: 54). In various aspects, the sample is still within and/or a part of the patient. In various aspects, the patient is afflicted with, suffering from or exhibiting at least one clinical sign or symptom of, and/or at risk of or prone to developing or suspected of having an AR-related disease. The method optionally pertains to diagnosing, prognosing and/or treating a patient and optionally further comprises the additional step: (c) administering or recommending the administration of a therapeutic composition comprising MDV3100 if a AR does not comprise a mutation at F877; or administering or recommending the administration of a therapeutic composition not comprising MDV3100 if a AR does comprise a mutation at F877. In various aspects, the therapeutic composition not comprising MDV3100 is bicalutatmide or a CDK4/6 inhibitor such as LEE011 or PD0332991, or a therapeutic nucleic acid. In various aspects, if the sample is determined to comprise a mixture of cells expressing AR(F877), WT AR and/or other mutant ARs, several steps may be necessary to attack the different types of cells within the mixture.

In addition, ratios of WT and various mutant AR-presenting cells may change as sub-populations of cells are killed off or possibly activated by therapies, and resistant clones arise. Thus, steps (a), (b) and (c) may be repeated.

For example, methods of determining if the amino acid at position 877 in AR is phenylalanine and stratifying patients can be done after 1 or more rounds of therapy. A tumor or other diseased tissue may be heterogeneous, comprising multiple types of AR [e.g., WT AR, and/or AR(F877) and/or other mutants]. The ratios of these sub-populations of cells may change as some cells or killed or activated by a therapeutic. Experiments disclosed herein show that extended exposure of LNCaP cells to MDV3100 yielded populations of clones resistant to MDV3100. Other studies have shown resistance appearing to MDV3100 or other disease treatments, or an enrichment of mutant, resistant cells. It is noted that it may be unclear if the resistance is pre-existing (e.g., in a minor sub-population of cells) or is acquired in response to treatment. After one or more round of therapy, thus, steps (a) and (b) can be repeated to determine the characteristics of the remaining cells, and step (c) may be modified to select a therapeutic appropriate for attacking the remaining cells.

In various aspects, the method of determining if the amino acid at position 877 in AR is phenylalanine (F) includes without limitation and inter alia, use of nucleic acid sequencing (e.g., the methods of DNA sequencing, RNA-seq, protein sequencing, whole transcriptome sequencing, or other methods known in the art), or using an antibody or nucleic acid specific to AR(F877).

In various aspects, the nucleic acid sequencing pertains to sequencing of a nucleic acid that can encode the AR or a portion thereof comprising or spanning position F877, or that is complementary to a nucleic acid which encodes the AR or the portion thereof.

In various aspects, the method of determining if the amino acid at position 877 in AR is phenylalanine (F) includes without limitation and inter alia the use of an antibody or fragment or variant thereof specific to AR(F877) [e.g., which binds to or recognizes AR(F877) but not WT AR]. In various aspects, the present disclosure provides a method for detecting AR(F877) expression in a sample (e.g., from a patient), the method comprising the steps of: (a) contacting a sample with an antibody or an antigen-binding fragment thereof as described above, under conditions and for a time sufficient to allow formation of an antibody/AR(F877) complex; and (b) detecting the level of antibody/AR(F877) complex.

In various aspects, the method of determining if the amino acid at position 877 in AR is phenylalanine (F) includes without limitation and inter alia, use of a nucleic acid specific to AR(F877) [e.g., which binds to or recognizes AR(F877) but not WT AR].

Within still other aspects, the present disclosure provides a method for detecting AR(F877) expression in a sample, comprising: (a) contacting a sample with a nucleic acid or fragment or variant thereof specific to AR(F877) under conditions and for a time sufficient to allow hybridization of the nucleic acid with a nucleic acid in the sample; and (b) detecting the level of hybridization The amount of AR(F877) antisense polynucleotide or polynucleotide in the sample that hybridizes to the polynucleotide or antisense polynucleotide may be determined, for example, using sequencing, polymerase chain reaction or a hybridization assay.

Also provided are methods for modulating a proliferative response in a cell, comprising the step of contacting a cell with an agent that modulates AR(F877) activity.

Within further aspects, methods are provided for modulating differentiation of a cell, comprising the step of contacting a cell with an agent that modulates AR(F877) activity.

The present disclosure further provides methods for modulating cell survival, comprising the step of contacting a cell with an agent that modulates AR(F877) activity.

Thus, in various aspects, the present disclosure pertains to various methods of detecting or AR(F877) and stratifying patients who do or do not express this polypeptide.

In various aspects, the method of determining if the amino acid at position 877 in AR is phenylalanine (F) includes without limitation and inter alia, use of nucleic acid sequencing (e.g., the methods of DNA sequencing, RNA-seq, protein sequencing, whole transcriptome sequencing, or other methods known in the art), or using an antibody or nucleic acid specific to AR(F877). For various references related to sequencing, see: Morin et al. Nature 476: 298-303 (2011); Kridel et al. Blood 119: 1963-1971 (2012); Ren et al. Cell Res. 22: 806-821 (2012) and references cited therein.

In short, a variety of methods are available for determining if sample from a patient comprises a AR with a particular mutation. These various mutations are useful for patient stratification and for the design of treatment regimens.

The novel and clinically relevant AR mutation at F877 is also useful in that AR polypeptides comprising this mutation, antibodies to these polypeptides and polynucleotides encoding them can be used to generate or screen for new therapeutics.

Use of AR(F877) to Generate and Screen for New Therapeutics

The mutation at position F877 allows AR to be resistant to MDV3100, and even causes an antagonist-to-agonist switch for this drug. There thus exists the need for novel therapeutics which interact with AR(F877) and are useful for treating patients of AR-related diseases who have such a mutation in AR.

The present disclosure further provides, within other aspects, methods for screening a molecule (e.g., a potential therapeutic) for the ability to interact with AR(F877), comprising the steps of: (a) contacting a candidate molecule with a AR(F877) polypeptide under conditions and for a time sufficient to permit the candidate molecule and polypeptide to interact; and (b) detecting the presence or absence of binding of the candidate molecule to the polypeptide and/or ability to interfere with or decrease at least one activity of the polypeptide. The step of detecting may, for example, comprise the use of an AR(F877) and an AR reporter, e.g., a polynucleotide comprising an ARE [DNA sequence to which WT or AT(F877) bind], promoter, and a reporter gene (e.g., luciferase). The step of detecting may comprise, for example, determining if the candidate molecule interferes with or decreases the ability of the AR(F877) to drive expression from the AR reporter. The step of detecting may comprise, for example, an affinity purification step, a yeast two hybrid screen or a screen of a phage display library.

In some aspects, the methods of screening for novel therapeutics involve the use of an AR(F877) polypeptide or fragment or variant thereof comprising or spanning the amino acid at position 877. This polypeptide can be produced in any manner known in the art, including expression from a polynucleotide encoding the polypeptide.

The present disclosure encompasses methods of producing a AR(F877) polypeptide.

The present disclosure further provides, within other aspects, methods for producing a AR(F877) polypeptide, comprising the steps of: (a) culturing a host cell as described above under conditions that permit expression of the AR(F877) polypeptide; and (b) isolating AR(F877) polypeptide from the host cell culture.

Many methods can be readily devised for using a mutant AR(F877) in screening for drugs that sensitize this mutant AR.

Two methods that this disclosure has applied include 1) transactivation and 2) gene expression analysis to determine if compounds that target the AR pathway can be used as inhibitors of mutant AR function. Both methods are clearly outlined in methods section. One method is detailed in Example 7.

Briefly, for transactivation assays, AR reporter, a control plasmid and WT or mutant AR(F877) plasmids are co-transfected prior to treatment with control solvent (such as DMSO), agonist or antagonist of interest. The AR reporter comprises, for example, an ARE (Androgen Response Element sequence to which AR binds), a promoter, and a reporter gene such as luciferase. Following treatment, a product of the reporter gene (e.g., bioluminescence) is quantitated. It is expected that WT AR will activate the AR reporter in the presence of and agonist (e.g., R1881) and the signal should be sufficiently suppressed in the presence of an antagonist, such as MDV3100. However, for AR (F877), it is expected that there to be a sufficient activation of AR-reporter activity in the presence of agonist and antagonist such as MDV3100. An ideal novel antagonist will sufficiently block AR(F877) function—in a manner similar to bicalutamide.

In addition to transactivation assays, gene expression analysis of canonical AR genes, such as KLK3, TMPRSS2, NKX3-1 and SLC45A3, can also be monitored. This experiment is similar to the experiment outlined elsewhere herein, except that MDV3100 may be substituted for a novel compound(s). It is expected that whereas MDV3100 may be used as an agonist to rescue signaling, a novel compound may be effective in maintaining suppression of signaling activity in F877L-AR bearing cells.

Thus, the AR(F877) has been and can be used to screen for novel drugs and therapeutics which affect this mutant AR.

Antibodies to AR(F877)

An antibody can be developed which bind specifically to AR(F877) but which do not bind to AR lacking a mutation at F877 (thus, a AR, fragment or variant which has a phenylalanine at position 877).

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J. Immunol. 1996; 26 (3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework regions and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH—terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

Antibodies, small molecules, siRNAs which specifically target AR(F877) can therefore be devised using AR(F877).

AR(F877) Polynucleotide

The present disclosure also pertains to AR(F877) polynucleotides. These polynucleotides can be used to encode (e.g., express) a AR(F877) polypeptide, or incorporated into a therapeutic nucleic acid [e.g., a siRNA or the like to AR(F877)].

In one aspect, the present disclosure provides a polynucleotide or an antisense polynucleotide that comprises at least 15 consecutive nucleotides (including 0, 1, 2 or 3 mismatches) having the sequence of and/or capable of detectably hybridizing to a sequence encoding at least 5 contiguous amino acids of SEQ ID NO: 54, including position 877, wherein the amino acid at position 877 is an amino acid other than phenylalanine (F), wherein hybridization is under conditions that include a wash. Such a polynucleotide can be useful for detecting the presence of an AR(F877) polynucleotide within a cell or tissue or patient, or for producing a therapeutic nucleic acid to AR(F877). Also provided are expression vectors comprising any of the foregoing polynucleotides, and host cells transformed or transfected with such expression vectors.

Another embodiment of the disclosure provides an isolated Androgen Receptor polynucleotide, wherein the isolated polynucleotide or its complement encodes at least 5, 6, 7, 8, 9, 10, 11, 12, 13, 14 or 15 contiguous amino acids of SEQ ID NO: 2, wherein the at least 5, 6, 7, 8, 9, 10, 11, 12, 13, 14 or 15 contiguous amino acids comprise or span position 877 of SEQ ID NO: 2, and wherein the amino acid at position 877 is not Phenylalanine (F), and wherein, optionally, the amino acid at position 877 is not threonine (T), the amino acid at 875 is not histidine (H), the amino acid at position 716 is not valine (V), and/or the amino acid at position at 742 is not tryptophan (W).

Another embodiment of the disclosure provides an expression construct (or vector) comprising an isolated Androgen Receptor polynucleotide as described above.

Another embodiment of the disclosure provides a host cell comprising an isolated Androgen Receptor polynucleotide as described above.

Another embodiment of the disclosure provides a host cell comprising a construct which comprises a promoter; and an isolated Androgen Receptor polynucleotide as described above.

Another embodiment of the disclosure provides a polynucleotide which encodes a mutant Androgen receptor comprising an amino acid sequence of SEQ ID NO: 2 except the encoded mutant Androgen receptor protein contains an leucine (L) at position 877 of SEQ ID NO: 2.

Another embodiment of the disclosure provides a construct comprising: a promoter; and a polynucleotide segment encoding a mutant Androgen receptor or a fragment thereof, wherein the amino acid sequence of the Androgen Receptor is shown in SEQ ID NO: 2, wherein said sequence contains a mutation at amino acid position 877 of SEQ ID NO: 2 such that the amino acid at position 877 is not phenylanine (F), and wherein, optionally, the amino acid at position 877 is not threonine (T), the amino acid at 875 is not histidine (H), the amino acid at position 716 is not valine (V), and/or the amino acid at position at 742 is not tryptophan (W), and wherein the sequence of the fragment comprises at least 5 contiguous amino acids of SEQ ID NO: 2 and comprises position 877, wherein the polynucleotide segment is located downstream from the promoter, wherein transcription of the polynucleotide segment initiates at the promoter.

Another embodiment of the disclosure provides an isolated polynucleotide wherein the isolated polynucleotide or its complement encodes at least 10 contiguous amino acids of SEQ ID NO: 54, wherein the at least 10 contiguous amino acids comprise position 877 of SEQ ID NO: 54, and wherein the amino acid at position 877 is substituted or deleted or is not Phenylalanine (F).

Another embodiment of the disclosure provides an isolated polynucleotide wherein the isolated polynucleotide or its complement encodes at least 15 contiguous amino acids of SEQ ID NO: 54, wherein the at least 15 contiguous amino acids comprise position 877 of SEQ ID NO: 54, and wherein the amino acid at position 877 is substituted or deleted or is not Phenylalanine (F).

Another embodiment of the disclosure provides an isolated polynucleotide wherein the isolated polynucleotide or its complement encodes at least 20 contiguous amino acids of SEQ ID NO: 54, wherein the at least 20 contiguous amino acids comprise position 877 of SEQ ID NO: 54, and wherein the amino acid at position 877 is substituted or deleted or is not Phenylalanine (F).

Another embodiment of the disclosure provides an expression construct comprising any isolated polynucleotide as described herein.

Another embodiment of the disclosure provides a host cell comprising any isolated polynucleotide as described herein.

Another embodiment of the disclosure provides a host cell comprising a construct which comprises a promoter; and any polynucleotide as described herein.

Another embodiment of the disclosure provides an isolated polynucleotide encoding: a mutant Androgen receptor polypeptide or a fragment thereof, wherein the amino acid sequence of the Androgen receptor is shown in SEQ ID NO: 54, wherein said sequence contains a mutation at amino acid position 877 of SEQ ID NO: 54 such that the amino acid at position 877 is substituted or deleted or is not phenylanine (F), and wherein the sequence of the fragment comprises at least 5 contiguous amino acids of SEQ ID NO: 54 and comprises position 877.

Another embodiment of the disclosure provides a polynucleotide which encodes a mutant Androgen receptor protein comprising an amino acid sequence of SEQ ID NO: 54 except the encoded mutant Androgen receptor protein contains a leucine (L) at position 877 of SEQ ID NO: 54.

Thus, in various aspects, the present disclosure pertains to a polynucleotide encoding an AR(F877) or fragment or variant thereof. Below the disclosure presents in further detail experimental data pertaining to this mutation.

Androgen Receptor with F877 Mutation

An object of this disclosure is to provide tools and methods for diagnosing, prognosing and treating prostate diseases such as prostate cancer (PCa), including castration-resistant Pca (CRPC). This and other objections of the disclosure are provided by one or more of the embodiments described below.

In various aspects, the present disclosure pertains to AR(F877), which is a polypeptide or the like comprising Androgen Receptor or a fragment thereof comprising position 877, wherein the amino acid at position 877 is an amino acid other than phenylalaline (F). In some aspects, the amino acid at position 877 is leucine (L). In various aspects, the AR(F877) polypeptide optionally has mutations at other positions, such that the amino acid at position 877 is not threonine (T), the amino acid at 875 is not histidine (H), the amino acid at position 716 is not valine (V), and/or the amino acid at position 742 is not tryptophan (W). In additional aspects, the present disclosure pertains to AR(W742/T878), which is a polypeptide or the like comprising Androgen Receptor or a fragment thereof comprising positions 742 and 877, wherein the amino acid at position 742 is not tryptophan (W) and the amino acid at position 877 is not threonine (T).

In various aspects, the present disclosure provides a method for detecting AR(W742/T878) expression in a patient), the method comprising the step of: determining if the amino acids at positions 742 and 877 of an androgen receptor or fragment thereof in the patient are, respectively, tryptophan (W) and threonine (T). In various aspects, the method further comprises the steps of recommending the administration of and/or administering to the patient: (a) bicalutamide or MDV3100 if the amino acids at positions 742 and 877 are, respectively, tryptophan (W) and threonine (T); or (b) a prostate disease treatment other than bicalutamide or MDV3100 if the amino acids at positions 742 and 877 are not, respectively, tryptophan (W) and threonine (T).

This disclosure utilizes the LNCaP model—a model previously used to identify a clinically relevant W742C mutation that confers resistance to bicalutamide [Hara et al. Cancer Res. 63: 149-153 (2003)]—to identify and functionally confirm the role of the F877L/T878A mutation in AR as an antagonist-to-agonist switch for MDV3100. Through gene expression and phenotypic analysis, this disclosure shows that the agonist switch conferred by the F877L/T878A mutant AR is highly selective for MDV3100, as sensitivity is maintained to bicalutamide. This would imply that patients that present this mutation—either pre-existing or acquired in response to therapy—will show rapid clinical progression of the disease during treatment with MDV3100, but may respond favorably to bicalutamide or potentially other classes of anti-androgens (FIG. 7). Screening patients to identify this mutation, either prior to therapy or following onset of resistance, will aid in predicting drug sensitivity and guide alternative clinical management strategies.

EXAMPLES

Example 1. Materials and Methods

Methods
Cell Culture
LNCaP-FGC and PC3 cells were maintained in RPMI 1640 media with 10% FCS (Hyclone) or 10% CSS (Omega, cat# fb-04) as indicated. 22Rv1 cells were maintained in RPMI 1640 media with 10% FCS. VCaP cells were maintained in DMEM media with 10% FCS or 10% CSS. Myc-CaP cells were maintained in DMEM media with 10% FCS. 293FT cells were maintained in DMEM supplemented with 10% FCS and 1×NEAA. All lines, except Myc-CaP cells, were obtained from the American Type Culture Collection and cells were tested and authenticated by single-nucleotide polymorphism fingerprinting. Myc-CaP cells were kindly provided by Dr. Charles Sawyers and were not further tested or authenticated.

Generation of Spontaneous MDV3100 Resistant LNCaP Clones In Vitro 2 million LNCaP cells were seeded into four 150 $cm^2$ tissue culture dishes in phenol red-free RPMI 1640 media supplemented with 10% FCS. The next day, DMSO and ethanol (control 1, C1), DMSO and 1.0 nM R1881 (control 2, C2), 1 µM MDV+1.0 nM R1881 (control 3, C3), and 1 µM MDV3100 were added to dishes 1 to 4 respectively. Cells were re-seeded into 150 $cm^2$ dishes supplemented with the appropriate treatments once each week. Media and compound was replaced for dish 4 once every week. Once resistant clones emerged, media was aspirated from dish 4. Trypsin soaked 3 mm sterile cloning discs (Scienceware, cat#17-2.X) were used to overlay the resistant clones and following a 1-2 min incubation, cloning discs were transferred to 24-well plates with phenol red-free RPMI 1640 media supplemented with 10% FCS and MDV3100. Cells from control dishes 1-3 were maintained until resistant clones were cryopreserved to maintain a constant culture time for control and experimental lines.

Generation of Stable Transduced Lines

Codon-optimized cDNAs encoding WT or mutant ARs were synthesized (DNA2.0) and subcloned into the pLKO-TREX-HA-Neo (Invitrogen). Lentiviruses were produced by transfecting 293FT cells with VSVG:deltaR8.9:cDNA constructs at a ratio of 1:2.5:1.25. Virus was harvested 2-3 d after transfection, filtered, and used to infect LNCaP, MyC-CaP and VCaP cell cultures in the presence of 8 µg ml-1 polybrene. Infected cells were maintained in neomycin for 3 weeks. In all cases, at least 1000 independent clones were pooled to generate stable cell lines to avoid clonal variations. Stable cell lines infected with control vectors were generated in parallel for use as experimental controls.

Microarray $3×10^5$ cells were seeded in 6-well plates 2-3 d prior to treatment with DMSO or 10 µM MDV3100 for 24 h. Total RNA was isolated from cells using the Qiagen RNeasy Kit. RNA integrity and purity were assessed with the RNA 6000 Nano LabChip system on a Bioanalyzer 2100 (Agilent Technologies). Generation of labeled cDNA and hybridization to Affymetrix GeneChip Human Genome U133 Plus 2.0 Array (Affymetrix Inc.) was performed using standard protocols as previously described (8).

Expression Analysis

Probesets from the Affymetrix gene expression datasets were normalized using MASS with a trimmed-mean target of 150, and log 2-transformed. Probesets were then filtered for inclusion only if their maximum value over different samples was at least 5. Ordinary least squares was performed using 0-1 indicator variables as the covariates; one indicator was used to represent the baseline (untreated sample) of each clone, and three indicator variables represented treatment with MDV3100 for each of the classes of samples (control, weakly resistant, and strongly resistant clones). This regression was used to generate nominal p-values and regression coeffecients (i.e. fold-changes).

Individual probesets were considered significantly differentially expressed if their fold-change was >=1.5, with a nominal p-value<=0.05.

Gene Set Enrichment Analysis

Correlation between an AR gene signature (30) was compared to the top-ranked genes upon treatment with MDV-3100. Blue line represents expressed probeset position and is ranked by average fold-change; only those probesets expressed at a MASS-150 level of at least 32 in at least 1 sample are included. The red lines indicate where the probesets mapping to genes in the AR gene signatures appear in our dataset; gray lines for probesets that do not pass nominal significance, and the taller red line represents probesets with a fold-change of at least 1.5 and a nominal p-value less than 0.05. The black curve shows the cumulative sum of the probesets in the AR gene signature, and the dotted line represents the hypothetical cumulative sum for a random list of genes which are unenriched.

Pathway Enrichment Scores

For the candidate signature (30), a two-tailed fisher's exact test was used to determine if probesets representing genes in those signatures were under- or over-represented in the set of probesets that were up- or down-regulated at least 1.5-fold compared to expressed but non-differentially-expressed probesets, with a nominal p-value of 0.05 or less. For an unbiased approach, pathways derived from GO terms and transcription-factor networks were analyzed for over-representation via a one-tailed interpolated fisher's exact test, using genes that varied 1.5-fold or more with a nominal p-value of 0.05 or less compared to all genes represented on the array; Benjamini-Hochberg (BH) correction was then applied to these p-values (8).

Sanger Sequencing

Genomic DNA was isolated from various 1 µM MDV resistant clones and appropriate control lines using the Blood and Tissue DNAeasy kit (Qiagen, cat#69581) according to the manufacturer's directions. Primers were used to amplify exon 8 (the site of the F877L mutation) (Forward: 5'-ATTGCGAGAGAGCTGCATCA-3' (SEQ ID NO: 55); Reverse: 5'-TTCTCGTCACTATTGGCCTC-3' (SEQ ID NO: 56)) and the amplified cDNA was sequenced by Genewiz using the same primers. Trace files were analyzed to confirm the presence of the F877L mutation.

Quantitative Real-Time PCR

For spontaneous clones: 200 k cells were seeded in 6 well plates in RPMI 1640 supplemented with 10% FCS for 2 d prior to treatment with various compounds for 24 h. Alternatively, for experiments involving androgen-depletion, 200 k cells were seeded and grown in 6 well plates in phenol-free RPMI 1640 supplemented with 10% FCS for 2 d. Media was aspirated and replaced with phenol red-free RPMI 1640 supplemented with 10% CSS for 3-4 d prior to treatment with various compounds for 24 h. Similar protocols were applied for genetically engineered lines except that cells were pretreated with Dox for at least 2 d prior to treatment with various compounds to allow sufficient transgene expression. Total RNA was extracted using the RNeasy plus mini kit (Qiagen, cat#74136) according to the manufacturer's instructions. 1-2 µg of total RNA was used for cDNA synthesis using a high capacity cDNA reverse transcription kit (Applied Biosystems, cat#4368813). cDNA from each sample was diluted 15-20 fold and real-time was performed in triplicates using gene-specific primers and FastStart Universal Probe Master Mix (Rox) (Roche Applied Science) on an ABI 7900HT series PCR machine. Expression levels were normalized to TBP expression. All analysis was performed using the SDS2.3 software. The following gene-specific primers (Invitrogen) were used: AR (Hs00171172_m1), KLK3 (Hs02576345_m1), NKX3-1 (Hs00171834_m1), TMPRSS2 (Hs01120965_m1), SLC45A3 (Hs00263832_m1), TBP (Hs00427620_m1), DHFR (Hs00758822_s1) and TK1 (Hs01062125_m1).

In Vivo Tumorigenesis Assays 10 million LNCaP cells (C1, clone #1) mixed 1:1 with matrigel were injected subcutaneously into the flank of castrated 7-8 week male nu/nu mice. Tumor-bearing mice (tumor volume=150-300 mm$^3$) were treated with vehicle or 30 mg/kg MDV3100 daily. Tumors were measured using calipers and tumor volumes were calculated using length× width/2. Data is expressed as mean±SEM. All animal experiments were performed in compliance with the guidelines of Novartis Biomedical Research Animal Care and Use Committee protocols and regulations.

Statistical Analysis

Results were reported as mean±SEM (standard error of the mean). Two-sided independent student's t-test without equal variance assumption was performed to analyze gene expression levels and end-points of in vitro luciferase assays. For gene-set enrichment analysis, p-values shown are based on a two-tailed Fisher's exact test comparing probesets in the gene signature that pass significance to those that do not, versus the significance/insignificance of all other probesets. For animal experiments, a two-tailed Fishers exact test was performed to determine the significance in percentage of mice growing palpable tumors in each group.

Accession Number

Gene expression microarray data used to analyze differential gene expression upon treatment with MDV3100 vs. DMSO in spontaneous and engineered lines has been deposited at the NCBI Gene Expression Omnibus with the accession GSE44924 and GSE44927 respectively.

Additional experimental procedures are listed in the SUPPLEMENTARY METHODS.

Supplementary Methods

RNA-Seq Analysis

RNA-seq alignment consisted of fastq pre-processing, generation of joint genome/transcriptome fasta files to align against, and alignment with bowtie2 and a modified version of tophat1.3; see below for details.

FASTQ Pre-Processing:

Paired reads were preprocessed to trim low-quality bases on the 3' end as well as adapter sequences. First, low-quality bases were removed from the 3' end using the BWA algorithm (i.e. the read is trimmed to maximize the sum of the phred-scaled quality scores minus 20*resulting readlength). Read pairs where either read was less than 50 bp in length after quality trimming were removed. Next, read pairs were checked for complementarity. Complementarity that resulted in 3' overhang matching one of the Illumina adapter sequences had the overhang trimmed. If the complementarity indicated a fragment insert size of less than 67 bp, that read pair was removed.

Generation of Joint Genome/Transcriptome Files:

In order to competitively align reads against both the genome (coming from DNA contamination, random transcription, or pre-mRNA) and transcriptome, numerous merged FASTA files were created. Additionally, sequences representing phiX, rRNA, the 1000-genomes-derived "decoy" sequences, and viral (TaxID 10239) nucleic acid sequences from RefSeq (1) were included in the merged FASTA files. The genome used was NCBI GRCh37.5; however, all single nucleotide polymorphisms in the reference were swapped to the alternate allele if this allele was more common in at least 75% of the annotated populations according to dbSNP137. The transcriptome sequences were created using UCSC knownGene. Three transcriptome FASTA files to append to the above sequences were created:

(1) Since the longest readlength used was 101 nucleotides, 100 base pairs flanking each annotated junction was included, where the flank followed other junctions for exons less than 100 bp in length. This version was used in the first step of Tophat, which performs single-end alignments.

(2) Typically, the 99th percentile of fragment sizes was less than 500 base pairs in length. A version was thus also created that followed 500 base pairs flanking each annotated junction, where the flank followed other annotated junctions for the transcript in question. Overlapping junctions were merged to minimize the target FASTA alignment file; for example, a gene with only one isoform where every exon was <500 bp long would have only a single FASTA record containing the sequence of the entire cDNA. A gene with 2 isoforms, one including an alternatively spliced exon, would contain 2 FASTA records; one with the entire cDNA containing the alternatively spliced exon, and one 1000 nucleotides long containing the 500 bp flanking the junction that spliced out said exon. This version was used for paired-end alignment using Bowtie 2.

(3) For those samples with longer fragment sizes, the same as (2) but with 1000 bp flanks instead of 500 bp flanks.

The sequences names for each junction indicated the position(s) of the included nucleotides on the reference genome, to allow easy mapping back to genomic coordinates. Each of these 3 versions was concatenated to the reference genome+other sequences listed above, and indexed using Bowtie 2.0.0-beta7 as well as bowtie 0.12.8.

Alignment of FASTQ files: FASTQ files were first aligned using bowtie2.0.0-beta7 (2), using the following parameters:

bowtie2 -D 18 -R 0 -L 28 -N 1 -i L,0,.32 --mp 40,30
    --score-min C,-132,0 --gbar 3 --rdg 80,2 --rfg 80,5 -k 10
    -x GRCh37c_knownGene_pe500 juncs
    -1 read1.fastq.trimmed.txt -1 read2.fastq.trimmed.txt
    --no-mixed -X 1000 -p 4 -reorder as well as rg-id and various rg parameters to identify the sample, where the file GRCh37c_knownGene_pe500.juncs refers to (2) in the genome/transcriptome joint file above.

Reads that did not map, mapped 10 independent times (the maximum allowed), or had a mismatch in the first or last 2 bp, were considered unaligned and redirected to a FASTQ file to remap using Tophat. All other reads had their BAM files edited to use genomic coordinates and had redundant mapping caused by the merged genome/transcriptome file removed.

Reads not aligned by the initial Bowtie2 alignment were aligned with a modified version of Tophat version 1.3 (3). The modifications primarily allow for the indicated hybrid genome/transcriptome fasta file ((1) from above) as input and conversion of the transcriptome-mapped reads back to their genomic location inside tophat. The decision tree process to choose the best paired alignment from possible single alignments was also modified in an iterative process, optimizing on reducing the number of base-pair mismatches. Minor modifications included modification to the segmentation of full-length reads and amount of flanking sequence used for mapping segments. Tophat was called using the following example arguments, along with the appropriate read group parameters:

tophat --num-threads=4 -r -34 --mate-std-dev 126 --bwt-idx-prefix=GRCh37c
    --with-transcriptome-
        prefix=GRCh37c_knownGene_se.juncs
    -G knownGene.refFlat.gtf --library-type fr-unstranded --segment-length=25 --max-insertion-length 10 --max-deletion-length 10
-F 0.05 -a 12 --microexon-search --no-coverage-search --bowtie-e 45
--segment-mismatches 2 --max-multihits 25
bowtie2_unaligned. 1.fq.gz bowtie2_unaligned.2.fq.gz where the insert-size parameters (-r and --mate-std-dev) are estimated empirically from the initial bowtie2 mapping to the joint genome/transcriptome. The initial single-end bowtie mapping within the modified tophat is called as follows:
bowtie -q -e 45 --nomaqround --sam --sam-nohead -p 4 -k 25 -m 25
GRCh37c_knownGene_se. juncs - <zcat left_kept_reads. fq.gz The bam output from tophat (accepted_hits.bam) was then merged with the output from the original bowtie2 alignment to create a single alignment file. Only read pairs that had a unique best alignment to the human genome/transcriptome were then kept in the final output alignment file (i.e. multi-mapped reads, rRNA reads, and viral reads were excluded from subsequent analyses).

RNA-Seq Resistance-Associated Mutation Discovery

Aligned bam files were marked for duplicate reads using the MarkDuplicates tool available from Picard. Next, GATK v1.5 (4) was used to for base quality recalibration, using dbSNP137 as known sites and standard covariates and options. Variants were called using the UnifiedGenotyper from GATK v1.5, and annotated for standard quality metrics, presence in dbSNP137, the NHLBI exome sequencing project (ESP6500, Exome Variant Server, NHLBI GO Exome Sequencing Project (ESP), Seattle, Wash. and COSMIC v58 (5), as well as function using SnpEFF (6) and the ensemble transcript database GRCh37.68 available from SnpEFF.

Mutations that were consistent across all samples were then filtered out. The posterior likelihood scores output from the UnifiedGenotyper were summed over all samples, for each genotype (homozygous reference, heterozygous, and homozygous alternate) for each variant; the minimum of the three summed scores represents a phred-scaled discordance measure per variant; those variants with a discordance less than 100 were excluded from further analysis, as were variants that occurred at runs of homozygosity, showed evidence (>10%) of the alternate allele in samples called homozygous reference, or had on average less than 20% of the reads from the alternate allele in samples called heterozygous or homozygous alternate. Variants were also removed if they did not result in a predicted change to protein coding sequence.

Immunoblot Analysis

Whole Cell Lysates:

Cells were lysed in TPER buffer (Thermo Scientific, cat#78510) containing Halt protease and phosphatase inhibitor mixture (Thermo Scientific, cat#78440) and subsequently boiled for 5 min. Approximately 20 µg of protein was loaded per lane and resolved by SDS polyacrylamide electrophoresis. Protein was transferred onto nitrocellulose membranes, blocked in 5% low-fat milk and probing was carried out with antibodies to AR N-20 (1:1000 dilution, Santa Cruz, cat# Sc-816,), histone H3 (1:2000 dilution, Cell signaling, cat#9715s), β-tubulin (1:1000 dilution, Abcam, cat# ab6046), HA-HRP (1:500, Roche, cat#12 013 819 001), β-actin (1:3000 dilution, Sigma, cat# A-2228) and p-AKT (1:1000 dilution, Cell Signaling, cat#4060). Membranes were incubated with horseradish peroxidase (HRP)-conjugated anti-mouse secondary antibody (1:4000 dilution, Millipore cat#12-348) or anti-rabbit secondary antibody (1:4000 dilution, Pierce, cat#31430) for 1 h and signals were developed using the ECL method (GE Healthcare).

Nuclear and Cytoplasmic Protein Fractionation:

For spontaneous resistant clones, 1 million C1 and clone #1 cells were seeded in RPMI 1640 media supplemented with 10% FCS in T75 flasks and allowed to grow for 2 d prior to treatment with DMSO, 0.1 nM R1881 or 10 µM MDV3100 for 24 h. For genetically engineered lines, 1 million LNCaP-derived lines were seeded in RPM1 1640 media supplemented with 10% FCS and 100 ng ml-1 Dox (Sigma, 44577-1G) in T75 flasks and left for 2 d prior to treatment with DMSO, 0.1 nM R1881 or 10 µM MDV3100 for 24 h. Alternatively, media was aspirated and replaced with phenol-red free RPMI 1640 media containing 10% CSS and 100 ng ml-1 Dox. Following four days of growth in 10% CSS, DMSO or 10 µM MDV3100 was added to the flasks and left overnight. The next day, cells were harvested with trypsin, centrifuged at 500×g for 5 min, washed with PBS, transferred to 1.5 ml microcentrifuge tubes and pelleted by centrifugation at 500×g for 2-3 min. Cytoplasmic and nuclear protein extraction was performed according to manufacturer's instructions (Thermo Scientific, cat#78833). Briefly, the pellet was resuspended in 500 µl of ice-cold Cer I buffer and incubated on ice for 10 min. Following incubation, 27.5 µl of ice-cold Cer II buffer was added, vortexed and incubated for 1 min on ice. The lysate/Cer I/II mixture was vortexed again, centrifuged at 14000×g for 5 min and the cytoplasmic extract (supernatant) was transferred to pre-chilled tubes. The insoluble pellet, which contains nuclei, was resuspended in ice-cold 250 µl NER buffer, vortexed and placed on ice. Sample was vortexed for 15 s every 10 min for a total of 40 min. Following incubation, samples were centrifuged at 14000×g for 10 min. Supernatant, which contains the nuclear extract, was transferred to pre-chilled tubes. These samples were processed for immunoblot analysis as described above.

QuikChange Mutagenesis

The AR coding region amplified by PCR was inserted into pcDNA3.1 vector. The single mutants T878A, W742C, W742L, F877L and double mutant F877L/T878A expression plasmids were created with the following primer sets (5'-GAGAGCTGCATCAGTTCGCTTTTGACCT-GCTAATC-3' (SEQ ID NO: 58) and 5'-GATTAGCAGGT-CAAAAGCGAACTGATGCAGCTCTC-3' (SEQ ID NO: 59), 5'-CATTCAGTACTCCTGCATGGGGCTCATGGTG-3' (SEQ ID NO: 60) and 5'-CACCATGAGCCCCATGCA-GGAGTACTGAATG-3'(SEQ ID NO: 61), 5'-GTCATTCA-GTACTCCCTGATGGGGCTCATGG-3' (SEQ ID NO: 62) and 5'-CCATGAGCCCCATCAGGGAGTACTGAATGAC-3' (SEQ ID NO: 63), 5'-GAGAGCTGCATCAGCT-CACTTTTGACCTG-3' (SEQ ID NO: 64) and 5'-CAGGT-CAAAAGTGAGCTGATGCAGCTCTC-3' (SEQ ID NO: 65), 5'-GAGAGCTGCATCAGCTCGCTTTTGACCTG-3' (SEQ ID NO: 66) and 5'-CAGGTCAAAAGCGAGCTGAT-GCAGCTCTC-3' (SEQ ID NO: 67)) by site-directed mutagenesis using the QuikChange XL site-directed mutagenesis kit (Agilent, cat#200517-5).

Luciferase Reporter Assays

Reporter assays were performed as follows: 3×10⁵ HEK293T cells were seeded in 6-well plates in DMEM supplemented with 10% FCS and 1×NEAA 24 h prior to transfection. Alternatively, 1×10⁶ VCaP cells or 3×10⁵ PC3 cells were seeded in 6-well plates in appropriate media supplemented with 10% CSS 24 h prior to transfection. The following day, 400 ng of the AR firefly reporter plasmid (4×ARE-luciferase), 100 ng of the control plasmid (constitutive renilla-luciferase expressing plasmid) and 200 ng of AR overexpressing pcDNA plasmids described above were co-transfected using Lipofectamine 2000 (Invitrogen, cat#11668027). Media was replaced 6 h post-transfection with fresh media containing DMSO, 0.1 nM R1881, 10 µM MDV3100, 10 µM bicalutamide, 10 µM MDV3100+0.1 nM R1881, and 10 µM bicalutamide+0.1 nM R1881. Cells were collected ~16 h following treatment and assayed for luciferase activity using the Glomax 96 microplate luminometer (Promega). Firefly activity was normalized to Renilla using the Dual Luciferase Assay reagent (Promega, E1910). All experiments were performed at least three times.

Cell Growth Assays

LNCaP Cells

Short-Term Microtiter Plate Assays:

1000 cells (spontaneous resistant or engineered lines) were seeded in media supplemented with 10% FCS. For spontaneous resistant clones, increasing concentrations of compounds were added on the day of seeding whereas for engineered lines, compounds were added after 2 d of doxycycline treatment. In all cases growth assays were performed using CellTiter-Glo Luminescent Cell Viability Assay Reagent (Promega, cat# G7573) 7 d following compound treatment.

Long-Term Colony Formation Assays:

5000-7500 cells (spontaneous resistant or engineered lines) were seeded in 6-well plates in media supplemented with 10% FCS. For spontaneously resistant clones, MDV3100 was added to the plates on the day of seeding and media/compound was replaced every week. For engineered lines, doxycycline was added on the day of seeding and various concentrations of compounds (MDV3100/bicalutamide) were added after 2 d. Similar to the spontaneous resistant lines, media/dox/compound was replaced once every week. Viable colonies were stained after 3-4 week cultures. Following media aspiration, 0.5% crystal violet was added to the wells and left overnight. The next morning, crystal violet solution was removed and wells were carefully washed with ddH$_2$O to remove residual staining solution. The plates were air-dried overnight prior to imaging.

VCaP Cells

VCaP cells, expressing either AR-T878A or -F877L/T878A were seeded at 500,000 cells/well in 6-well plates in DMEM supplemented with 10% FCS. Doxycycline was used to induce expression of the AR plasmids for 2 d prior to addition of DMSO or 10 µM MDV3100. Growth assays were performed using CellTiter-Glo Luminescent Cell Viability Assay Reagent (Promega, cat# G7573) 8 d following compound treatment. Data was compared to day 0 (the day compound was administered).

Myc-CaP Cells

Myc-CaP cells, carrying either AR-T878A or -F877L/T878A, were seeded at 100 cells/well in 6-well plates in DMEM supplemented with 10% FCS. 0.2 µg/ml doxycycline was added to media to induce the expression of AR. Media was changed every 3 days until colonies formed (~2 weeks). 0.1% crystal violet was used to stain colonies.

22RV1 Cells

22Rv1 cells were seeded at 5000 cells/well in 6-well plates in DMEM supplemented with 10% FCS. Cells were treated with various compounds for 14 days prior to staining with 0.1% crystal violet.

Generation of Spontaneous MDV3100 Resistant LNCaP Xenografts

10×10$^6$ LNCaP cells were implanted subcutaneously into the flanks of male castrated mice. Once tumors reached 200-300 mm$^3$, treatment with vehicle or 30 mg/kg MDV3100 was initiated. After 3-4 months of daily treatment, several tumors gained the ability to grow in the presence of MDV3100 spontaneously. When these tumors reached 1000-1500 mm$^3$, mice were sacrificed, and tumors were collected. Tumor fragments from two MDV3100-resistant tumors (one fragment from mouse 1 and three fragments from mouse 2) were subsequently re-implanted into secondary recipients, and treatment with MDV3100 was once again initiated (R1-R4). In addition, a single tumor fragment from both mouse 1 and 2 was implanted into secondary recipients to be treated with vehicle (C1-C2). RNA was collected from all tumors once they reached 1000-1500 mm$^3$ and whole-transcriptome sequencing was performed as previously described.

Example 2. Development and Characterization of a Model of Spontaneous Resistance to MDV3100

Figure 1B:
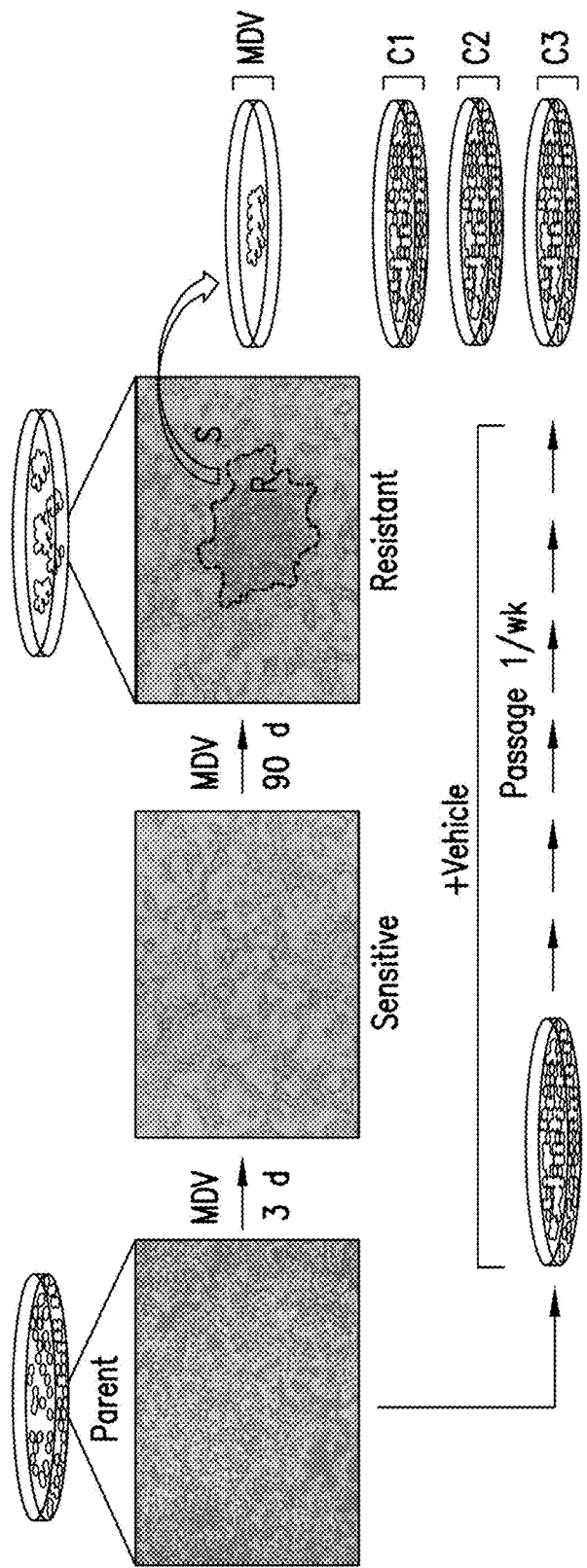
Figure 1C:
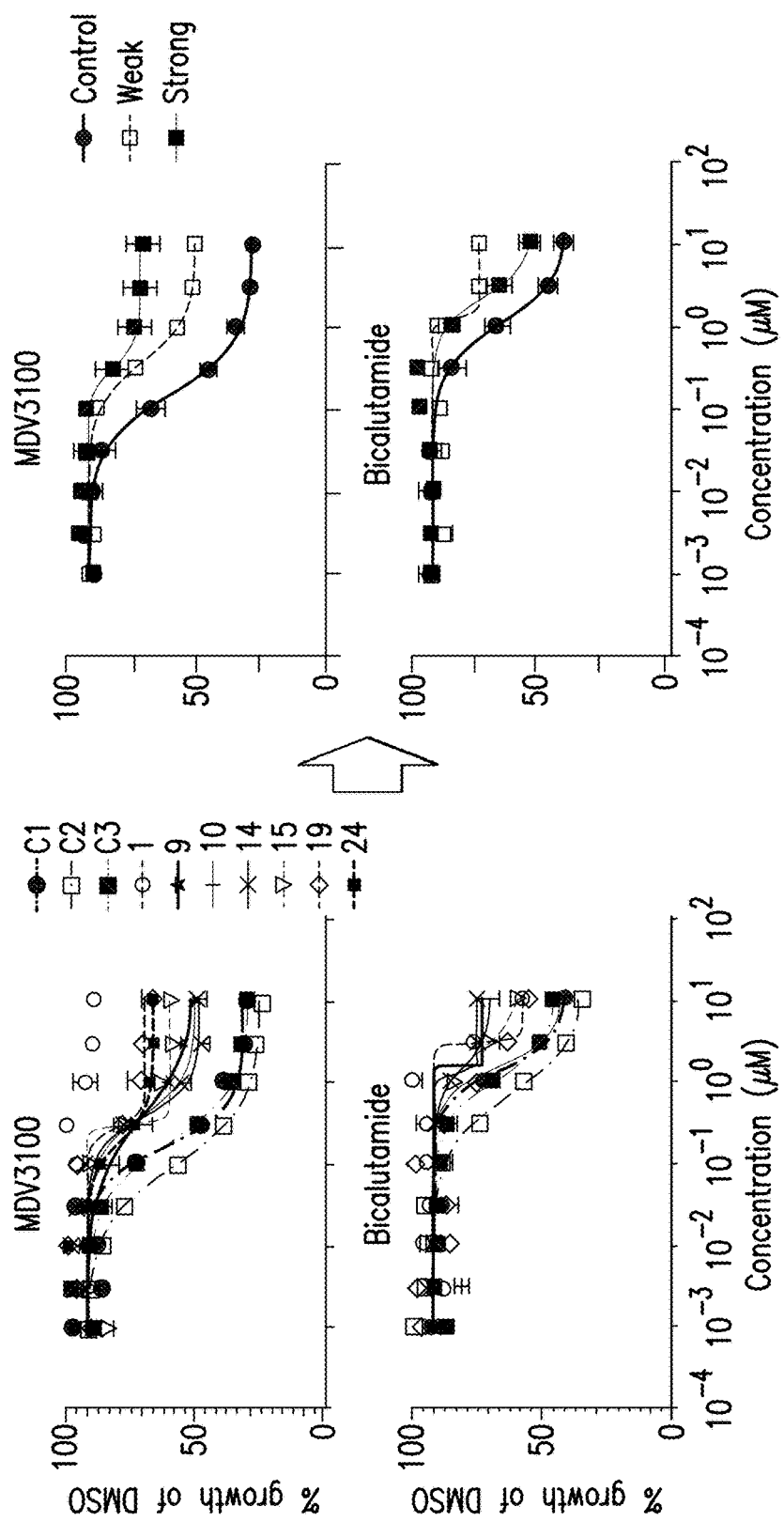

To elucidate endogenous mechanism(s) of resistance to MDV3100, this disclosure describes a model of spontaneous resistance in LNCaP cells (FIG. 1b). Although short-term culture with MDV3100 (<1.5 months) induces population-wide stasis (FIG. 1a, FCS+MDV relative to FCS), long-term culture with 1 µM MDV3100 allows some cells to escape resulting in the emergence of resistant clones (FIG. 1b). Resistant clones that displayed similar growth properties as the control populations (C1-C3, FIG. 1b) are chosen for further characterization. Short-term CTG-based (FIG. 1c) and long-term colony formation assays confirmed the partial resistance phenotype. Further characterization revealed that four of seven resistant clones (clones #1, 15, 19, 24-strongly resistant, green curves and font) displayed significantly higher resistance to MDV3100—the aggregate IC$_{50}$ being >10 µM compared to <10 µM for the remaining three clones (clones #9, 10 and 14-weakly resistant, red curves and font) and 0.2 µM for the controls (FIG. 1c). In contrast, weakly resistant clones showed higher resistance to bicalutamide (IC$_{50}$>10 µM vs 5 µM for strongly resistant and 1 µM for controls) (FIG. 1c), and both sets of clones showed similar sensitivity to an unrelated cytostatic agent Lee011 as the control populations (FIG. 6b). These data collectively suggest that the isolated resistant clones preferentially display resistance to anti-androgens—with the mechanism(s) of resistance in strongly resistant clones fine-tuned to specifically promote resistance to MDV3100.

To elucidate mechanism(s) of resistance, expression levels of AR were first analyzed; overexpression of AR has been previously shown to promote resistance to castrate levels of androgens, and anti-androgen bicalutamide. Chen et al. Nature Med. 10: 33-39 (2004); and Kawata et al. Prostate 70: 745-754 (2010). Unexpectedly, this disclosure failed to observe a significant change in AR expression at the RNA (data not shown) and protein level (FIG. 1d). Furthermore, global analysis of AR pathway activity showed little change at baseline (FIG. 1e), with the exception of a few downstream target genes, cumulatively suggesting lack of significant modulation of the AR pathway at baseline.

Example 3. Strongly Resistant Clones are Resilient to AR Pathway Modulation by MDV3100

Figures 1, 2A:
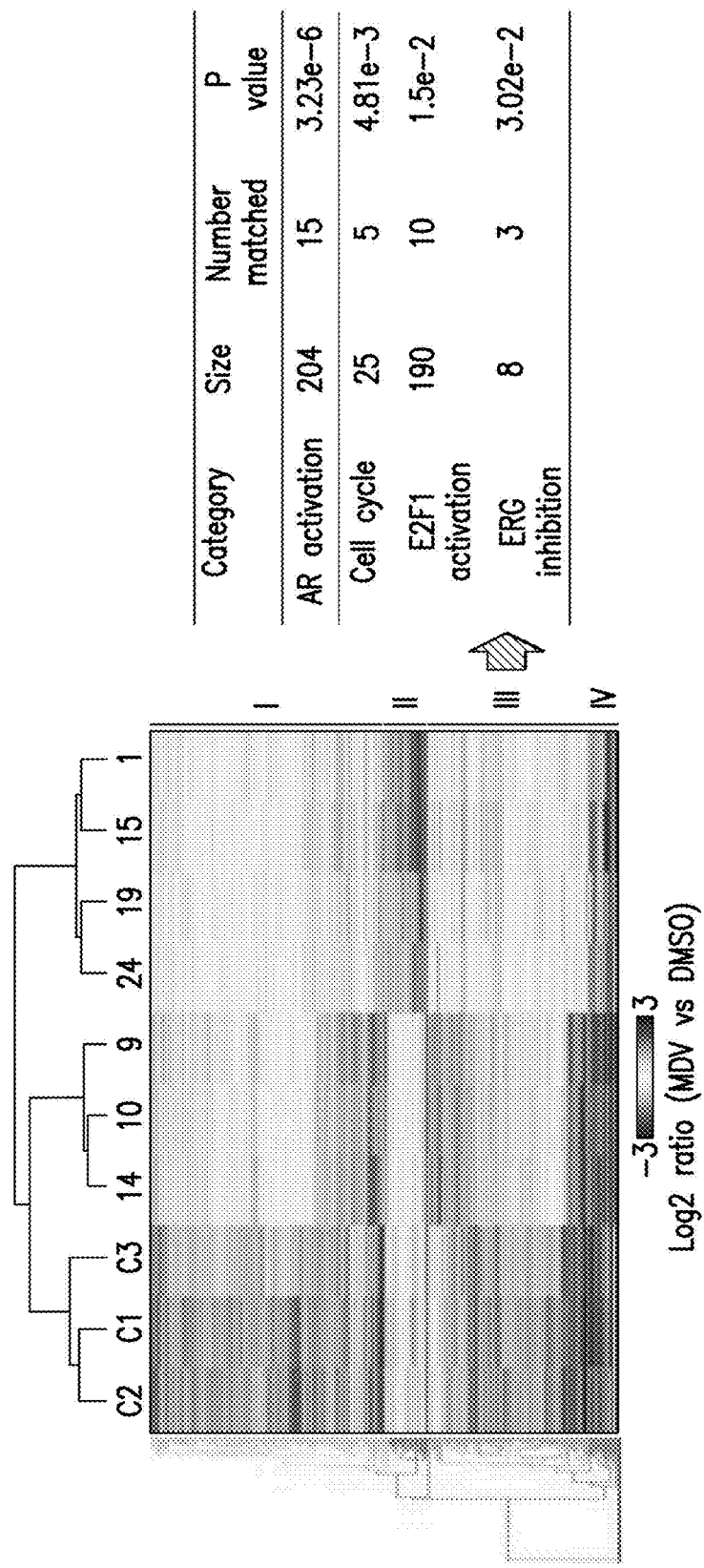
Figures 2, 2A:
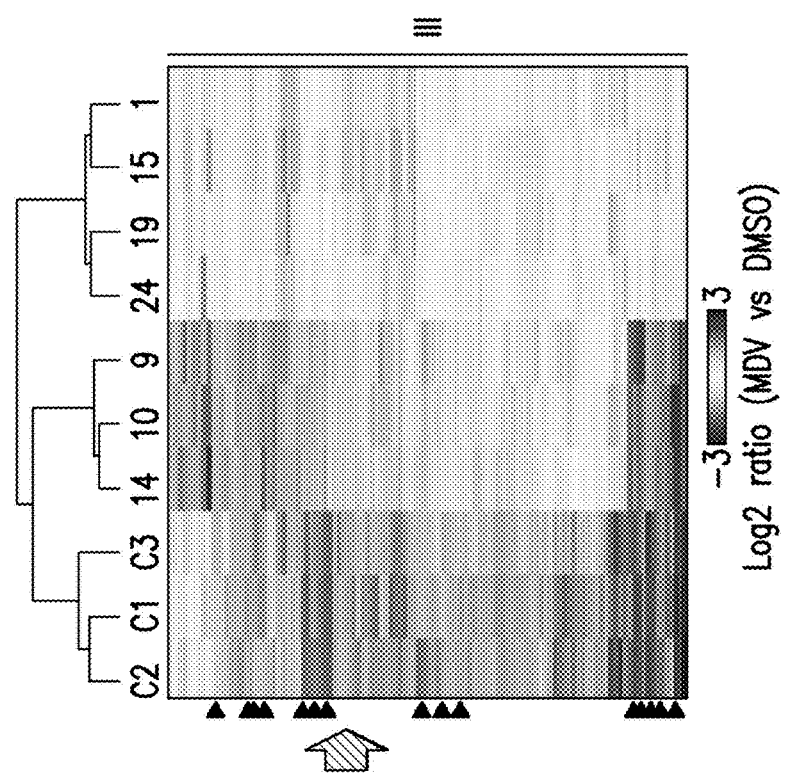
FIG. 2. Resistant clones segregate based on AR pathway sensitivity to MDV3100. A, left, heat map showing differential expression of genes in control (brown font), weakly (red) and strongly (green) resistant lines upon treatment with 10 μM MDV3100 for 24 h. Probesets with an average fold change of at least 2 (MDV vs. DMSO) for at least one sample set (controls, weakly resistant samples, and strongly resistant samples) are shown. Roman numerals listed on right represent broad classes of differentially expressed genes. Middle, table showing results from GO pathway enrichment analysis of genes from class III. Blue shade highlights significant enrichment of genes from the "AR activation" gene set. Right, zoomed image of class III showing relative location of AR regulated genes (blue arrowheads) that add to significance score from pathway analysis. All data presented as log 2 ratio of MDV vs. DMSO treatment. B, correlation between an AR gene signature in comparison to the top-ranked genes upon treatment with 10 μM MDV3100 for 24 h in controls (left), weakly (middle) and strongly (right) resistant lines. Green line represents level of pathway activity—stronger deviation from black diagonal represents greater inhibition of pathway activity by MDV3100 treatment. C, qPCR analysis of expression of canonical AR target genes in ten lines treated with DMSO or MDV3100 for 24 h. Data is presented as percentage of expression in MDV3100-treated sample relative to DMSO (arbitrarily set at 100%). D, DMSO; M, 10 μM MDV3100. TBP was used to normalize expression. Data represent mean±SEM; n=3. *P<0.05 (Student's t-test). D, quantitation of nuclear to cytoplasmic ratio of endogenous AR expression in control (C1, brown) and resistant clone (#1, green) treated with DMSO, 10 μM MDV3100 (MDV) or 0.1 nM R1881 (R1881) for 24 h. Western blot data presented in Supplementary FIG. S3 was analyzed by ImageJ to determine ratios.
Figure 2B:
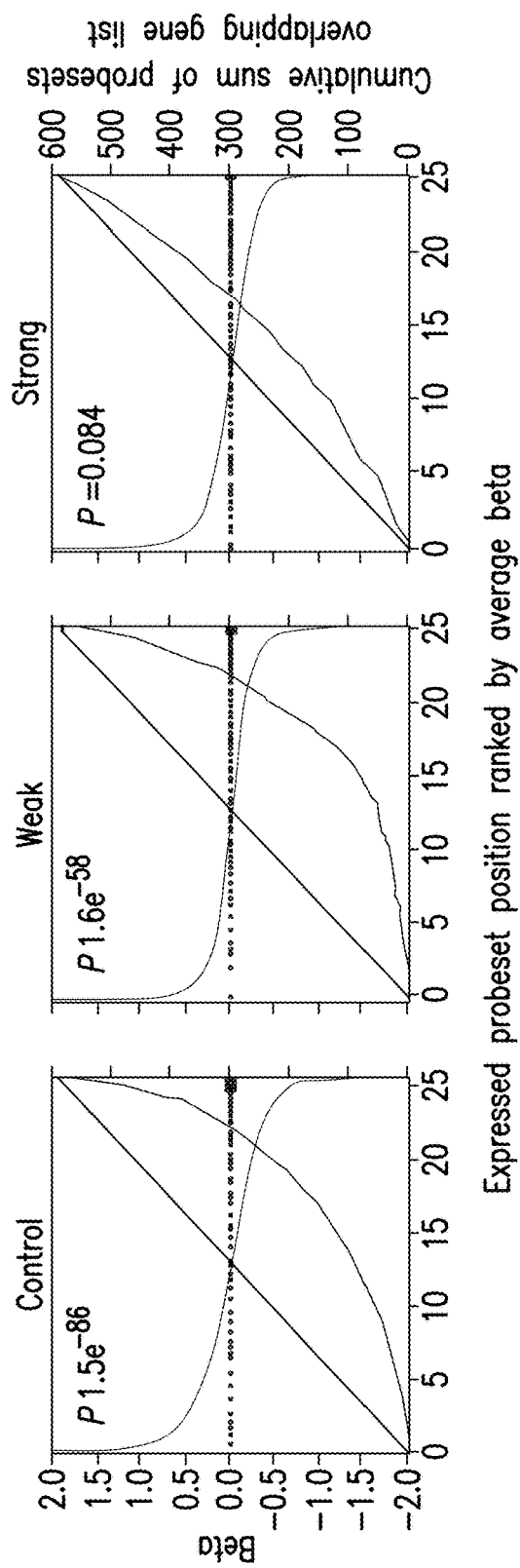
Figure 2C:
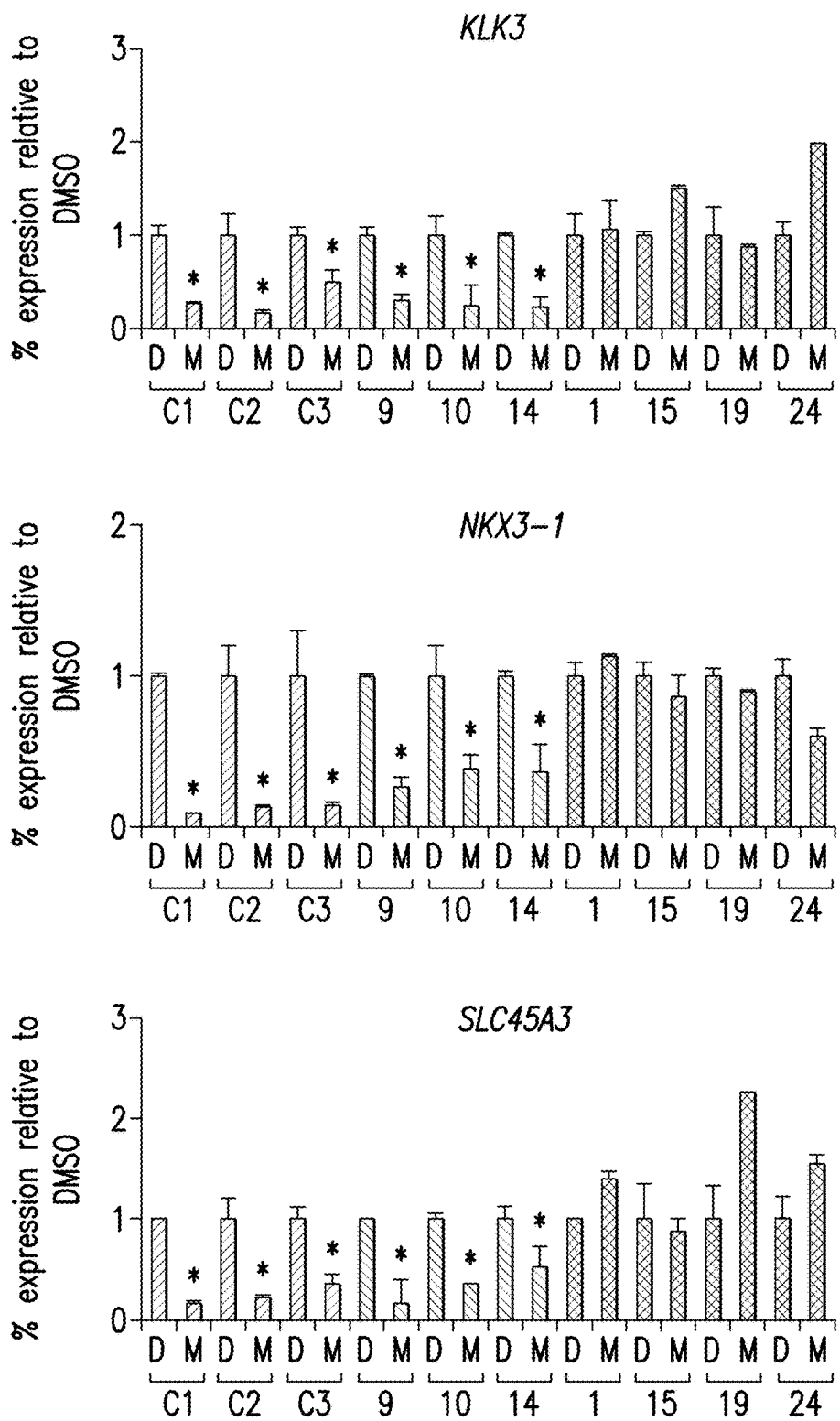
Figure 2D:
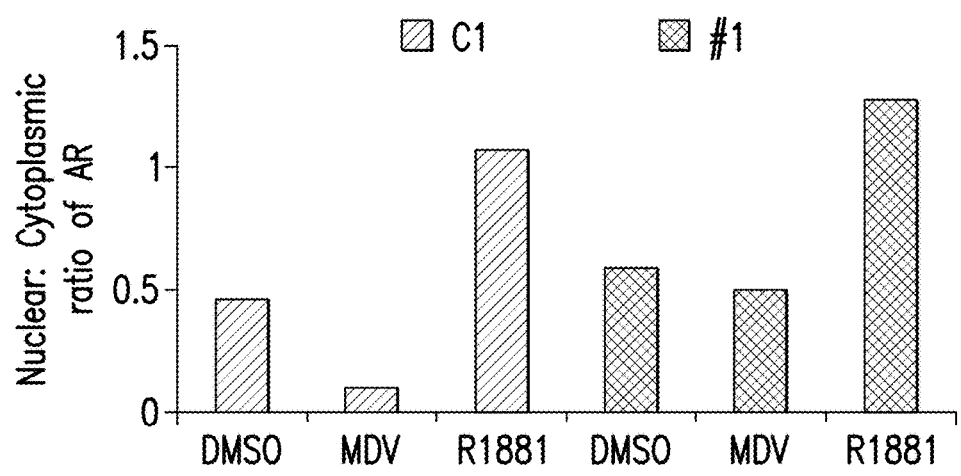
Figure 9A:
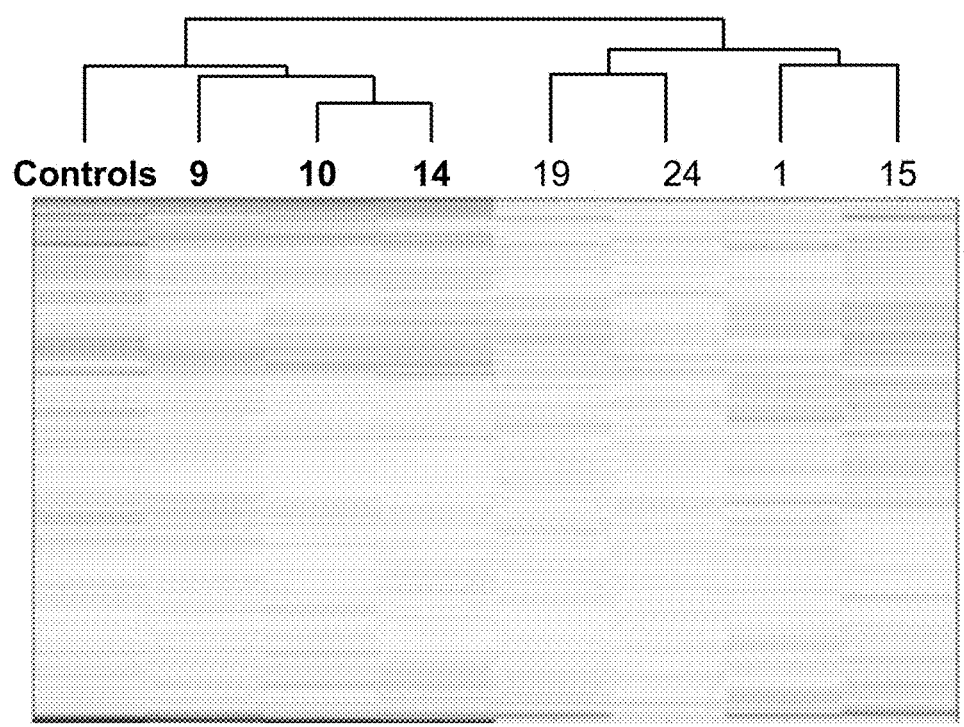
FIG. 9. Strongly resistant clones fail to show modulation of AR pathway activity when treated with MDV3100. A, clustering analysis was performed for controls (aggregate) and resistant lines using an androgen-induced gene signature. All probesets matching genes from the androgen-induced gene signature were used. All expression data is presented as average fold change in MDV3100-treated vs. DMSO-treated samples. B, pathway enrichment analysis showing alterations in AR pathway activity in controls (left), weakly (middle) and strongly resistant (right) lines when treated with 10 μM MDV3100 for 24 h. Correlation between an AR gene signature in comparison to the top-ranked genes upon treatment with 10 μM MDV3100 for 24 h in controls (left), weakly (middle) and strongly (right) resistant lines. Green line represents level of pathway activity—stronger deviation from black diagonal represents greater inhibition of pathway activity by MDV3100 treatment.
Figure 9B:
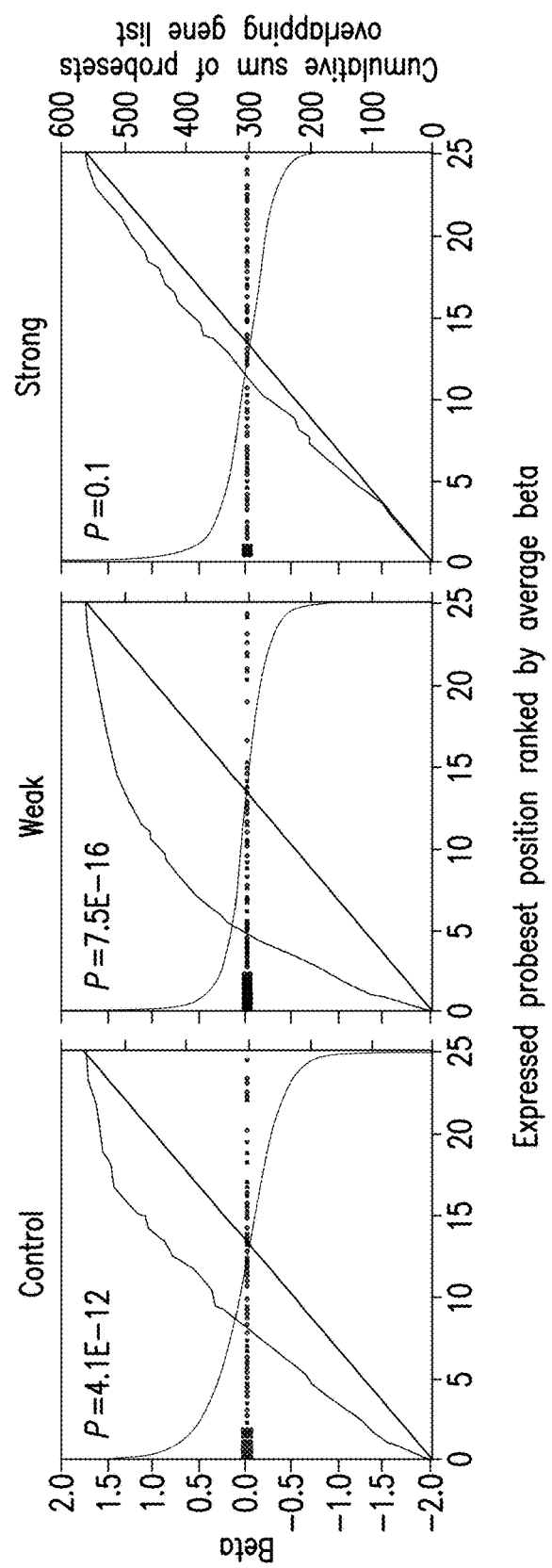
Figure 10:
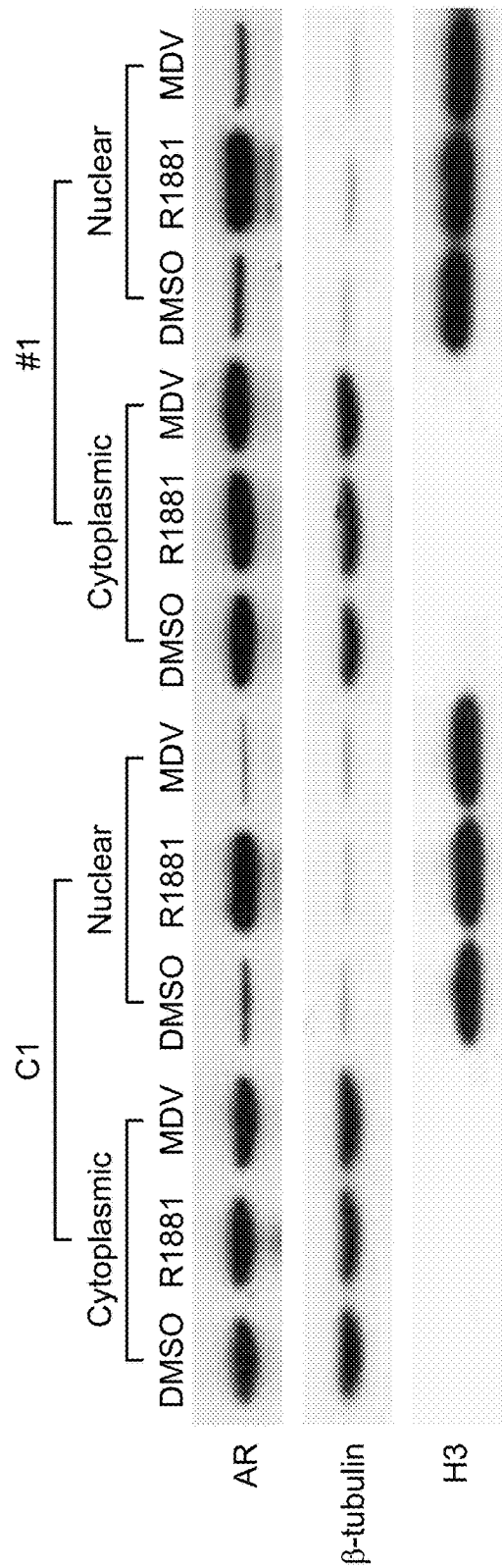
FIG. 10. Western analysis of AR expression in cytoplasmic and nuclear fractions isolated from control (C1) and strongly resistant clone (#1) treated with DMSO, 0.1 nM R1881 or 10 μM MDV3100 (MDV) for 24 h. β-tubulin and histone H3 were probed to validate purity of cytoplasmic and nuclear fractions respectively. Both also served as loading controls.

To further explore the molecular mechanisms that drive resistance, this disclosure performed array analysis on three controls and seven resistant clones treated with DMSO or MDV3100 for 24 h. As expected, this disclosure found many genes (~101) that are uniquely differentially expressed in the three controls when treated with MDV3100—genes overwhelmingly enriched for functions related to cell cycling and DNA damage repair—confirming their sensitivity to the cytostatic influence of MDV3100. This disclosure also uncovered ~191 genes that only showed significant differential expression in the control and weakly resistant clones—of which the down-regulated genes are enriched for cell cycling/DNA damage and unexpectedly, the androgen receptor nuclear signaling pathway ($P=2.01e^{-2}$). This finding provided an initial glimpse into differential regulation of the androgen pathway by MDV3100, with the strongly resistant clones apparently showing resistance to modulation. In support, clustering (FIG. 6a) and GSEA analysis (FIG. 2b and FIG. 9b) both validated reduced AR pathway activity in control and weakly resistant lines upon treatment with MDV3100, with insignificant change being observed in strongly resistant clones. This is validated by qPCR analysis, which also confirmed the blunted effects of MDV3100 on the expression of AR target genes KLK3, NKX3-1 and SLC45A3 specifically in strongly resistant clones (FIG. 2c).

To assess whether differential pathway response to MDV3100 parallels changes in localization of AR in the various clones, this disclosure isolated cytoplasmic and nuclear protein fractions from a control (C1) and strongly resistant (clone #1) line treated with DMSO or MDV3100. Nuclear AR localization is significantly impaired in the control line treated with MDV3100 whereas AR localization is not significantly altered in the strongly resistant clone, providing an explanation for sustained AR pathway activity in strongly resistant lines. In aggregate, analysis of the various clones reveals a clear distinction between two groups—one that is phenotypically more sensitive and shows significant impairment of AR pathway activity upon MDV3100 treatment, and the second that is phenotypically and genetically more resilient to MDV3100.

Figure 11:
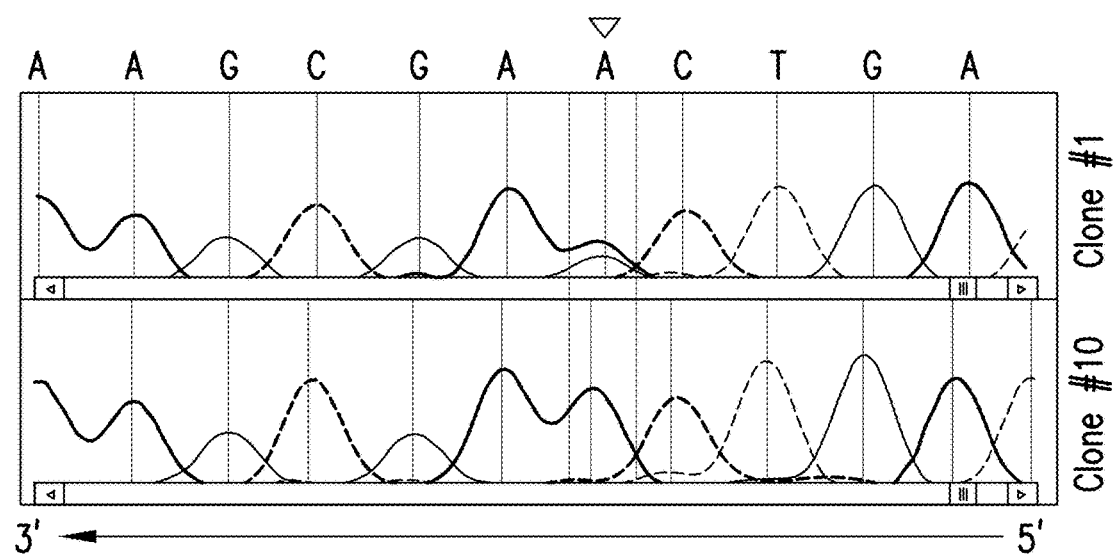
FIG. 11. Sanger sequencing trace plots of genomic DNA isolated from a strongly resistant (clone #1) and weakly resistant (clone #10) clone. Arrow head indicates the presence of two nucleotides in clone #1.
Figure 12A:
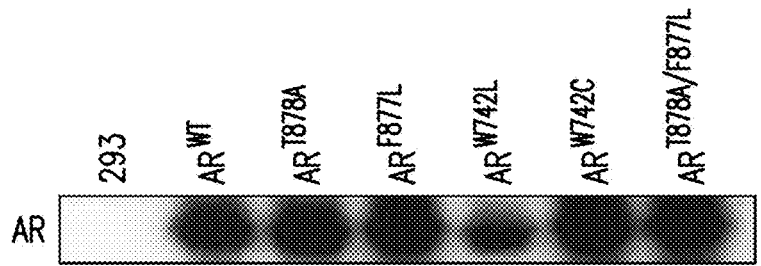
FIG. 12. W742C and W742L mutations in AR confer an antagonist-to-agonist switch specific for bicalutamide. A, western analysis showing expression levels of AR following transient transfection of various AR constructs in HEK293T cells. B, bar graphs showing AR reporter activity following co-transfection with either no AR (left) or with W742L (middle) or W742C (right) mutant ARs. Cells were treated with vehicle (Veh), 0.1 nM R1881, 10 μM MDV3100 (MDV), 10 μM bicalutamide (Bic), 10 μM MDV3100+0.1 nM R1881 (M/R) or 10 μM Bic+0.1 nM R1881 (B/R). All data is normalized to Renilla luciferase ($R_{LUC}$) expression. Data represent mean±SEM; n=3. **P<0.01 (Student's t-test).
Figure 12B:
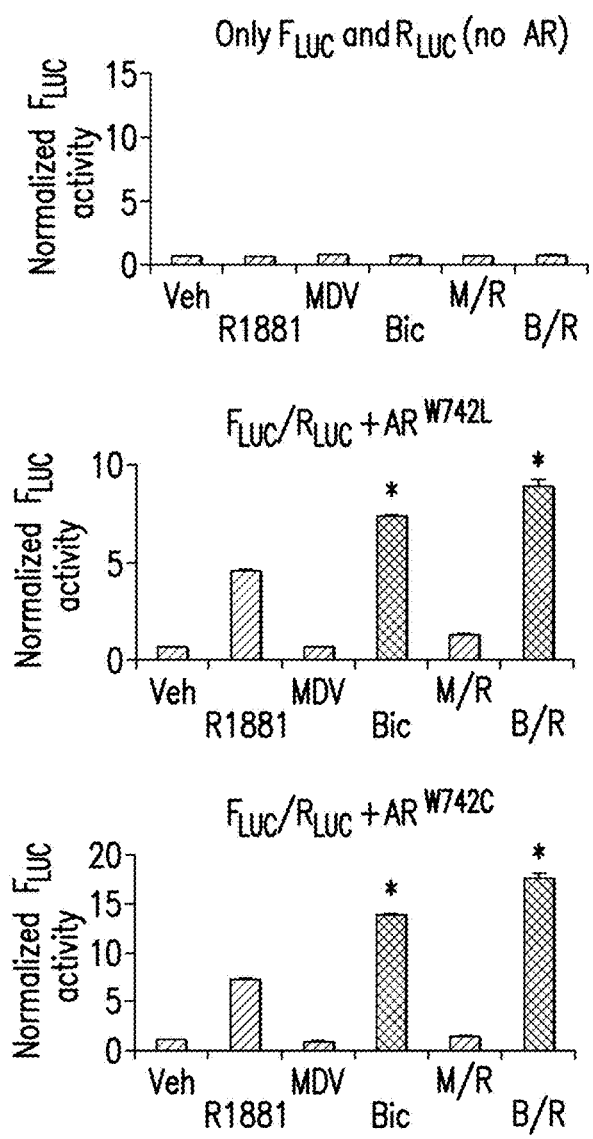
Figure 13:
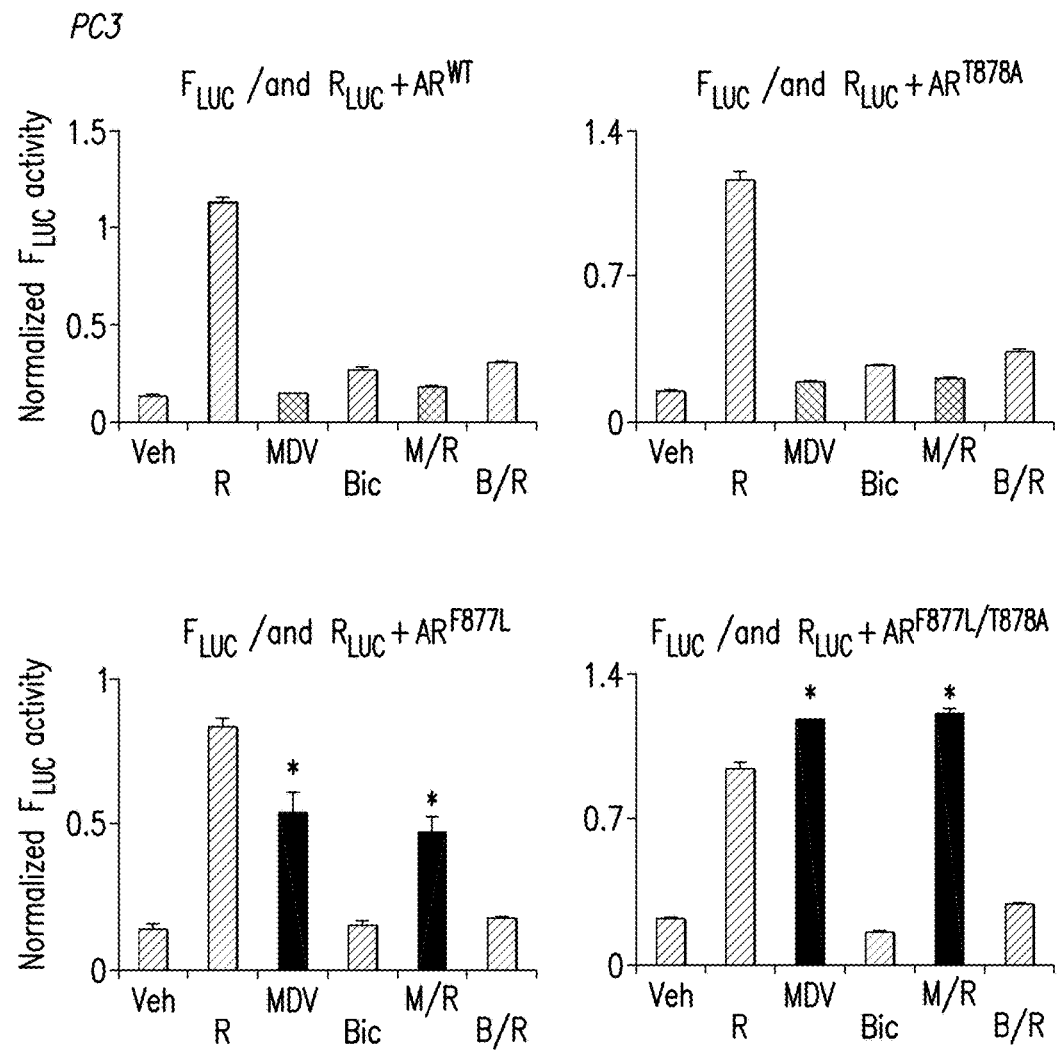
FIG. 13. F877L mutation, alone or in conjunction with T878A, confers an antagonist-to-agonist switch specific for MDV3100 in PC3 cells. Bar graphs showing AR reporter activity following co-transfection with either WT AR (left), T878A ($2^{nd}$), F877L ($3^{rd}$) or with F877L/T878A (right) mutant ARs in PC3. Cells were treated with vehicle (Veh), 0.1 nM R1881, 10 μM MDV3100 (MDV), 10 μM bicalutamide (Bic), 10 μM MDV3100+0.1 nM R1881 (M/R) or 10 μM Bic+0.1 nM R1881 (B/R). All data is normalized to Renilla luciferase ($R_{LUC}$) expression. Data represent mean±SEM; n=3. *P<0.05 (Student's t-test).

Example 4. RNA-Seq Analysis Uncovers a Highly Recurrent Mutation in AR that Correlates with Resistance Although it is clear that AR pathway activity is resilient to modulation by MDV3100 in strongly resistant clones, it is unclear 1) how this pathway remains active in the presence of MDV3100 and 2) whether sustained AR pathway activity is responsible for the resistance phenotype observed in the strongly resistant clones. Since array analysis failed to identify relevant genes/pathways that may rationally explain the sustained AR pathway activity, this disclosure, without wishing to be bound by any particular theory, reasoned that perhaps a mutation(s) in components of the AR pathway may desensitize the strongly resistant clones to MDV3100. To explore this possibility, this disclosure performed RNA-seq analysis on the lines described above and included several lines that became spontaneously resistant to long-term culture in 10 µM MDV3100—these clones like the weakly resistant clones continued to show AR pathway modulation in response to MDV3100. Interestingly, this disclosure discovered several recurrent mutations that are shared by majority of the resistant clones that are undetectable in control populations and vice versa. This data implicates the presence of at least two populations in the parental LNCaPs—a major fraction that is phenotypically highly sensitive to MDV3100 and a minor sub-population that likely diverged many generations ago, accrued many novel mutations and is phenotypically more resistant to MDV3100. Unsupervised clustering analysis based on the mutational profiles of each of the clones resulted in two clusters—one containing the three control lines and the strongly resistant clone #19, and the second clustering all remaining clones. The fact that majority of the clones cluster together makes identification of driver mutation(s) difficult without a priori knowledge—however, our knowledge of blunted AR pathway modulation in strongly resistant clones allowed us to focus our search for mutations unique to these clones. Excitingly, this disclosure identified a single, recurrent mutation shared by all four—a mutation in AR, the direct target of MDV3100. The novel F877L mutation is in the ligand-binding domain of AR, is heterozygous (FIG. 11) and neighbors a preexisting homozygous T878A mutation in LNCaP cells, a mutation that is known to confer resistance to flutamide (Fenton et al. 1997; and Hara et al. 2003). The mutant to wild-type allelic frequency is approximately 40% with the exception of clone #15, which presents the lowest frequency at 20%. The presence of the F877L mutation in genomic DNA is confirmed by Sanger sequencing (FIG. 11).

Example 5. Computational Modeling and Experimental Validation of an Antagonist-to-Agonist Switch To functionally test the hypotheses generated by computational modeling, this disclosure assessed the transcriptional responses to an agonist and anti-androgens bicalutamide and MDV3100 of the wild-type; single mutants T878A, W742C, W742L and F877L; and the double mutant F877L/T878A ARs in transactivation assays. In support of the modeling data, this disclosure finds that only F877L single mutant and F877L/T878A double mutant ARs had a substantial transactivation response to MDV3100—comparable to 0.1 nM R1881—suggesting an antagonist-to-agonist switch that is exquisitely specific for MDV3100. However, these data are in stark contrast to the lack of pathway modulation observed in strongly resistant clones in response to MDV3100 (FIG. 2b-c). These apparently conflicting results may be in part due to the experimental conditions—whereas transactivation experiments assayed the influence of single alleles in an AR non-expressing line, strongly resistant clones harbor the F877L mutation in a heterozygous manner. To test whether an antagonist-to-agonist switch for MDV3100 is also observed in strongly resistant clones, this disclosure assesses transcriptional responses in media stripped of endogenous androgens—minimizing basal AR pathway activity and reducing the response of the endogenous AR to MDV3100. Synonymous with the observations made from reporter-based assays, MDV3100 treatment alone or in combination with agonist significantly enhanced KLK3 expression in strongly resistant clones. These data in aggregate strongly imply that the F877L/T878A mutation allows mutant AR to utilize MDV3100 as an agonist—a switch specific for MDV3100 as sensitivity to bicalutamide is maintained.

Figure 5A:
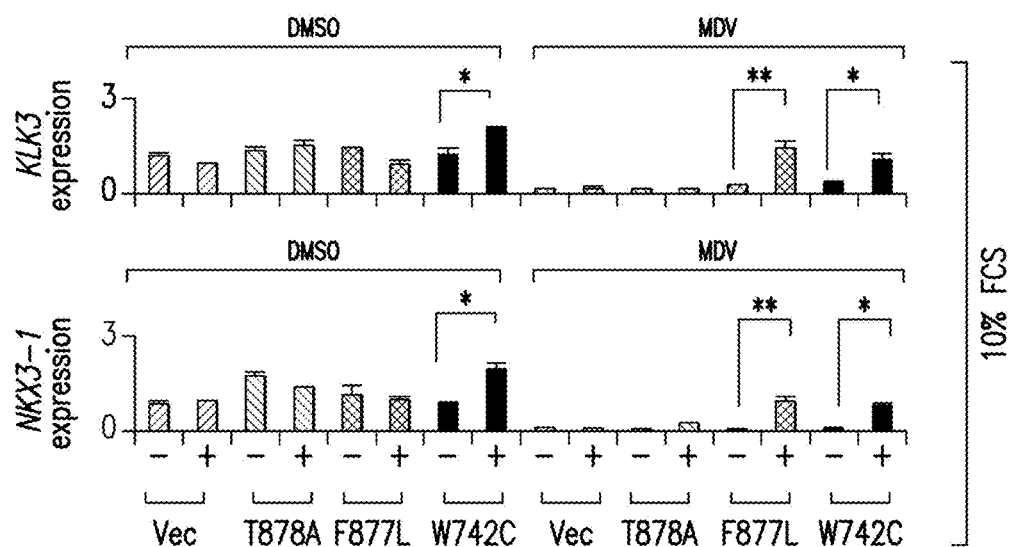
FIG. 5. PCa cells engineered to overexpress AR-F877L/T878A are genetically and phenotypically resistant to MDV3100. A, qPCR analysis of KLK3 (top) and NKX3-1 (bottom) expression in various engineered lines (vector controls (Vec); T878A; F877L/T878A, F877L; W742C/T878A, W742C). All lines were pre-treated with vehicle (−) or doxycycline (+) for 3 d prior to treatment with DMSO (left) or 10 μM MDV3100 (right) for 24 h in 10% FCS. TBP used to normalize expression. Data represent mean±SEM; n=3. *P<0.05, **P<0.01 (Student's t-test). B, western analysis of exogenous AR (HA) expression in cytoplasmic and nuclear fractions isolated from various engineered lines treated with DMSO (D) or 10 μM MDV3100 (M) in media supplemented with 10% CSS. All lines were pretreated with Dox for 3 d prior to treatment with DMSO or MDV3100 for 24 h. F877L, F877L/T878A; W742C, W742C/T878A. β-tubulin (β-tub) and histone H3 (H3) were probed to validate purity of cytoplasmic and nuclear fractions respectively. C, colony formation assays of various engineered lines (Dox −/+) treated with DMSO, 1 μM MDV3100 (MDV) or 1 μM bicalutamide (BIC) for 3-4 weeks. Representative experiment from three independent experiments is shown. D, top, colony formation assays of Myc-CaP cells engineered to express AR-T878A (left) or AR-F877L/T878A (right) (Dox−/+) treated with DMSO (left wells) or 10 μM MDV3100 (right wells, MDV) for ~14d. Bottom, quantitation of colony formation data by ImageJ. E, tumor volume measurements of control (C1, red) and resistant clone #1 (#1, green) tumors treated with vehicle (Veh) or 30 mg/kg MDV3100 (MDV). Solid red and green arrows indicate the day daily administration of MDV3100 was initiated in control (C1) and clone #1 (#1) mice, respectively. Dashed green arrow highlights two consecutive days of treatment with MDV3100 prior to a drug holiday in 15 of 30 mice injected with clone #1 (#1, dark green). n=7-8 tumors for all groups except #1 veh (n=2). Data represent mean±SEM. F, bar graphs showing percentage of mice growing palpable tumors (numbers above bars represent number of mice presenting tumors). G, qPCR analysis of TMPRSS2 and SLC45A3 expression in control (C1) and resistant (#1) tumors treated with vehicle (Veh) or MDV3100 (MDV). TBP used to normalize expression. Data represent mean±SEM; n=3 for all groups except C1 vehicle treated, n=2. *P<0.05, **P<0.01 (Student's t-test).
Figure 5B:
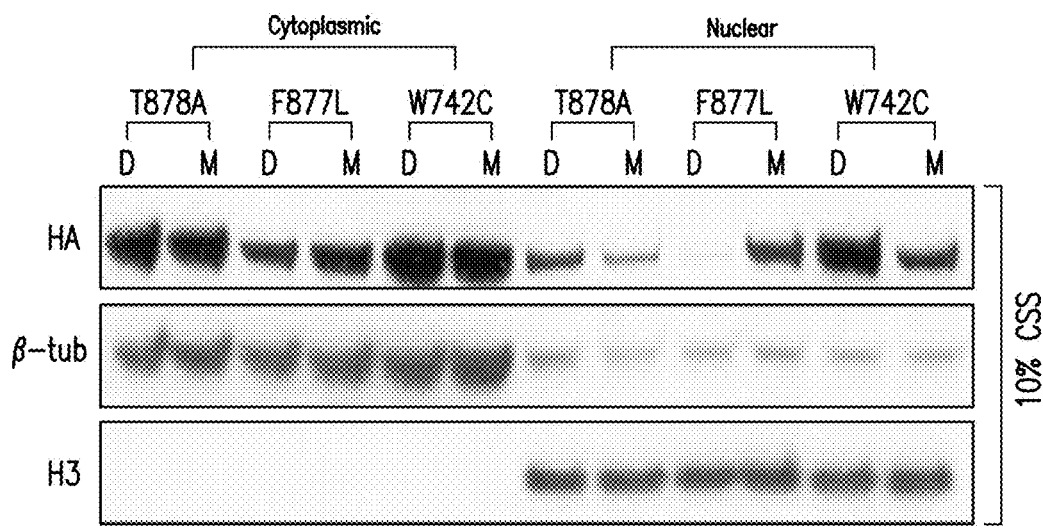

Example 6. F877L/T878A Mutant AR Confers Phenotypic Resistance to MDV3100 in Genetically Engineered LNCaPs Although the F877L and F877L/T878A alleles can potently reactivate the AR pathway in the presence of MDV3100, it is still unclear whether this rescue in pathway activity sufficiently translates to phenotypic resistance—particularly in the strongly resistant clones that harbor several other mutations. To sufficiently address this question, this disclosure engineers LNCaP cells to inducibly express T878A, F877L/T878A and W742C/T878A mutant ARs. Expression level of F877L/T878A AR is significantly lower than that of T878A and W41C/T878A mutant ARs, as assessed by qPCR and western analysis. In support of previous reports, expression of all T878A-bearing mutant alleles and the W742C/T878A allele promoted an antagonist-to-agonist switch specific for hydroxyflutamide (Fenton et al. 1997; and Hara et al. 2003); and bicalutamide (Hara et al. 2003), respectively (FIG. 15). In contrast, despite the weak expression of the F877L/T878A allele, a significant rescue of AR pathway activity is observed specifically in the presence of MDV3100, confirming the antagonist-to-agonist switch (FIG. 5a and FIG. 15). Furthermore, ectopic expression of the T878A and W742C/T878A alleles only weakly rescued AR signaling in the presence of MDV3100, once again confirming the specificity and potency of the novel F877L mutation (FIG. 5a and FIG. 15). Consistent with the gene expression data, nuclear localization of AR is significantly impaired in the T878A expressing line whereas localization of AR is unaffected in the F877L/T878A line upon treatment with MDV3100, confirming sustained AR activity in the F877L line (FIG. 5b).

Figure 16B:
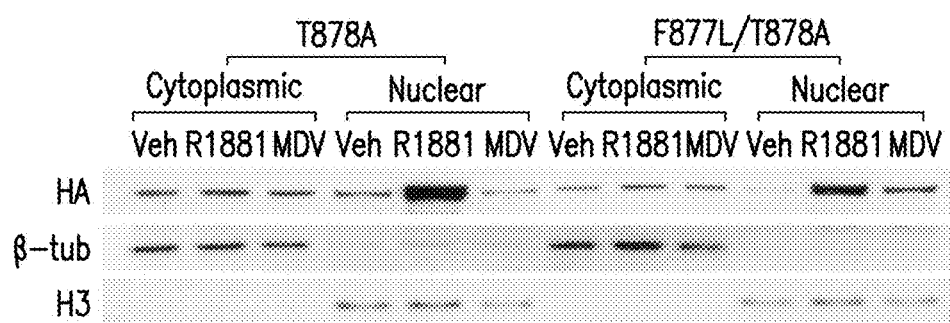
Figure 17A:
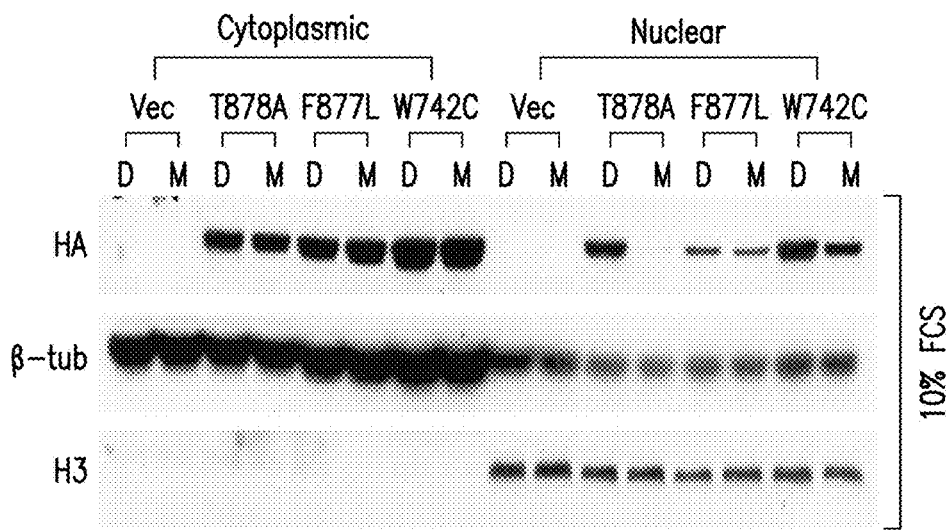
FIG. 17. F877L mutation in AR promotes nuclear translocation in the presence of MDV3100. A, western analysis of exogenous AR (HA) expression in cytoplasmic and nuclear fractions isolated from various engineered lines treated with DMSO (D) or 10 μM MDV3100 (M) in media supplemented with 10% FCS. All lines were pretreated with Dox for 3 d prior to treatment with DMSO or MDV3100 for 24 h. F877L, F877L/T878A; W742C, W742C/T878A. β-tubulin (β-tub) was probed to validate purity of cytoplasmic fractions and histone H3 (H3) was probed to validate purity of nuclear fractions. B, nuclear:cytoplasmic ratio of exogenous AR expression (HA-tagged AR) in T878A (red bars), F877L/T878A (green bars) and W742C/T878A (blue bars) overexpressing lines treated with DMSO or 10 μM MDV3100 (MDV) for 24 h. Western blot data presented in FIG. 5B and panel A was analyzed by ImageJ to determine the nuclear:cytoplasmic ratios. Cells were treated with doxycycline for 3 d prior to treatment with DMSO or MDV3100 in indicated culture conditions (10% FCS or 10% CSS).
Figure 17B:
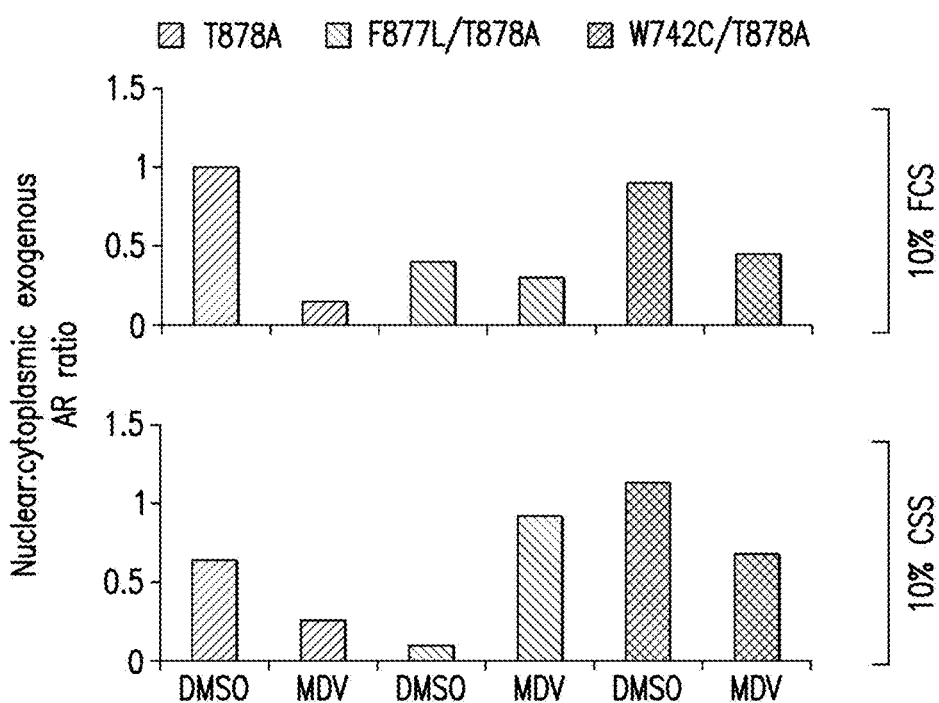

The full potential of the F877L/T878A mutant AR to utilize MDV3100 as an agonist is realized when a similar experiment is performed under androgen-depleted conditions. Whereas expression of the T878A and W742C/T878A alleles minimally rescue pathway activity, expression of the F877L/T878A allele enhances KLK3 and NKX3-1 expression 3-4 fold under MDV-treatment conditions (FIG. 16a). Interestingly, the W742C/T878A AR displays constitutive active functions, driving expression of KLK3 and NKX3-1 under baseline conditions (FIG. 16). The changes in expression levels observed above faithfully parallel the changes in localization of AR—with F877L/T878A AR becoming increasingly nuclear localized following treatment with MDV3100 (FIGS. 16b and 5b). Once again, W742C/T878A AR showed constitutive activity as enhanced nuclear localization is observed at baseline (FIG. 5b).

Figure 5C:
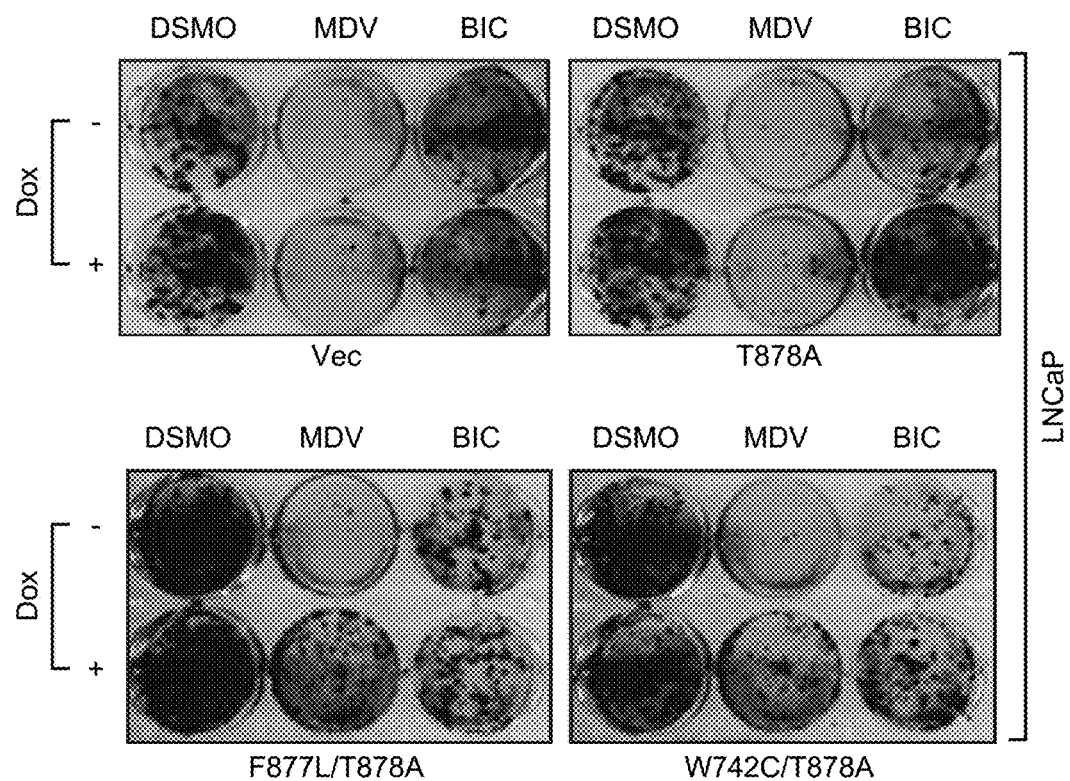
Figure 5D:
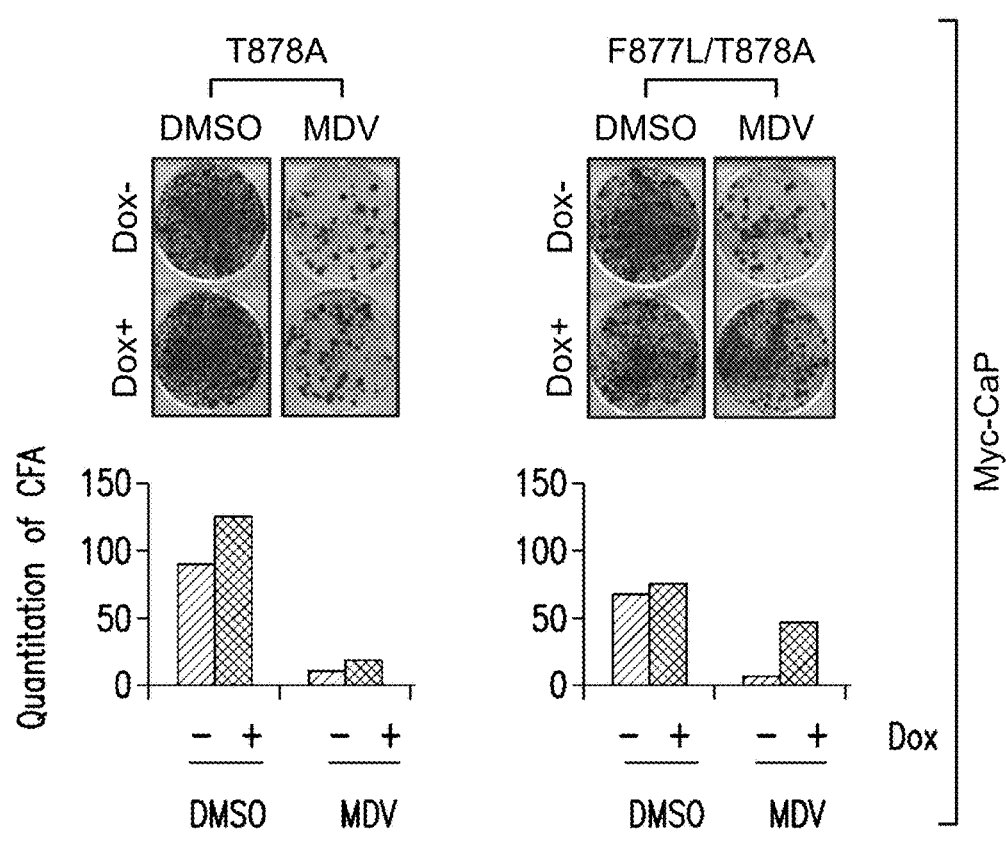
Figure 18A:
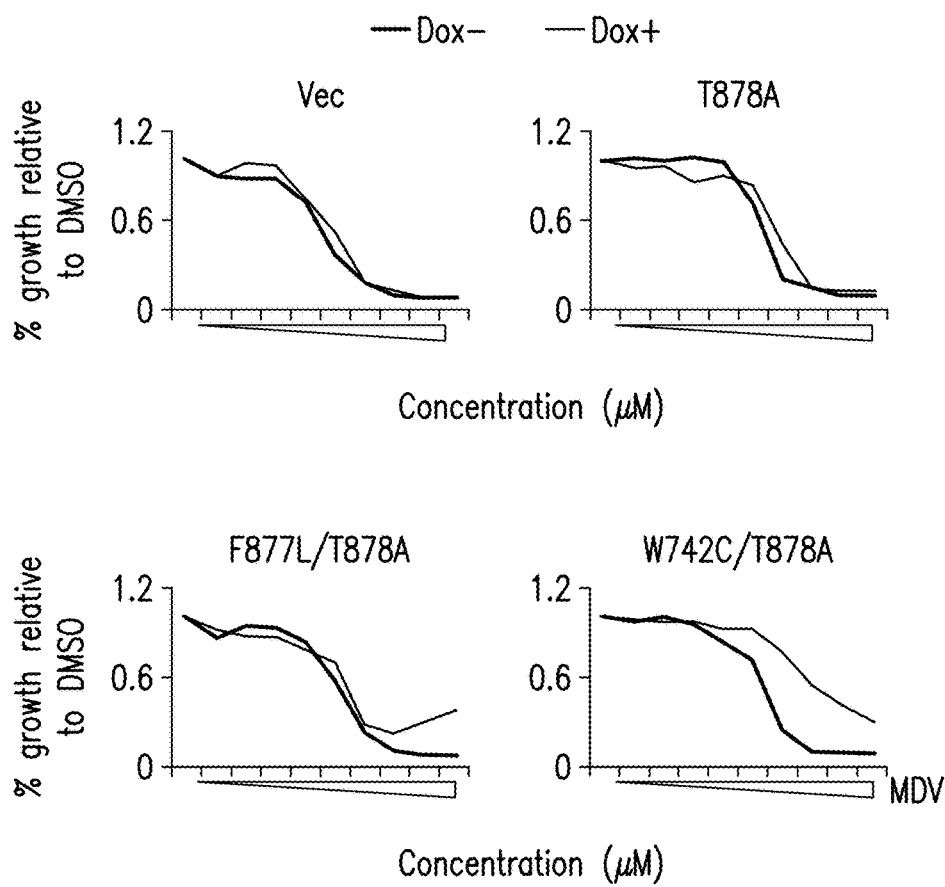
FIG. 18. F877L/T878A and W742C/T878A mutant ARs confer phenotypic resistance to MDV3100. A, growth inhibition curves generated for engineered lines treated with increasing concentrations of MDV3100 up to 10 μM. Dox−, red; Dox+, green. Data presented as percent growth relative to DMSO treatment condition as measured by CellTiter-Glo assay. B, phase contrast images of MDV3100-treated cells from A after 10 d of treatment. Scale bar, 50 µm.
Figure 18B:
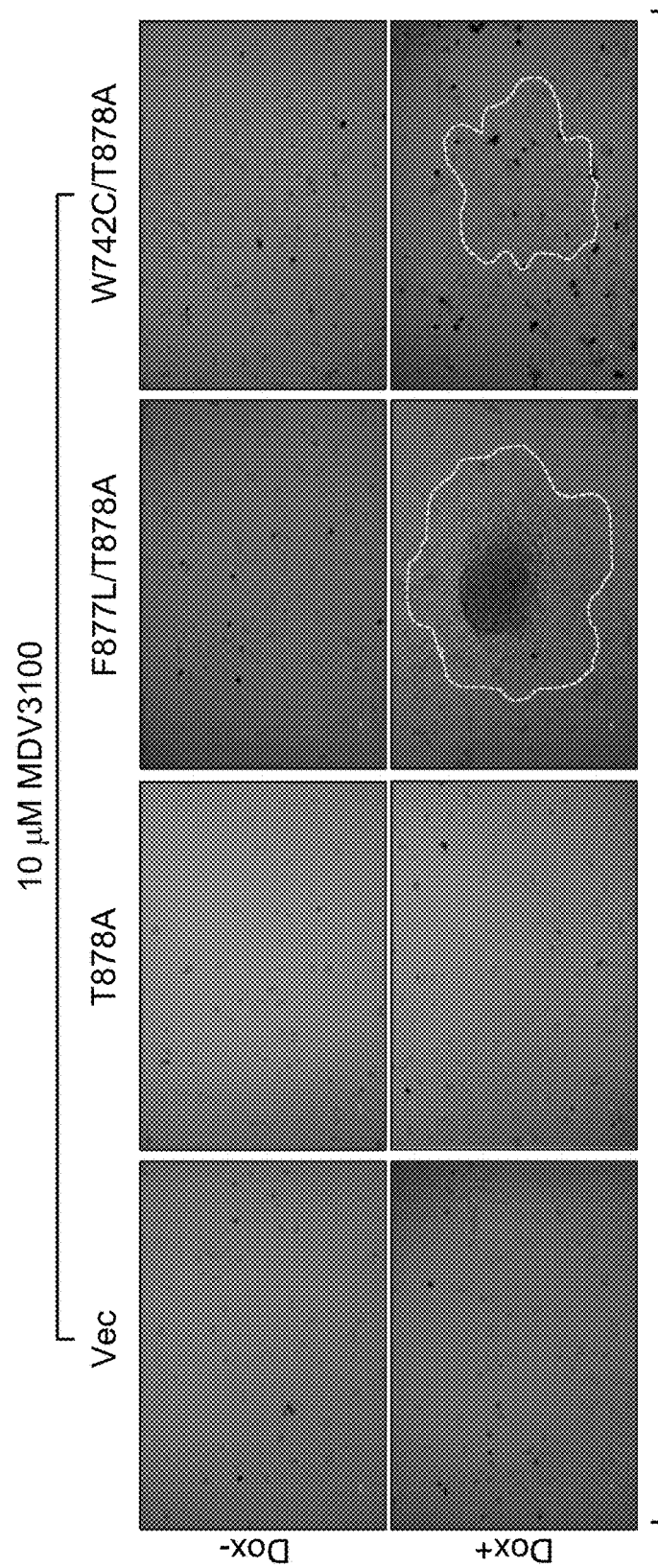
Figure 19A:
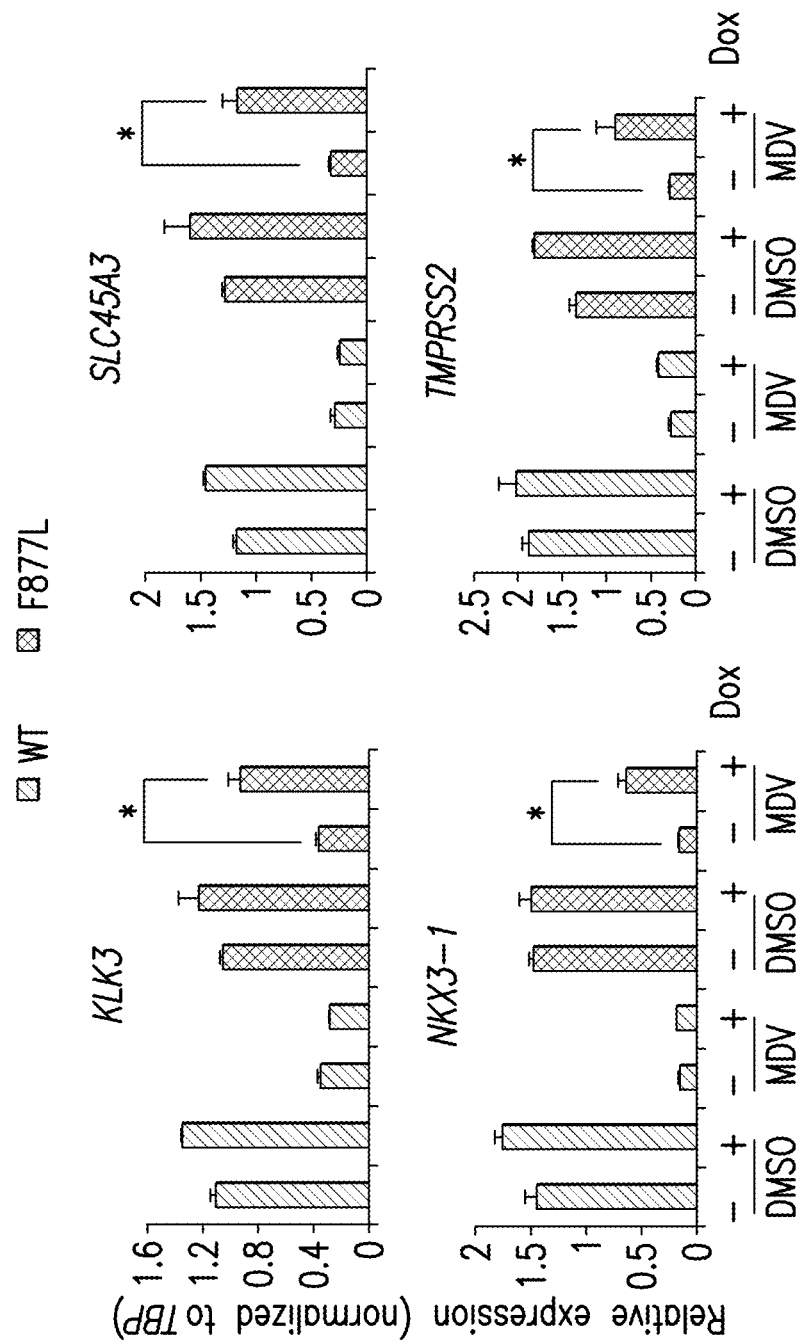
FIG. 19. AR-F877L overexpression in LNCaP cells is sufficient to drive genetic and phenotypic resistance to MDV3100. A, qPCR analysis showing relative expression of downstream target genes of AR (KLK3, NKX3-1, SLC45A3, TMPRSS2) in AR-WT (red bars) and AR-F877L (green bars) expressing LNCaP cells under DMSO and MDV3100 treatment conditions. Cells were treated with Dox (+) for 2 days prior to treatment with DMSO or MDV3100 for 24 h. Data represent mean±SEM. *P<0.05 (Student's t-test). B, colony-formation assays showing sustained growth of LNCaP cells expressing AR-F877L (Dox+) under various MDV3100 concentrations (noted in black font, µM).
Figure 19B:
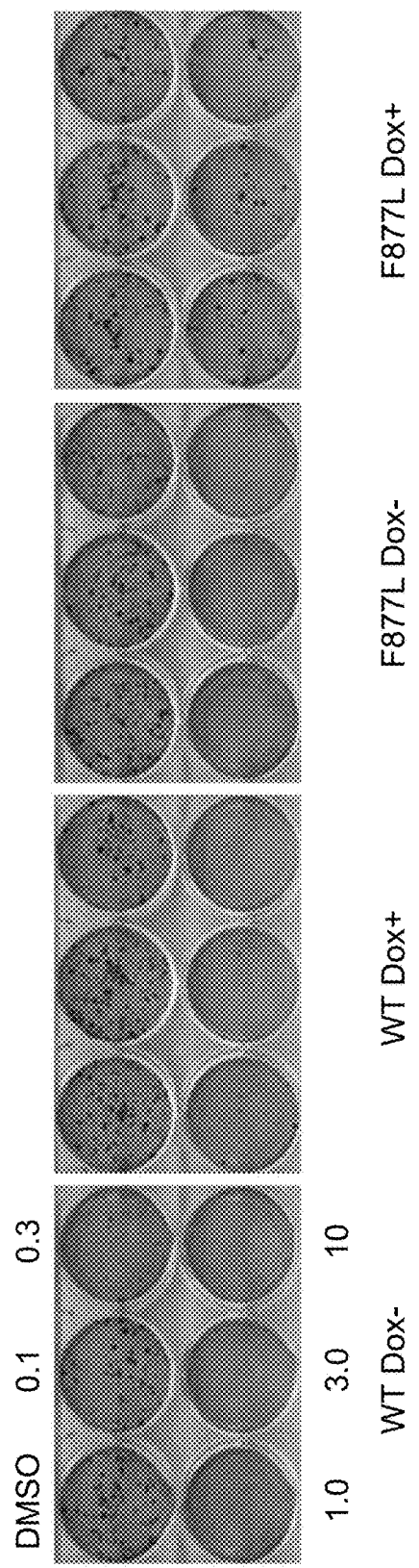
Figure 20:
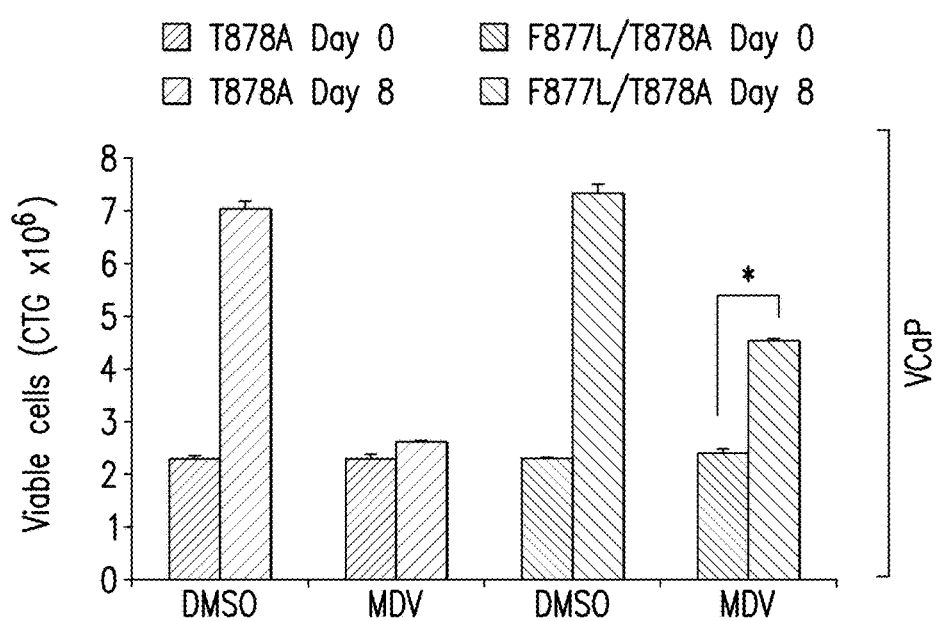
FIG. 20. VCaP cells stably expressing the F877L mutation in AR are partially resistant to MDV3100. AR-T878A expressing VCaP cells remain sensitive to MDV3100 (left) whereas expression of AR-F877L/T878A results in partial growth under MDV3100 treatment conditions (right). Data represent mean±SEM. *P<0.05 (Student's t-test).
Figure 21:
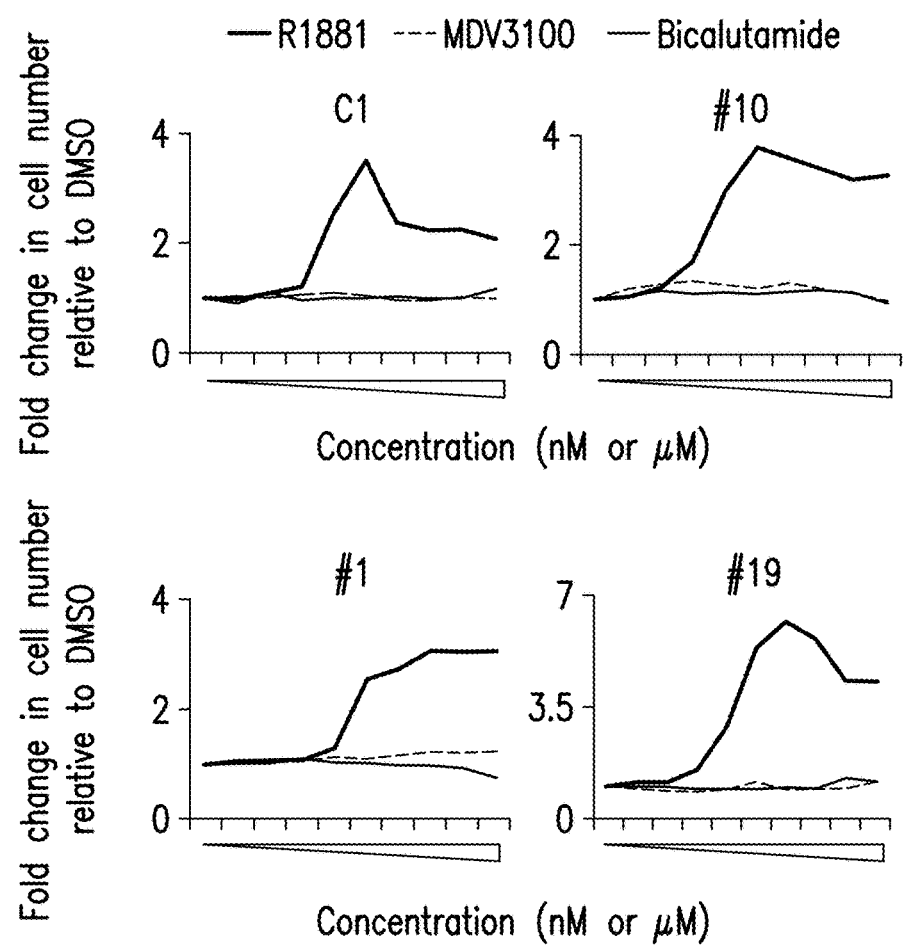
FIG. 21. MDV3100 treatment of clones harboring AR-F877L variant fails to promote cellular growth in androgen-depleted media in vitro. Line graphs depicting impact of increasing concentrations of R1881 (red), MDV3100 (green) and bicalutamide (blue) treatment on cellular growth in cells cultured in RPMI 1640 supplemented with 10% CSS. Maximum doses applied were 10 nM R1881 and 10 µM for MDV3100 and bicalutamide. Data presented as fold change in cell number relative to DMSO treatment condition (measured by CellTiter-Glo assay). Cells were treated for 13 d prior to analysis.
Figure 22A:
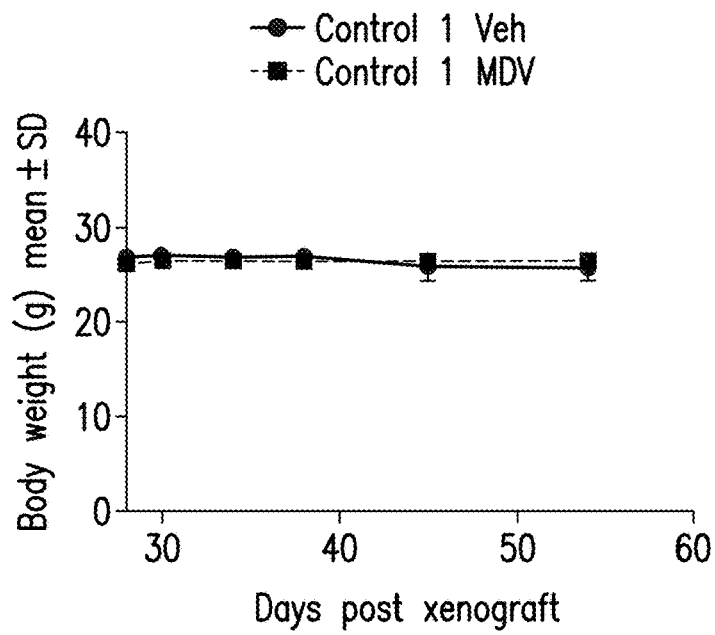
FIG. 22. Body weight measurements for control 1 and clone #1 xenografts. A, control 1 and B, clone #1 xenograft body weights were measured once per week. Data presented as mean±SD.
Figure 22B:
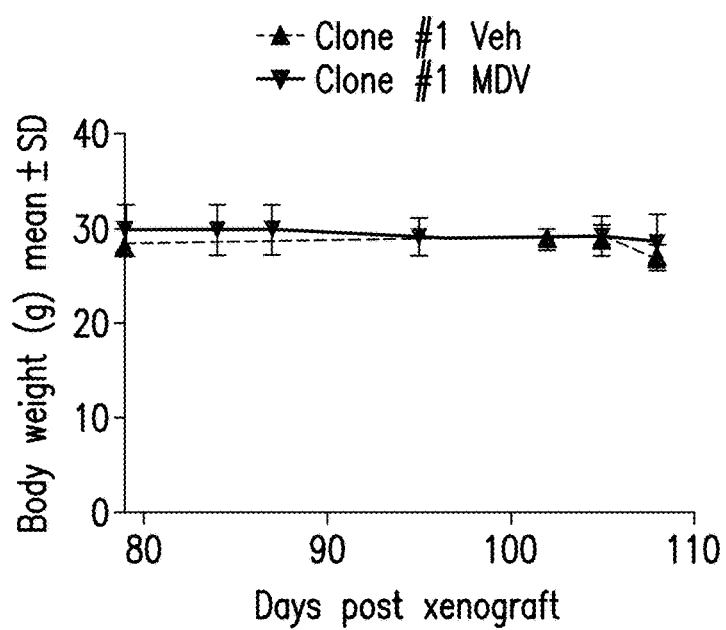

Having firmly established that the F877L/T878A mutant allele can utilize MDV3100 as an agonist, this disclosure next tests whether ectopic expression of the F877L/T878A AR can confer phenotypic resistance. Whereas expression of the T878A allele failed to rescue growth, expression of the F877L/T878A allele significantly rescued growth under MDV3100 conditions (FIG. 5c and FIG. 18a,b). Consistent with earlier observations (FIG. 15), the F877L/T878A overexpression line remained sensitive to bicalutamide (FIG. 5c). Interestingly, ectopic expression of W742C/T878A also significantly rescued growth under MDV3100 and bicalutamide treatment conditions—with resistance to MDV3100 likely being indirect, due in part to its constitutive activity (FIGS. 5b, 16).

Example 7. Use of Mutant AR(F877) to Screen for Drugs that Sensitize Mutant AR

Two methods that this disclosure has applied include 1) transactivation and 2) gene expression analysis to determine if compounds that target the AR pathway can be used as inhibitors of mutant AR function. Both methods are clearly outlined in methods section.

Briefly, for transactivation assays, AR reporter, a control plasmid and WT or mutant AR plasmids will be co-transfected 4 hours prior to treatment with DMSO, agonist or antagonist of interest. The AR reporter comprises a ARE (androgen response element sequence, to which AR binds), a promoter and a reporter gene, in this case, luciferase. 16 h following treatment, bioluminescence will be quantitated. This disclosure expects that WT AR will activate the AR reporter in the presence of R1881 (agonist) and the signal should be sufficiently suppressed in the presence of MDV3100 or other antagonists. However, for F877L AR, this disclosure expects there to be a sufficient activation of AR-reporter activity in the presence of agonist and MDV3100. Our hope will be that novel antagonist will sufficiently block F877L AR function—in a manner similar to bicalutamide.

In addition to transactivation assays, gene expression analysis of canonical AR genes, such as KLK3, TMPRSS2, NKX3-1 and SLC45A3, may also be monitored. This experiment is similar to the experiment outlined in FIG. 5b except that MDV3100 may be substituted for a novel compound(s). This disclosure would expect that whereas MDV3100 may be used as an agonist to rescue signaling, a novel compound may be effective in maintaining suppression of signaling activity in F877L-AR bearing cells.

Example 8. The F877L Mutation is Sufficient to Induce Genetic and Phenotypic Resistance to MDV3100 in Genetically Engineered LNCaPs Given that strongly resistant clones harbor several sequence variants in addition to the F877L mutation, we wanted to formally test whether the AR-F877L variant is sufficient to promote an MDV3100-resistant growth phenotype. To this end, LNCaP cells were engineered to inducibly express T878A, F877L/T878A and W742C/T878A mutant ARs. In support of previous reports, expression of all T878A-bearing mutant alleles and the W742C/T878A allele promoted an antagonist-to agonist switch specific for hydroxyflutamide (Tan et al. 1997 Mol. Endocrin. 11:450-9; Fenton et al. 1997 Clin. Cancer Res. 3: 1383-8; and Veldscholte et al. 1990 Biochem. Biophys. Res. Comm. 173: 534-40) and bicalutamide (Hara et al. 2003 Cancer Res. 63: 149-53), respectively, based on the regulation of the AR target gene KLK3 (PSA).

Despite the slightly lower expression of AR-F877L/T878A, a significant rescue of AR pathway activity was observed under 10% FCS culture conditions and a significant agonist effect was observed under 10% CSS culture conditions. The influence of AR-F877L/T878A on pathway activity closely paralleled changes in localization of AR as AR-F877L/T878A showed greater nuclear influx (MDV3100 vs. DMSO) relative to the T878A line, under both 10% FCS and 10% CSS culture conditions. Unexpectedly, we also observed a significant rescue of pathway activity in the W742C/T878A line, likely due to the constitutive active function conferred by the double mutation as reported previously (Hara et al. 2003 Cancer Res. 63: 149-53). Having established that AR-F877L/T878A can utilize MDV3100 as an agonist, we next tested whether ectopic expression of AR-F877L/T878A was sufficient to confer phenotypic resistance. Although only a modest rescue in growth was observed in a short-term proliferation assay, a robust rescue was observed in a long-term colony formation assay in response to MDV3100, but not bicalutamide. Notably, the W742C/T878A line also showed significant growth in the presence of MDV3100, consistent with the rescue of pathway activity observed earlier.

To assess whether the T878A mutation is necessary for the resistance phenotype, LNCaP cells were engineered to stably express the single mutant AR-F877L.

Consistent with the transactivation data, ARF877L conferred genetic and phenotypic resistance to MDV3100, suggesting that F877L—alone or in conjunction with T878A—is equally as capable of conferring an agonist switch.

Example 9. The Resistance Conferring Role of AR-F877L is Broadly Applicable to Several Prostate Cancer Lines Given that the F877L mutation in AR can promote resistance to MDV3100 in PTENnull LNCaP cells, we next questioned whether this mutation is sufficient to broadly confer resistance in PCa lines of various genetic backgrounds. To this end, human VCaP (harboring TMPRSS2-ERG fusion and AR amplification) and murine Myc-CaP (overexpressing Myc) lines were transduced to stably express the mutant AR.

Consistent with the resistance phenotype observed in LNCaP cells, both lines also presented partial resistance to MDV3100, suggesting that F877L mutation in AR has the potential for conferring resistance to MDV3100 under various genetic contexts.

Taken together, our data implicates a direct role for AR-F877L, AR-F877L/T878A and potentially constitutively active AR variants, such as W742C/T878A, as drivers of resistance to MDV3100. Whereas constitutively active variants may promiscuously promote resistance to various classes of anti-androgens, we show that F877L mutation in AR selectively promotes resistance to MDV3100.

Example 10. AR-F877L-Bearing Cells are Resistant to MDV3100 in Castrate Setting in Vivo Having shown that the F877L mutation in AR confers an agonist switch for MDV3100 that can promote resistance, we next asked whether F877L-bearing cells become dependent on this switch for cellular growth under androgen-deprivation conditions, a dependence that has been observed in the clinic for other anti-androgens such as flutamide (Suzuki et al. 1996 Prostate 29: 153-8). Interestingly, although the switch did not drive proliferation of F877L bearing clones in vitro, we observed a marked dependence on MDV3100 for growth in vivo when the F877L-bearing cells were implanted into castrated male mice. Whereas control (C1) tumors showed immediate stasis upon MDV3100 treatment, resistant tumors (clone #1) failed to grow until stimulated by MDV3100. Specifically, after a prolonged period of stasis, 10 of 15 mice treated with MDV3100 developed rapidly growing tumors compared to 2 of 15 in the vehicle group (P=0.0078, Fishers exact t-test, two-tailed), while the tumor take rates of control cells (C1) were indistinguishable (9 of 15 vs. 10 of 15). Furthermore, resistant tumors continued to grow in the presence of MDV3100, in agreement with earlier in vitro observations, cumulatively suggesting that AR-F877L-bearing cells require MDV3100 for growth in vivo. No significant body weight loss was observed during the treatment period in all four groups. End point molecular analysis confirmed an agonist switch of MDV3100 associated with the F877L mutation in vivo as resistant tumors treated with MDV3100 showed modestly higher AR pathway activity, as shown by AR target gene expression, relative to vehicle-treated resistant tumors, and significantly higher activity relative to vehicle-treated control tumors. These data cumulatively highlight the dependence of F877L bearing cells to MDV3100 for in vivo growth under androgen-deprivation conditions.

Example 11. Targeting CDK4/6 as a Therapeutic Strategy for Overcoming MDV3100 Resistance Having established that AR-F877L can promote resistance to MDV3100 under various genetic contexts in vitro and in vivo, we next aimed to develop rational strategies to antagonize the mutant allele. As an alternative to developing novel anti-androgens that continue to target the hypermutable ligand-binding pocket of AR (Balbas et al. 2013 eLife 2: e00499), we aimed to identify therapeutic strategies that may be more sustainable in the clinic. To this end, we observed a significant enrichment for genes belonging to 'cell cycle' and 'E2F1 activation' gene sets in addition to 'AR activation' in strongly resistant clones treated with MDV3100, suggesting that these clones may potentially maintain proliferation under MDV3100-treatment conditions through continued expression of E2F1 target genes. This is an appealing hypothesis as androgen signaling, a critical regulator of G1-S transition, is known to promote active CDK4/cyclin D1 assembly and hence activation of E2F1 function (Schiewer et al. End. Relat. Cancer 19: 1-12). Consistent with this notion, we observed that MDV3100-treatment suppressed expression of E2F1 target genes DHFR and TK1 in a control line, confirming AR signaling as a regulator of E2F1 function. In contrast, F877L bearing cells were capable of maintaining higher expression of DHFR and TK1 under MDV3100-treatment conditions relative to a control line (FIG. 6A). Based on these data, we reasoned that E2F1 activity may serve as a downstream effector of AR signaling, and as such, regulators of E2F1 function may serve as critical therapeutic nodes when AR-directed therapies become ineffective. In agreement with this hypothesis, we found that growth of strongly resistant clones (FIG. 6B) and LNCaP lines engineered to express AR-F877L/T878A (FIG. 6C) were as sensitive to CDK4/6 inhibitors LEE011 and PD033299, as bicalutamide. Interestingly, response to CDK4/6 inhibition was not only limited to F877L-bearing cells as androgen-independent 22Rv1 cells—a PCa line expressing WT AR and capable of maintaining AR signaling and expression of DHFR and TK1 under MDV3100 treatment conditions (FIG. 6D)—also showed strong sensitivity to CDK4/6 inhibition (FIG. 6E). These data cumulatively suggest that targeting CDK4/6 function may serve as an effective strategy for treatment of multiple mechanisms of resistance to MDV3100 and likely androgen-independence in general.

EMBODIMENTS

1. A composition comprising a polypeptide comprising Androgen Receptor or a fragment or variant thereof comprising or spanning position 877, wherein the amino acid at position 877 is substituted or deleted or is other than phenylalanine (F) (wherein the position of the amino acids is in accordance with the numbering of SEQ ID NO: 54).

2. The composition of embodiment 1, wherein the amino acid at position 877 is deleted.

3. The composition of embodiment 1, wherein the amino acid at position 877 is leucine (L).

4. A composition comprising a polypeptide comprising Androgen Receptor or a fragment or variant thereof comprising or spanning position 877, wherein the amino acid at position 877 is substituted or deleted or is other than phenylalanine (F) (wherein the position of the amino acids is in accordance with the numbering of SEQ ID NO: 54); and Wherein the polypeptide or fragment or variant thereof optionally comprises one or more mutations at other positions.

5. The composition of embodiment 4, wherein the amino acid at position 877 is not threonine (T), the amino acid at position 875 is not histidine (H), the amino acid at position 716 is not valine (V), and/or the amino acid at position 742 is not tryptophan (W).

6. The composition of embodiment 4, wherein the fragment is at least 5, at least 6, at least 7, at least 8, at least 9, at least 10, at least 15, at least 20, at least 25, at least 30, at least 35, at least 40, at least 50, at least 60, at least 75, at least 100, or at least 150, at least 200, at least 250, at least 300, at least 350, at least 400, at least 450, at least 500, at least 550, at least 600, at least 650, at least 700, at least 750, at least 800, at least 850, and/or at least 900 amino acids long.

7. The composition of embodiment 1 or 4, wherein the fragment or variant retains at least one activity of wild-type AR, which lacks a mutation at F877, or F877.

8. A composition comprising a polypeptide, or a fragment or variant thereof, having the sequence recited in SEQ ID NO: 54, or a variant thereof that differs in one or more amino acid deletions, additions, insertions or substitutions at no more than 50% of the residues in SEQ ID NO: 54, such that the polypeptide retains at least one activity of a polypeptide of SEQ ID NO: 54.

9. A composition comprising a polypeptide, or a fragment or variant thereof, having the sequence recited in SEQ ID NO: 54, or a variant thereof that differs in one or more amino acid deletions, additions, insertions or substitutions at no more than 1, 2, 3, 4, 5, 6, 7, 8, 9, 10, 15, 20, 25, 30, 35, 40, 45 or 50% of the residues in SEQ ID NO: 54, such that the polypeptide retains at least one activity of a polypeptide of SEQ ID NO: 54.

10. A composition of embodiment 9, wherein the fragment comprises at least 10 contiguous amino acids of SEQ ID NO: 54.

11. A composition of embodiment 9, wherein the fragment comprises at least 15 contiguous amino acids of SEQ ID NO: 54.

12. A composition comprising a polypeptide, or a fragment or variant thereof, wherein the amino acid sequence of the polypeptide is shown in SEQ ID NO: 54, wherein said sequence contains a mutation at or spans amino acid position 877 of SEQ ID NO: 54 such that the amino acid at position 877 is substituted or deleted or is not phenylanine (F), wherein optionally the amino acid at position 877 is not threonine (T), the amino acid at position 875 is not histidine (H), the amino acid at position 716 is not valine (V), and/or the amino acid at position at 742 is not tryptophan (W), and wherein the sequence of the fragment comprises at least 5, 10 or 15 contiguous amino acids of SEQ ID NO: 54 and comprises position 877.

13. A composition comprising a polypeptide comprising a sequence comprising any of SEQ ID NOs: 3 to 53.

14. A method of detecting a mutation at position F877 in an AR polynucleotide or polypeptide in a sample from a patient, the method comprising the steps of: (a) obtaining a sample comprising AR from the patient; and (b) determining the sequence of the AR polynucleotide or polypeptide or a portion thereof to determine if the AR comprises a mutation at position F877.

15. A method of diagnosing, prognosing and/or treating a patient, the method comprising the steps of: (a) obtaining a sample comprising AR from the patient; (b) determining the sequence of the AR polynucleotide or polypeptide or a portion thereof to determine if the AR comprises a mutation at position F877; and (c) administering or recommending the administration of a therapeutic composition comprising MDV3100 if a AR does not comprise a mutation at F877; or administering or recommending the administration of a therapeutic composition not comprising MDV3100 if a AR does comprise a mutation at F877.

16. The method of embodiment 15, wherein the therapeutic composition not comprising MDV3100 comprises bicalutatmide or a CDK4/6 inhibitor such as LEE011 or PD0332991, or a therapeutic nucleic acid.

17. A method diagnosing, prognosing and/or treating a patient, the method comprising the step of: (a) determining if the amino acids at positions 742 and 877 of an androgen receptor or fragment thereof in the patient are, respectively, tryptophan (W) and threonine (T); (b) recommending the administration of and/or administering to the patient: (1) bicalutamide or MDV3100 if the amino acids at positions 742 and 877 are, respectively, tryptophan (W) and threonine (T); or (2) a prostate disease treatment other than bicalutamide or MDV3100 if the amino acids at positions 742 and 877 are not, respectively, tryptophan (W) and threonine (T).

18. The method of embodiment 17, wherein the treatment that does not comprise bicalutamide or MDV3100 comprises a CDK4/6 inhibitor such as LEE011 or PD0332991 or a therapeutic nucleic acid.

18. A polynucleotide or an antisense polynucleotide that comprises at least 15 consecutive nucleotides, including 0, 1, 2 or 3 mismatches, having the sequence of and/or having a sequence complementary to: a first sequence encoding at least 5 contiguous amino acids of SEQ ID NO: 54, including position 877, wherein the amino acid at position 877 is substituted or deleted and is an amino acid other than phenylalanine (F).

19. The polynucleotide of embodiment 18, wherein the first sequence encodes at least 5, 6, 7, 8, 9, 10, 11, 12, 13, 14 or 15 contiguous amino acids of SEQ ID NO: 2, wherein the at least 5, 6, 7, 8, 9, 10, 11, 12, 13, 14 or 15 contiguous amino acids comprise or span position 877 of SEQ ID NO: 2, and wherein the amino acid at position 877 is not Phenylalanine (F), and wherein, optionally, the amino acid at position 877 is not threonine (T), the amino acid at 875 is not histidine (H), the amino acid at position 716 is not valine (V), and/or the amino acid at position at 742 is not tryptophan (W).

20. An expression construct or vector comprising a polynucleotide of embodiment 18 or 19.

21. A host cell comprising an expression construct or vector of embodiment 20.

22. A polynucleotide which encodes a mutant Androgen receptor comprising an amino acid sequence of SEQ ID NO: 2 except the encoded mutant Androgen receptor protein contains an leucine (L) at position 877 of SEQ ID NO: 2.

23. An expression construct or vector comprising: a promoter; and a polynucleotide segment encoding a mutant Androgen receptor or a fragment thereof, wherein the amino acid sequence of the Androgen Receptor is shown in SEQ ID NO: 2, wherein said sequence contains a mutation at amino acid position 877 of SEQ ID NO: 2 such that the amino acid at position 877 is not phenylanine (F), and wherein, optionally, the amino acid at position 877 is not threonine (T), the amino acid at 875 is not histidine (H), the amino acid at position 716 is not valine (V), and/or the amino acid at position at 742 is not tryptophan (W), and wherein the sequence of the fragment comprises at least 5 contiguous amino acids of SEQ ID NO: 2 and comprises position 877, wherein the polynucleotide segment is located downstream from the promoter, wherein transcription of the polynucleotide segment initiates at the promoter.

24. An isolated polynucleotide wherein the isolated polynucleotide or its complement encodes at least 10, 15 or 20 contiguous amino acids of SEQ ID NO: 54, wherein the at least 10 contiguous amino acids comprise or span position 877 of SEQ ID NO: 54, and wherein the amino acid at position 877 is substituted or deleted or is not Phenylalanine (F).

25. A host cell comprising a construct which comprises a promoter; and the polynucleotide of embodiment 22 or 24.

26. A method of determining the sensitivity of a cell to MDV3100, the method comprising:
(a) determining the amino acid, if any, at position 877 in Androgen Receptor in the cell, wherein the position 877 is determined in accordance to the numbering of SEQ ID NO: 54;
(b) comparing the amino acid, if any, at position 877 to a wild-type Androgen Receptor, wherein the absence of an amino acid or the presence of an amino acid other than phenylalanine indicates that the cell is not sensitive to MDV3100.

27. The method of embodiment 26, wherein the cell is a prostate cancer cell, breast cancer cell, or other AR-related disease cell.

28. The method of embodiment 27, wherein the AR-related disease is polyglutamate disease, alopecia, benign prostatic hyperplasia, hirsutism, acne, spinal and muscular atrophy or Kennedy disease.

29. A method of predicting the sensitivity of a patient of an AR-related disease to treatment with MDV3100, the method comprising:
(a) determining the amino acid, if any, at position 877 in Androgen Receptor in the sample in or obtained from the patient, wherein the position 877 is determined in accordance to the numbering of SEQ ID NO: 54;
(b) comparing the amino acid, if any, at position 877 to a wild-type Androgen Receptor, wherein the absence of an amino acid or the presence of an amino acid other than phenylalanine indicates that the patient is not sensitive to MDV3100.

30. The method of embodiment 29, wherein the AR-related disease is prostate or breast cancer.

31. The method of embodiment 29, wherein the AR-related disease is polyglutamate disease, alopecia, benign prostatic hyperplasia, hirsutism, acne, spinal and muscular atrophy or Kennedy disease.

32. A method of treating a patient with an AR-related disease, the method comprising:
(a) determining the amino acid, if any, at position 877 in Androgen Receptor in the sample in or obtained from the patient, wherein the position 877 is determined in accordance to the numbering of SEQ ID NO: 54;
(b) comparing the amino acid, if any, at position 877 to a wild-type Androgen Receptor, wherein the absence of an amino acid or the presence of an amino acid other than phenylalanine indicates that the patient is not sensitive to MDV3100;
(c) if the amino acid at position of 877 is not phenylalanine, administering a treatment which does not comprise MDV3100; or if the amino acid at position 877 is phenylalanine, administering a treatment which comprises MDV3100; and
(d) assaying for disease progression or palliation.

33. The method of embodiment 32, wherein the AR-related disease is prostate or breast cancer.

34. The method of embodiment 32, wherein the AR-related disease is polyglutamate disease, alopecia, benign prostatic hyperplasia, hirsutism, acne, spinal and muscular atrophy or Kennedy disease.

35. A method of determining the sensitivity of a cell to MDV3100, the method comprising:
(a) determining the amino acid, if any, at positions 742 and 877 in Androgen Receptor in the cell, wherein the positions 742 and 877 is determined in accordance to the numbering of SEQ ID NO: 54;
(b) comparing the amino acid, if any, at positions 742 and 877 to a wild-type Androgen Receptor, wherein the absence of an amino acid or the presence of an amino acid other than Tryptophan (W) at position 742 and the absence of an amino acid or the presence of an amino acid other than Threonine (T) at position 877 together indicate that the cell is not sensitive to MDV3100.

36. The method of embodiment 35, wherein the cell is a prostate cancer cell, breast cancer cell, or other AR-related disease cell.

37. The method of embodiment 35, wherein the AR-related disease is polyglutamate disease, alopecia, benign prostatic hyperplasia, hirsutism, acne, spinal and muscular atrophy or Kennedy disease.

38. A method of predicting the sensitivity of a patient of an AR-related disease to treatment with MDV3100, the method comprising:
(a) determining the amino acid, if any, at positions 742 and 877 in Androgen Receptor in the sample in or obtained from the patient, wherein the positions 742 and 877 is determined in accordance to the numbering of SEQ ID NO: 54;
(b) comparing the amino acid, if any, at positions 742 and 877 to a wild-type Androgen Receptor, wherein the absence of an amino acid or the presence of an amino acid other than Tryptophan (W) at position 742 and the absence of an amino acid or the presence of an amino acid other than Threonine (T) at position 877 together indicate that the patient is not sensitive to MDV3100.

39. The method of embodiment 38, wherein the AR-related disease is prostate or breast cancer.

40. The method of embodiment 38, wherein the AR-related disease is polyglutamate disease, alopecia, benign prostatic hyperplasia, hirsutism, acne, spinal and muscular atrophy or Kennedy disease.

41. A method of treating a patient with an AR-related disease, the method comprising:
(a) determining the amino acid, if any, at positions 742 and 877 in Androgen Receptor in the sample in or obtained from the patient, wherein the positions 742 and 877 is determined in accordance to the numbering of SEQ ID NO: 54;
(b) comparing the amino acid, if any, at positions 742 and 877 to a wild-type Androgen Receptor, wherein the absence of an amino acid or the presence of an amino acid other than Tryptophan (W) at position 742 and the absence of an amino acid or the presence of an amino acid other than Threonine (T) at position 877 together indicate that the patient is not sensitive to MDV3100;
(c) if the amino acid at position of 877 is not phenylalanine, administering a treatment which does not comprise MDV3100; or if the amino acid at positions 742 and 877 is phenylalanine, administering a treatment which comprises MDV3100; and
(d) assaying for disease progression or palliation.

42. The method of embodiment 41, wherein the AR-related disease is prostate or breast cancer.

43. The method of embodiment 41, wherein the AR-related disease is polyglutamate disease, alopecia, benign prostatic hyperplasia, hirsutism, acne, spinal and muscular atrophy or Kennedy disease.

44. A method of treating a patient with an Androgen Receptor (AR)-related disease, wherein the amino acid at position of 877 of AR is absent or is not phenylalanine, and wherein the method comprises the step of administering a therapeutic composition which does not comprise MDV3100.

45. The method of embodiment 44, wherein the therapeutic composition not comprising MDV3100 comprises bicalutatmide or a CDK4/6 inhibitor such as LEE011 or PD0332991, or a therapeutic nucleic acid 46. The method of embodiment 41, wherein the AR-related disease is prostate or breast cancer.

47. The method of embodiment 41, wherein the AR-related disease is polyglutamate disease, alopecia, benign prostatic hyperplasia, hirsutism, acne, spinal and muscular atrophy or Kennedy disease.

48. A method of treating a patient with an Androgen Receptor (AR)-related disease, wherein the amino acids at positions 742 and 877 of AR are phenylalanine, and wherein the method comprises the step of administering a therapeutic composition which comprises MDV3100.

49. The method of embodiment 48, wherein the AR-related disease is prostate or breast cancer.

50. The method of embodiment 48, wherein the AR-related disease is polyglutamate disease, alopecia, benign prostatic hyperplasia, hirsutism, acne, spinal and muscular atrophy or Kennedy disease.

51. A method of treating a patient with an Androgen Receptor (AR)-related disease, wherein the amino acid at position of 877 of AR is absent or is not phenylalanine, and wherein the method comprises the step of administering a therapeutic composition which comprises a CDK4/6 inhibitor.

52. The method of embodiment 51, wherein the CDK4/6 inhibitor is LEE011 or PD0332991.

53. The method of embodiment 51, wherein the AR-related disease is prostate or breast cancer.

54. The method of embodiment 51, wherein the AR-related disease is polyglutamate disease, alopecia, benign prostatic hyperplasia, hirsutism, acne, spinal and muscular atrophy or Kennedy disease.

55. A method of treating a patient with an Androgen Receptor (AR)-related disease, wherein the AR is wild-type or wherein the amino acid at position of 877 of AR is absent or is not phenylalanine, and wherein the method comprises the step of administering a therapeutic composition which comprises a CDK4/6 inhibitor.

56. The method of embodiment 51, wherein the CDK4/6 inhibitor is LEE011 or PD0332991.

57. The method of embodiment 51, wherein the AR-related disease is prostate or breast cancer.

58. The method of embodiment 51, wherein the AR-related disease is polyglutamate disease, alopecia, benign prostatic hyperplasia, hirsutism, acne, spinal and muscular atrophy or Kennedy disease.

59. The method of embodiment 55, wherein the CDK4/6 inhibitor inhibits growth in vitro or in vivo of a cell line expressing an Androgen Receptor wherein the amino acid at position of 877 of the Androgen Receptor is absent or is not phenylalanine.

60. The method of embodiment 59, wherein the growth inhibition is determined by proliferation rate, colony assay, microscopic assay and/or image analysis.

Unless defined otherwise, the technical and scientific terms used herein have the same meaning as that usually understood by a specialist familiar with the field to which the disclosure belongs. Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims are non-limiting and are provided below.

Although particular embodiments and claims have been disclosed herein in detail, this has been done by way of example for purposes of illustration only, or is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. Those skilled in the art will recognize or be able to ascertain, using no more than routine experimentation, many equivalents of the specific embodiments of the disclosure described herein. Such equivalents are intended to be encompassed by the following claims. Redrafting of claim scope in later filed corresponding applications may be due to limitations by the patent laws of various countries and should not be interpreted as giving up subject matter of the claims.

REFERENCES

1. Pruitt K D, Tatusova T, Brown G R, Maglott D R. NCBI Reference Sequences (RefSeq): current status, new features and genome annotation policy. Nucleic acids research. 2012; 40(Database issue):D130-5. Epub 2011/11/29.
2. Langmead B, Salzberg S L. Fast gapped-read alignment with Bowtie 2. Nature methods. 2012; 9(4):357-9. Epub 2012/03/06.
3. Trapnell C, Pachter L, Salzberg S L. TopHat: discovering splice junctions with RNA-Seq. Bioinformatics. 2009; 25(9):1105-11. Epub 2009/03/18.
4. DePristo M A, Banks E, Poplin R, Garimella K V, Maguire J R, Hartl C, et al. A framework for variation discovery and genotyping using next-generation DNA sequencing data. Nature genetics. 2011; 43(5):491-8. Epub 2011/04/12.
5. Forbes S A, Bindal N, Bamford S, Cole C, Kok C Y, Beare D, et al. COSMIC: mining complete cancer genomes in the Catalogue of Somatic Mutations in Cancer. Nucleic acids research. 2011; 39(Database issue):D945-50. Epub 2010/10/19.
6. Cingolani P, Plans A, Wang le L, Coon M, Nguyen T, Wang L, et al. A program for annotating and predicting the effects of single nucleotide polymorphisms, SnpEff: SNPs in the genome of *Drosophila melanogaster* strain w1118; iso-2; iso-3. Fly. 2012; 6(2):80-92. Epub 2012/06/26.

What is claimed is:

1. A method of treating anti-androgen resistant prostate cancer in a patient comprising administering to said patient a therapeutically effective amount of LEE011 as a single therapeutic, wherein the prostate cancer expressing an androgen receptor comprising an F877L mutation, and wherein the position of amino acid residue F877 is numbered in accordance with the amino acid sequence of SEQ ID NO: 1.

2. The method of claim 1, wherein the anti-androgen is MDV3100.

* * * * *

SEQUENCE LISTING

<160> NUMBER OF SEQ ID NOS: 70

<210> SEQ ID NO 1
<211> LENGTH: 920
<212> TYPE: PRT
<213> ORGANISM: Homo sapiens

<400> SEQUENCE: 1

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
            115                 120                 125

Arg Gly Cys Val Pro Glu Pro Gly Ala Ala Val Ala Ala Ser Lys Gly
        130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
        355                 360                 365
```

```
Leu Ala Leu Ala Gly Pro Pro Pro Pro Pro Pro Pro His Pro His
370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
            405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly Gly Gly
450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
            565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
            610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
            645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
            690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
            725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
            755                 760                 765

Leu Val Phe Asn Glu Tyr Arg Met His Lys Ser Arg Met Tyr Ser Gln
770                 775                 780

Cys Val Arg Met Arg His Leu Ser Gln Glu Phe Gly Trp Leu Gln Ile
```

| | | | | | | | | | | | | |
|---|---|---|---|---|---|---|---|---|---|---|---|---|
|785| | | | |790| | | |795| | |800|

Thr Pro Gln Glu Phe Leu Cys Met Lys Ala Leu Leu Phe Ser Ile
                 805                     810                  815

Ile Pro Val Asp Gly Leu Lys Asn Gln Lys Phe Phe Asp Glu Leu Arg
             820                     825                 830

Met Asn Tyr Ile Lys Glu Leu Asp Arg Ile Ile Ala Cys Lys Arg Lys
             835                     840                 845

Asn Pro Thr Ser Cys Ser Arg Arg Phe Tyr Gln Leu Thr Lys Leu Leu
850                       855                     860

Asp Ser Val Gln Pro Ile Ala Arg Glu Leu His Gln Phe Thr Phe Asp
865                       870                     875                 880

Leu Leu Ile Lys Ser His Met Val Ser Val Asp Phe Pro Glu Met Met
                 885                     890                 895

Ala Glu Ile Ile Ser Val Gln Val Pro Lys Ile Leu Ser Gly Lys Val
             900                     905                 910

Lys Pro Ile Tyr Phe His Thr Gln
             915                     920

<210> SEQ ID NO 2
<211> LENGTH: 2763
<212> TYPE: DNA
<213> ORGANISM: Homo sapiens

<400> SEQUENCE: 2

| | |
|---|---|
|atggaagtgc agttagggct gggaagggtc taccctcggc cgccgtccaa gacctaccga|60|
|ggagctttcc agaatctgtt ccagagcgtg cgcgaagtga tccagaaccc gggccccagg|120|
|cacccagagg ccgcgagcgc agcacctccc ggcgccagtt tgctgctgct gcagcagcag|180|
|cagcagcagc agcagcagca gcagcagcag cagcagcagc agcagcagca gcagcagcaa|240|
|gagactagcc ccaggcagca gcagcagcag cagggtgagg atggttctcc ccaagcccat|300|
|cgtagaggcc ccacaggcta cctggtcctg gatgaggaac agcaaccttc acagccgcag|360|
|tcggccctgg agtgccaccc cgagagaggt tgcgtcccag agcctggagc cgccgtggcc|420|
|gccagcaagg ggctgccgca gcagctgcca gcacctccgg acgaggatga ctcagctgcc|480|
|ccatccacgt tgtccctgct gggccccact tccccggct taagcagctg ctccgctgac|540|
|cttaaagaca tcctgagcga ggccagcacc atgcaactcc ttcagcaaca gcagcaggaa|600|
|gcagtatccg aaggcagcag cagcgggaga gcgagggagg cctcgggggc tcccacttcc|660|
|tccaaggaca attacttagg gggcacttcg accatttctg acaacgccaa ggagttgtgt|720|
|aaggcagtgt cggtgtccat gggcctgggt gtggaggcgt ggagcatct gagtccaggg|780|
|gaacagcttc gggggattg catgtacgcc ccacttttgg gagttccacc cgctgtgcgt|840|
|cccactcctt gtgccccatt ggccgaatgc aaaggttctc tgctagacga cagcgcaggc|900|
|aagagcactg aagatactgc tgagtattcc cctttcaagg aggttacac caaagggcta|960|
|gaaggcgaga gcctaggctg ctctggcagc gctgcagcag ggagctccgg gacacttgaa|1020|
|ctgccgtcta ccctgtctct ctacaagtcc ggagcactgg acgaggcagc tgcgtaccag|1080|
|agtcgcgact actacaactt tccactggct ctggccggac gccgcccccc tcgccgcct|1140|
|ccccatcccc acgctcgcat caagctggag aacccgctgg actacggcag cgcctgggcg|1200|
|gctgcggcgg cgcagtgccg ctatgggac ctggcgagcc tgcatggcgc gggtgcagcg|1260|
|ggacccggtt ctgggtcacc ctcagccgcc gcttcctcat cctggcacac tctcttcaca|1320|
|gccgaagaag gccagttgta tggaccgtgt ggtggtggtg ggggtggtgg cggcggcggc|1380|

-continued

```
ggcggcggcg gcggcggcgg cggcggcggc ggcggcggcg aggcgggagc tgtagccccc    1440
tacggctaca ctcggccccc tcagggctg gcgggccagg aaagcgactt caccgcacct     1500
gatgtgtggt accctggcgg catggtgagc agagtgccct atcccagtcc cacttgtgtc    1560
aaaagcgaaa tggcccctg gatggatagc tactccggac cttacgggga catgcgtttg     1620
gagactgcca gggaccatgt tttgcccatt gactattact ttccacccca gaagacctgc    1680
ctgatctgtg gagatgaagc ttctgggtgt cactatggag ctctcacatg tggaagctgc    1740
aaggtcttct tcaaaagagc cgctgaaggg aaacagaagt acctgtgcgc agcagaaat    1800 gattgcacta ttgataaatt ccgaaggaaa aattgtccat cttgtcgtct tcggaaatgt    1860
tatgaagcag ggatgactct gggagcccgg aagctgaaga acttggtaa tctgaaacta   1920 caggaggaag gagaggcttc cagcaccacc agccccactg aggagacaac ccagaagctg    1980
acagtgtcac acattgaagg ctatgaatgt cagcccatct ttctgaatgt cctggaagcc    2040
attgagccag gtgtagtgtg tgctggacac gacaacaacc agcccgactc ctttgcagcc    2100
ttgctctcta gcctcaatga actgggagag agacagcttg tacacgtggt caagtgggcc    2160
aaggccttgc ctggcttccg caacttacac gtggacgacc agatggctgt cattcagtac    2220
tcctggatgg ggctcatggt gtttgccatg ggctggcgat ccttcaccaa tgtcaactcc    2280
aggatgctct acttcgcccc tgatctggtt ttcaatgagt accgcatgca caagtcccgg    2340
atgtacagcc agtgtgtccg aatgaggcac ctctctcaag agtttggatg gctccaaatc    2400 acccccagg aattcctgtg catgaaagca ctgctactct tcagcattat tccagtggat    2460
gggctgaaaa atcaaaaatt ctttgatgaa cttcgaatga actacatcaa ggaactcgat    2520
cgtatcattg catgcaaaag aaaaaatccc acatcctgct caagacgctt ctaccagctc    2580
accaagctcc tggactccgt gcagcctatt gcgagagagc tgcatcagtt cacttttgac    2640
ctgctaatca agtcacacat ggtgagcgtg gactttccgg aaatgatggc agagatcatc    2700
tctgtgcaag tgcccaagat cctttctggg aaagtcaagc ccatctattt ccacacccag    2760
tga                                                                 2763
```

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: Any amino acid except Phe

<400> SEQUENCE: 3

Pro Ile Ala Arg Glu Leu His Gln Xaa Thr
1               5                   10

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Any amino acid except Phe

<400> SEQUENCE: 4

Ile Ala Arg Glu Leu His Gln Xaa Thr Phe
1               5                   10

<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Any amino acid except Phe

<400> SEQUENCE: 5

Ala Arg Glu Leu His Gln Xaa Thr Phe Asp
1               5                   10

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Any amino acid except Phe

<400> SEQUENCE: 6

Arg Glu Leu His Gln Xaa Thr Phe Asp Leu
1               5                   10

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid except Phe

<400> SEQUENCE: 7

Glu Leu His Gln Xaa Thr Phe Asp Leu Leu
1               5                   10

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid except Phe

```
<400> SEQUENCE: 8

Leu His Gln Xaa Thr Phe Asp Leu Leu Ile
1               5                   10

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid except Phe

<400> SEQUENCE: 9

His Gln Xaa Thr Phe Asp Leu Leu Ile Lys
1               5                   10

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid except Phe

<400> SEQUENCE: 10

Gln Xaa Thr Phe Asp Leu Leu Ile Lys Ser
1               5                   10

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid except Phe

<400> SEQUENCE: 11

Gln Xaa Thr Phe Asp Leu Leu Ile Lys Ser His
1               5                   10

<210> SEQ ID NO 12

<400> SEQUENCE: 12

000

<210> SEQ ID NO 13

<400> SEQUENCE: 13

000

<210> SEQ ID NO 14
```

```
<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid except Phe or absent

<400> SEQUENCE: 20

Glu Leu His Gln Xaa Thr Phe Asp Leu Leu
1               5                   10

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid except Phe or absent

<400> SEQUENCE: 21

Leu His Gln Xaa Thr Phe
1               5

<210> SEQ ID NO 22
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid except Phe or absent

<400> SEQUENCE: 22

His Gln Xaa Thr Phe Asp
1               5

<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid except Phe or absent

<400> SEQUENCE: 23

Gln Xaa Thr Phe Asp
1               5

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Glu Leu His Gln Thr
1               5

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Leu His Gln Thr Phe
1               5

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

His Gln Thr Phe Asp
```

```
<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gln Thr Phe Asp Leu
1               5

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gln Pro Ile Ala Arg Glu Leu His Gln Thr
1               5                   10

<210> SEQ ID NO 29
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Pro Ile Ala Arg Glu Leu His Gln Thr Phe
1               5                   10

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Ala Arg Glu Leu His Gln Thr Phe Asp
1               5                   10

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ala Arg Glu Leu His Gln Thr Phe Asp Leu
1               5                   10

<210> SEQ ID NO 32
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Arg Glu Leu His Gln Thr Phe Asp Leu Leu
1               5                   10

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Glu Leu His Gln Thr Phe Asp Leu Leu Ile
1               5                   10

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Leu His Gln Thr Phe Asp Leu Leu Ile Lys
1               5                   10

<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

His Gln Thr Phe Asp Leu Leu Ile Lys Ser
1               5                   10

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gln Thr Phe Asp Leu Leu Ile Lys Ser His
1               5                   10

<210> SEQ ID NO 37
<211> LENGTH: 11
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(11)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 37

Gln Pro Ile Ala Arg Glu Leu His Gln Xaa Xaa
1               5                   10

<210> SEQ ID NO 38
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(10)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 38

Pro Ile Ala Arg Glu Leu His Gln Xaa Xaa Phe
1               5                   10

<210> SEQ ID NO 39
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(9)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 39

Ile Ala Arg Glu Leu His Gln Xaa Xaa Phe Asp
1               5                   10

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(8)
<223> OTHER INFORMATION: Any amino acid
<220> FEATURE:
<221> NAME/KEY: source
<223> OTHER INFORMATION: /note="see specification as filed for detailed
``` description of substitutions and preferred embodiments"

<400> SEQUENCE: 40

Ala Arg Glu Leu His Gln Xaa Xaa Phe Asp Leu
1               5                   10

<210> SEQ ID NO 41
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(7)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 41

Arg Glu Leu His Gln Xaa Xaa Phe Asp Leu Leu
1               5                   10

<210> SEQ ID NO 42
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(6)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 42

Glu Leu His Gln Xaa Xaa Phe Asp Leu Leu Ile
1               5                   10

<210> SEQ ID NO 43
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(5)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 43

Leu His Gln Xaa Xaa Phe Asp Leu Leu Ile Lys
1               5                   10

<210> SEQ ID NO 44
<211> LENGTH: 11

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(4)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 44

His Gln Xaa Xaa Phe Asp Leu Leu Ile Lys Ser
1               5                   10

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(3)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 45

Gln Xaa Xaa Phe Asp Leu Leu Ile Lys Ser His
1               5                   10

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 46

Gln Pro Ile Ala Arg Glu Leu Xaa Gln Xaa Xaa
1               5                   10

<210> SEQ ID NO 47
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 47

Pro Ile Ala Arg Glu Leu Xaa Gln Xaa Xaa Phe
1               5                   10

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 48

Ile Ala Arg Glu Leu Xaa Gln Xaa Xaa Phe Asp
1               5                   10

<210> SEQ ID NO 49
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 49

Ala Arg Glu Leu Xaa Gln Xaa Xaa Phe Asp Leu
1               5                   10

<210> SEQ ID NO 50
<211> LENGTH: 11
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 50

Arg Glu Leu Xaa Gln Xaa Xaa Phe Asp Leu Leu
1               5                   10

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 51

Glu Leu Xaa Gln Xaa Xaa Phe Asp Leu Leu Ile
1               5                   10

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 52

Leu Xaa Gln Xaa Xaa Phe Asp Leu Leu Ile Lys
1               5                   10

<210> SEQ ID NO 53
<211> LENGTH: 11
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: source
<223> OTHER INFORMATION: /note="see specification as filed for detailed
      description of substitutions and preferred embodiments"

<400> SEQUENCE: 53

Xaa Gln Xaa Xaa Phe Asp Leu Leu Ile Lys Ser
1               5                   10

<210> SEQ ID NO 54
<211> LENGTH: 920
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (877)..(877)
<223> OTHER INFORMATION: Any amino acid except Phe or absent

<400> SEQUENCE: 54

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala
            35                  40                  45

Pro Pro Gly Ala Ser Leu Leu Leu Leu Gln Gln Gln Gln Gln Gln Gln
        50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220
```

-continued

```
Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
            245                 250                 255

Leu Ser Pro Gly Glu Gln Leu Arg Gly Asp Cys Met Tyr Ala Pro Leu
        260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
        290                 295                 300

Asp Thr Ala Glu Tyr Ser Pro Phe Lys Gly Tyr Thr Lys Gly Leu
305                 310                 315                 320

Glu Gly Glu Ser Leu Gly Cys Ser Gly Ser Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Asn Phe Pro
        355                 360                 365

Leu Ala Leu Ala Gly Pro Pro Pro Pro Pro Pro His Pro His
370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly
        450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
        530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
        610                 615                 620

Met Thr Leu Gly Ala Arg Lys Leu Lys Lys Leu Gly Asn Leu Lys Leu
625                 630                 635                 640
```

Gln Glu Glu Gly Glu Ala Ser Ser Thr Thr Ser Pro Thr Glu Glu Thr
            645                 650                 655

Thr Gln Lys Leu Thr Val Ser His Ile Glu Gly Tyr Glu Cys Gln Pro
    660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
        690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Xaa Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
attgcgagag agctgcatca                                                    20

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
ttctcgtcac tattggcctc                                                    20

<210> SEQ ID NO 57

<400> SEQUENCE: 57

000

<210> SEQ ID NO 58
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
gagagctgca tcagttcgct tttgacctgc taatc                                   35

<210> SEQ ID NO 59
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
gattagcagg tcaaaagcga actgatgcag ctctc                                   35

<210> SEQ ID NO 60
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
cattcagtac tcctgcatgg ggctcatggt g                                       31

<210> SEQ ID NO 61
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
caccatgagc cccatgcagg agtactgaat g                                       31

<210> SEQ ID NO 62
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
gtcattcagt actccctgat ggggctcatg g                                       31

```
<210> SEQ ID NO 63
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ccatgagccc catcagggag tactgaatga c                              31

<210> SEQ ID NO 64
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
gagagctgca tcagctcact tttgacctg                                 29

<210> SEQ ID NO 65
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
caggtcaaaa gtgagctgat gcagctctc                                 29

<210> SEQ ID NO 66
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
gagagctgca tcagctcgct tttgacctg                                 29

<210> SEQ ID NO 67
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
caggtcaaaa gcgagctgat gcagctctc                                 29

<210> SEQ ID NO 68
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: CDS
<222> LOCATION: (2)..(13)

<400> SEQUENCE: 68 t cag ttc gct ttt g                                              14
  Gln Phe Ala Phe
  1

<210> SEQ ID NO 69
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gln Phe Ala Phe
1

<210> SEQ ID NO 70
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
aagcgaactg a                                                     11
```